United States Patent
Wogulis

(10) Patent No.: US 9,879,244 B2
(45) Date of Patent: Jan. 30, 2018

(54) XYLANASE VARIANTS AND POLYNUCLEOTIDES ENCODING SAME

(71) Applicant: NOVOZYMES A/S, Bagsvaerd (DK)

(72) Inventor: Mark Wogulis, Davis, CA (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/896,438

(22) PCT Filed: May 30, 2014

(86) PCT No.: PCT/US2014/040148
§ 371 (c)(1),
(2) Date: Dec. 7, 2015

(87) PCT Pub. No.: WO2014/197296
PCT Pub. Date: Dec. 11, 2014

(65) Prior Publication Data
US 2016/0122737 A1  May 5, 2016

Related U.S. Application Data

(60) Provisional application No. 61/831,278, filed on Jun. 5, 2013.

(51) Int. Cl.
| | |
|---|---|
| *C12P 19/14* | (2006.01) |
| *C12N 9/42* | (2006.01) |
| *C12P 21/06* | (2006.01) |
| *C12P 19/34* | (2006.01) |
| *C12N 15/00* | (2006.01) |
| *C12N 1/20* | (2006.01) |
| *C12N 1/00* | (2006.01) |
| *C12N 9/24* | (2006.01) |

(52) U.S. Cl.
CPC ......... *C12N 9/2482* (2013.01); *C12N 9/248* (2013.01); *C12Y 302/01008* (2013.01)

(58) Field of Classification Search
CPC ................. C12N 9/248; C12N 9/2482; C12Y 302/01008

USPC ......... 435/99, 209, 69.1, 91.1, 320.1, 252.3, 435/254.11; 536/23.1, 23.2; 530/350
See application file for complete search history.

(56) References Cited

U.S. PATENT DOCUMENTS 7,514,110 B1 * 4/2009 Van Den Hombergh ............ A21D 8/042

FOREIGN PATENT DOCUMENTS

| EP | WO2009/133036 A1 * | 11/2009 | ............... C12P 9/24 |
| WO | 03/020923 A1 | 3/2003 | |
| WO | 2012/030849 A1 | 3/2012 | |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Neirman et al, 2005, Nature 438(7071), 1151-1156.
Neirman et al, 2008—Genbank Access No. XP_001258500.
Neirman et al, 2008—Genbank Access No. XP_751237.

* cited by examiner

*Primary Examiner* — Ganapathirama Raghu
(74) *Attorney, Agent, or Firm* — Robert Starnes

(57) ABSTRACT

The present invention relates to xylanase variants. The present invention also relates to polynucleotides encoding the variants; nucleic acid constructs, vectors, and host cells comprising the polynucleotides; and methods of using the variants.

18 Claims, 2 Drawing Sheets

```
      M  V  H  L  S  S  L     A  A  A     L  A  A     L  P  L
  1 ATGGTCCATC TATCTTCATT GGCAGCAGCC CTGGCTGCTC TGCCTCTGTA CTCACGAGAG
                                  V
    GAGGAACAGC TTTGACATTG CTATAGTGTA TATGGAGCTG GCCTGAACAC AGCCAAGGAC
 71   L  K  Y  F     G  S  A     T  D  N     P  E  L  T     A  K  G

TAAAGTACTT TGGTTCCGCC ACGGACAATC CAGAGCTCAC GGACTCTGCG TATGTCGCGC
141                                                                AA
      T  D  D     F  G  Q     I  T  P  G     N  S  M     D  S  A
                                                                     Y  V  A
    CACCGATGAT TTTGGTCAAA TCACACCCGG AAACTCCATG GGATGCCACC GAGCCTTCTC
211                                             W                               Q  L  S  N
                                                  D  A  T     E  P  S     AACTGAGCAA
                                                                              Q  N  S  F
    ATTGCCTCAA AAGCTAATTG GTTGTTTTGT TTGGATAGTG GGATGCCACC GAGCCTTCTC TACGTCTGCC TCCCTGGAGC
281   S  F  A     N  G  D     A  V  V  N     L  A  N     K  N  G     Q  L  M  R     C  H  T
    TTCGTTCGCA AATGGAGACG CCGTGGTCAA TCTGGCGAAC AAGAATGGCC AGCTGATGCG ATGCCATACT AGAATTCTTT
351   L  V  W     H  S  Q  L     P  N  W
    CTGGTCTGGC ACAGTCAGCT ACCGAACTGG GGTATGTAAA CGTCTTGTCT ATTCTCAAAT ACTCTCTAAC
421               S  S  G     S  W  T     N  A  T  L     L  A  A     M  K  N     H  I  T  N
                    V
    AGTTGACAGT CTCTAGCGGG TCATGGACCA ATGCGACCCT TTTGGCGGCC ATGAAGAATC ATATCACCAA
491   V  V  T     H  Y  K     G  K  C  Y     A  W  D     V  V  N
                                                                   E
    TGTGGTTACT CACTACAAGG GGAAGTGCTA CGCCTGGGAT GTTGTCAATG AAGGTTTGTT GCTCCATCTA
561                                                                 A  L  N     E  D  G     T  F  R  N
    TCCTCAATCT AGCCCCTGAA CTGTCAATCT ATACATTCCT ATTGCGTTCG GAGGACGGTA CTTTCCGTAA
631   S  V  F     Y  Q  I     I  G  P  A     Y  I  P     I  A  F     A  T  A  A     A  D
    CTCTGTCTTC TACCAGATCA TCGGCCCAGC ATACATTCCT ATTGCGTTCG CCACGGCTGC TGCCGCAGAT
701   P  D  V     K  L  Y  Y     N  D  Y     N  I  E     Y  S  G  A     K  A  T     A  A  Q
    CCCGACGTGA AACTCTACTA CAACGACTAC AACATTGAAT ACTCAGGCGC CAAAGCGACT GCTGCCCAGA
771   N  I  V  K     M  I  K     A  Y  G     A  K  I  D     G  V  G     L  Q  A     H  F  I  V
```

Fig. 1A

```
 841  ATATCGTCAA GATGATCAAG GCCTACGGCG CGAAGATCGA CGGCGTCGGC CTCCAGGCAC ACTTTATCGT
       G  S  T     P  S  Q     S  D  L  T     T  V  L     K  G  Y     T  A  L  G     V  E  V
 911  CGGCAGCACT CCGAGTCAAT CGGATCTGAC GACCGTCTTG AAGGGCTACA CTGCTCTCGG CGTTGAGGTG
       A  Y  T     E  L  D  I     R  M  Q     L  P  S     T  A  A  K     L  A  Q     Q  S  T
 981  GCCTATACCG AACTTGACAT CCGCATGCAG CTGCCCCTGA CCGCCGCAAA GCTGGCCCAG CAGTCCACTG
       D  F  Q  G     V  A  A     A  C  V     S  T  T  G     C  V  G     V  T  I     W  D  W  T
1051  ACTTCCAAGG CGTGGCCGCA GCATGCGTTA GCACCACTGG CTGCGTGGGT GTCACTATCT GGGACTGGAC
       D  K  Y     S  W  V     P  S  V  F     Q  G  Y     G  A  P     L  P  W  D     E  N  Y
1121  CGACAAGTAC TCCTGGGTCC CCAGCGTGTT CCAAGGCTAC GGCGCCCCAT TGCCTTGGGA TGAGAACTAT
       V  K  K     P  A  Y  D     G  L  M     A  G  L     G  A  S  G     S  G  T     F  T  T
1191  GTGAAGAAGC CAGCGTACGA TGGCCTGATG GCGGGTCTTG GAGCAAGCGG CTCCGGCACC ACAACGACCA
       T  T  T     S  T  T     T  G  G     T  D  P  T     G  V  A     Q  K  W     G  Q  C  G
1261  CTACTACTAC TTCTACTACG ACAGGAGGTA CGGAGCCCTAC TGGAGTCGCT CAGAAATGGG GACAGTGTGG
       G  I  G     W  T  G     P  T  T  C     V  S  G     T  T  C     Q  K  L  N     D  W  Y
1331  CGGTATTGGC TGGACCGGGC CAACAACTTG TGTCAGTGGT ACCACTTGCC AAAAGCTGAA TGACTGGTAC
       S  Q  C     L  *
1401  TCACAGTGCC TGTAA
```

Fig. 1B

XYLANASE VARIANTS AND POLYNUCLEOTIDES ENCODING SAME

CROSS-REFERENCE TO RELATED APPLICATIONS

This application is a 35 U.S.C. §371 national application of PCT/US2014/040148 filed May 30, 2014, which claims priority or the benefit under 35 U.S.C. §119 of U.S. provisional application No. 61/831,278 filed Jun. 5, 2013, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to xylanase variants, polynucleotides encoding the variants, methods of producing the variants, and methods of using the variants.

Description of the Related Art

Lignocellulose, the world's largest renewable biomass resource, is composed mainly of lignin, cellulose, and hemicellulose, of which a large part of the latter is xylan. Xylan is a polysaccharide formed from 1,4-β-glycoside-linked D-xylopyranoses. Xylanases (e.g., endo-1,4-beta-xylanase, EC 3.2.1.8) hydrolyze internal β-1,4-xylosidic linkages in xylan to produce smaller molecular weight xylose and xylo-oligomers.

Cellulose is a polymer of the simple glucose covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose. Once the cellulose is converted to glucose, the glucose can be fermented by yeast into ethanol.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

There is a need in the art for xylanases with increased thermostability as a component of enzyme compositions for use in the degradation of lignocellulose at high temperatures.

The present invention provides xylanase variants with increased thermostability.

SUMMARY OF THE INVENTION

The present invention relates to isolated xylanase variants, comprising a substitution at one or more (e.g., several) positions corresponding to positions 82, 87, 88, 98, 111, 154, 211, 213, 218, 238, 246, 278, 294, 332, 342, and 351 of the mature polypeptide of SEQ ID NO: 2, wherein the variants have xylanase activity.

The present invention also relates to isolated polynucleotides encoding the variants; nucleic acid constructs, vectors, and host cells comprising the polynucleotides; and methods of producing the variants.

The present invention also relates to processes for degrading a cellulosic or xylan-containing material, comprising: treating the cellulosic or xylan-containing material with an enzyme composition comprising a xylanase variant of the present invention. In one aspect, the processes further comprise recovering the degraded cellulosic or xylan-containing material.

The present invention also relates to processes of producing a fermentation product, comprising: (a) saccharifying a cellulosic or xylan-containing material with an enzyme composition comprising a xylanase variant of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition which comprises a xylanase variant of the present invention. In one aspect, the fermenting of the cellulosic or xylan-containing material produces a fermentation product. In another aspect, the processes further comprise recovering the fermentation product from the fermentation.

BRIEF DESCRIPTION OF THE FIGURES

FIGS. 1A and 1B show the genomic DNA sequence (SEQ ID NO: 1) and the deduced amino acid sequence (SEQ ID NO: 2) of an *Aspergillus fumigatus* gene encoding a GH10 xylanase.

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, J. Bacteriol. 180: 243-249. One unit of alpha-glucuronidase equals the amount of enzyme capable of releasing 1 µmole of glucuronic or 4-O-methylglucuronic acid per minute at pH 5, 40° C.

Auxiliary Activity 9: The term "Auxiliary Activity 9" or "AA9" means a polypeptide classified as a lytic polysaccharide monooxygenase (Quinlan et al., 2011, *Proc. Natl. Acad. Sci.* USA 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 µmole of p-nitrophenolate anion produced per minute at 40° C., pH 5 from 1 mM p-nitrophenyl-beta-D-xyloside in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman NO filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is *arundo*, bagasse, bamboo, corn cob, corn fiber, corn stover, *miscanthus*, rice straw, switchgrass, or wheat straw.

In another embodiment, the cellulosic material is aspen, *eucalyptus*, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Endoglucanase: The term "endoglucanase" means a 4-(1, 3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). Endoglucanase activity can also be determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 µmole of p-nitrophenolate anion per minute at pH 5, 25° C.

Fragment: The term "fragment" means a polypeptide having one or more (e.g., several) amino acids absent from the amino and/or carboxyl terminus of the mature polypeptide thereof, wherein the fragment has xylanase activity. In one aspect, a fragment contains at least 85% of the amino acid residues, e.g., at least 90% of the amino acid residues or at least 95% of the amino acid residues of the mature polypeptide of a xylanase.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40-80° C., e.g., 50° C., 55° C., 60° C., 65° C., or 70° C., and a suitable pH such as 4-9, e.g., 5.0, 5.5, 6.0, 6.5, or 7.0.

High stringency conditions: The term "high stringency conditions" means for probes of at least 100 nucleotides in length, prehybridization and hybridization at 42° C. in 5×SSPE, 0.3% SDS, 200 μg/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such an improved property includes, but is not limited to, increased thermostability.

Increased thermostability: The term "increased thermostability" means a higher retention of xylanase activity of a xylanase variant after a period of incubation at a temperature relative to the parent. The increased thermostability of the variant relative to the parent can be assessed, for example, under conditions of one or more (e.g., several) temperatures. For example, the one or more (e.g., several) temperatures can be any temperature or temperatures in the range of 45-95° C., e.g., 45, 50, 55, 60, 65, 70, 75, 80, 85, or 95° C. (or in between, e.g., 73° C.) at one or more (e.g., several) pHs in the range of 3 to 9, e.g., 3.0, 3.5, 4.0, 4.5, 5.0, 5.5, 6.0, 6.5, 7.0, 7.5, 8.0, 8.5, or 9.0 (or in between) for a suitable period (time) of incubation, e.g., 1 minute, 5 minutes, 10 minutes, 15 minutes, 20 minutes, 25 minutes, 30 minutes, 45 minutes, or 60 minutes (or in between, e.g., 23 minutes, 37 minutes, etc.), such that the variant retains residual activity. However, longer periods of incubation can also be used. The term "increased thermostability" can be used interchangeably with "improved thermostability".

The increased thermostability of the variant relative to the parent can be determined by differential scanning calorimetry (DSC) using methods standard in the art (see, for example, Sturtevant, 1987, *Annual Review of Physical Chemistry* 38: 463-488; Example 9). The increased thermostability of the variant relative to the parent can also be determined using protein thermal unfolding analysis (see, for example, Example 10 herein). The increased thermostability of the variant relative to the parent can also be determined using any enzyme assay known in the art for xylanases having xylanase activity to measure residual activity after a temperature treatment. See for example, WO 2005/074647, WO 2005/074656, WO 2007/089290, WO 2008/148131, WO 2008/151043, WO 2009/085859, WO 2009/085864, WO 2009/085868, WO 2009/085935, and WO 2010/065830, which are incorporated herein by reference. Alternatively, the increased thermostability of the variant relative to the parent can be determined using any application assay for the variant where the performance of the variant is compared to the parent. For example, the application assays described in Example 5 can be used.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5×SSPE, 0.3% SDS, 200 μg/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 397 of SEQ ID NO: 2 based on the SignalP 3.0 program (Bendtsen et al., 2004, *J. Mol. Biol.* 340: 783-795) that predicts amino acids 1 to 19 of SEQ ID NO: 2 are a signal peptide. In another aspect, the mature polypeptide is amino acids 18 to 364 of SEQ ID NO: 4 based on the SignalP program that predicts amino acids 1 to 17 of SEQ ID NO: 4 are a signal peptide. In another aspect, the mature polypeptide is amino acids 20 to 323 of SEQ ID NO: 6 based on the SignalP program that predicts amino acids 1 to 19 of SEQ ID NO: 6 are a signal peptide. In another aspect, the mature polypeptide is amino acids 20 to 369 of SEQ ID NO: 8 based on the SignalP program that predicts amino acids 1 to 19 of SEQ ID NO: 8 are a signal peptide. In another aspect, the mature polypeptide is amino acids 19 to 414 of SEQ ID NO: 10 based on the SignalP program that predicts amino acids 1 to 18 of SEQ ID NO: 10 are a signal peptide. In another aspect, the mature polypeptide is amino acids 24 to 403 of SEQ ID NO: 12 based on the SignalP program that predicts amino acids 1 to 23 of SEQ ID NO: 12 are a signal peptide. In another aspect, the mature polypeptide is amino acids 20 to 398 of SEQ ID NO: 14 based on the SignalP program that predicts amino acids 1 to 19 of SEQ ID NO: 14 are a signal peptide. In another aspect, the mature polypeptide is amino acids 20 to 407 of SEQ ID NO: 16 based on the SignalP program that predicts amino acids 1 to 19 of SEQ ID NO: 16 are a signal peptide. In another aspect, the mature polypeptide is amino acids 18 to 364 of SEQ ID NO: 18 based on the SignalP program that predicts amino acids 1 to 17 of SEQ ID NO: 18 are a signal peptide. In another aspect, the mature polypeptide is amino acids 17 to 389 of SEQ ID NO: 20 based on the SignalP program that predicts amino acids 1 to 16 of SEQ ID NO: 20 are a signal peptide. In another aspect, the mature polypeptide is amino acids 21 to 405 of SEQ ID NO: 22 based on the SignalP program that predicts amino acids 1 to 20 of SEQ ID NO: 22 are a signal peptide. In another aspect, the mature polypeptide is amino acids 21 to 406 of SEQ ID NO: 24 based on the SignalP program that predicts amino acids 1 to 20 of SEQ ID NO: 24 are a signal peptide. In another aspect, the mature polypeptide is amino acids 18 to 360 of SEQ ID NO: 26 based on the SignalP program that predicts amino acids 1 to 17 of SEQ ID NO: 26 are a signal peptide. In another aspect, the mature polypeptide is amino acids 19 to 376 of SEQ ID NO: 28 based on the SignalP program that predicts amino acids 1 to 18 of SEQ ID NO: 28 are a signal peptide. In another aspect, the mature polypeptide is amino acids 23 to 367 of SEQ ID NO: 30 based on the SignalP program that predicts amino acids 1 to 22 of SEQ ID NO: 30 are a signal peptide. In another aspect, the mature polypeptide is amino acids 19 to 326 of SEQ ID NO: 32 based on the SignalP program that predicts amino acids 1 to 18 of SEQ ID NO: 32 are a signal peptide. In another aspect, the mature polypeptide is amino acids 21 to 354 of SEQ ID NO: 34 based on the SignalP program that predicts amino acids 1 to 20 of SEQ ID NO: 34 are a signal peptide. In another aspect, the mature polypeptide is amino acids 18 to 355 of SEQ ID NO: 36 based on the SignalP program that predicts amino acids 1 to 17 of SEQ ID NO: 36 are a signal peptide. In another aspect, the mature polypeptide is amino acids 20 to 366 of SEQ ID NO: 38 based on the SignalP program that predicts amino acids 1 to 19 of SEQ ID NO: 38 are a signal peptide. In another aspect, the mature polypeptide is amino acids 18 to 381 of SEQ ID NO: 40 based on the SignalP program that predicts amino acids 1 to 17 of SEQ ID NO: 40 are a signal peptide. In another aspect, the mature polypeptide is amino acids 18 to 362 of SEQ ID NO: 42 based on the SignalP program that predicts amino acids 1 to 17 of SEQ ID NO: 42 are a signal peptide. In another aspect, the mature polypeptide is amino acids 18 to 413 of SEQ ID NO: 44 based on the SignalP program that predicts amino acids 1 to 17 of SEQ ID NO: 44 are a signal peptide. In another aspect, the mature polypeptide is amino acids 22 to 396 of SEQ ID NO: 46 based on the SignalP program that predicts amino acids 1 to 21 of SEQ ID NO: 46 are a signal peptide. In another aspect, the mature polypeptide is amino acids 23 to 408 of SEQ ID NO: 48 based on the SignalP program that predicts amino acids 1 to 22 of SEQ ID NO: 48 are a signal peptide. In another aspect, the mature polypeptide is amino acids 23 to 406 of SEQ ID NO: 50 based on the SignalP program that predicts amino acids 1 to 22 of SEQ ID NO: 50 are a signal peptide. In another aspect, the mature polypeptide is amino acids 17 to 347 of SEQ ID NO: 52 based on the SignalP program that predicts amino acids 1 to 16 of SEQ ID NO: 52 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having xylanase activity. In one aspect, the mature polypeptide coding sequence is nucleotides 388 to 1332 of SEQ ID NO: 1 based on the SignalP 3.0 program (Bendtsen et al., 2004, supra) that predicts nucleotides 107 to 1412 of SEQ ID NO: 1 encode a signal peptide. In another aspect, the mature polypeptide coding sequence is nucleotides 52 to 1145 of SEQ ID NO: 3 based on the SignalP program that predicts nucleotides 1 to 51 of SEQ ID NO: 3 encode a signal peptide. In another aspect, the mature polypeptide coding sequence is nucleotides 58 to 1400 of SEQ ID NO: 5 based on the SignalP program that predicts nucleotides 1 to 57 of SEQ ID NO: 5 encode a signal peptide. In another aspect, the mature polypeptide coding sequence is nucleotides 58 to 1107 of SEQ ID NO: 7 based on the SignalP program that predicts nucleotides 1 to 57 of SEQ ID NO: 7 encode a signal peptide. In another aspect, the mature polypeptide coding sequence is nucleotides 55 to 1242 of SEQ ID NO: 9 based on the SignalP program that predicts nucleotides 1 to 54 of SEQ ID NO: 9 encode a signal peptide. In another aspect, the mature polypeptide coding sequence is nucleotides 70 to 1384 of SEQ ID NO: 11 based on the SignalP program that predicts nucleotides 1 to 69 of SEQ ID NO: 11 encode a signal peptide. In another aspect, the mature polypeptide coding sequence is nucleotides 58 to 1194 of SEQ ID NO: 13 based on the SignalP program that predicts nucleotides 1 to 57 of SEQ ID NO: 13 encode a signal peptide. In another aspect, the mature polypeptide coding sequence is nucleotides 15 to 1439 of SEQ ID NO: 15 based on the SignalP program that predicts nucleotides 1 to 57 of SEQ ID NO: 15 encode a signal peptide. In another aspect, the mature polypeptide coding sequence is nucleotides 82 to 851 of SEQ ID NO: 17 based on the SignalP program that predicts nucleotides 1 to 81 of SEQ ID NO: 17 encode a signal peptide. In another aspect, the mature polypeptide coding sequence is nucleotides 49 to 1705 of SEQ ID NO: 19 based on the SignalP program that predicts nucleotides 1 to 48 of SEQ ID NO: 19 encode a signal peptide. In another aspect, the mature polypeptide coding sequence is nucleotides 124 to 1517 of SEQ ID NO: 21 based on the SignalP program that predicts nucleotides 1 to 123 of SEQ ID NO: 21 encode a signal peptide. In another aspect, the mature polypeptide coding sequence is nucleotides 61 to 1311 of SEQ ID NO: 23 based on the SignalP program that predicts nucleotides 1 to 60 of SEQ ID NO: 23 encode a signal peptide. In another aspect, the mature polypeptide coding sequence is nucleotides 52 to 1347 of SEQ ID NO: 25 based on the SignalP program that predicts nucleotides 1 to 51 of SEQ ID NO: 25 encode a signal peptide. In another aspect, the mature polypeptide coding sequence is nucleotides 55 to 1196 of SEQ ID NO: 27 based on the SignalP program that predicts nucleotides 1 to 54 of SEQ ID NO: 27 encode a signal peptide. In another aspect, the mature polypeptide coding sequence is nucleotides 67 to 1101 of SEQ ID NO: 29 based on the SignalP program that predicts nucleotides 1 to 66 of SEQ ID NO: 29 encode a signal peptide. In another aspect, the mature polypeptide coding sequence is nucleotides 55 to 1620 of SEQ ID NO: 31 based on the SignalP program that predicts nucleotides 1 to 54 of SEQ ID NO: 31 encode a signal peptide. In another aspect, the mature polypeptide coding sequence is nucleotides 61 to 1362 of SEQ ID NO: 33 based on the SignalP program that predicts nucleotides 1 to 60 of SEQ ID NO: 33 encode a signal peptide. In another aspect, the mature polypeptide coding sequence is nucleotides 52 to 1510 of SEQ ID NO: 35 based on the SignalP program that predicts nucleotides 1 to 51 of SEQ ID NO: 35 encode a signal peptide. In another aspect, the mature polypeptide coding sequence is nucleotides 58 to 1098 of SEQ ID NO: 37 based on the SignalP program that predicts nucleotides 1 to 57 of SEQ ID NO: 37 encode a signal peptide. In another aspect, the mature polypeptide coding sequence is nucleotides 52 to 1362 of SEQ ID NO: 39 based on the SignalP program that predicts nucleotides 1 to 51 of SEQ ID NO: 39 encode a signal peptide. In another aspect, the mature polypeptide coding sequence is nucleotides 52 to 1165 of SEQ ID NO: 41 based on the SignalP program that predicts nucleotides 1 to 51 of SEQ ID NO: 41 encode a signal peptide. In another aspect, the mature polypeptide coding sequence is nucleotides 52 to 1239 of SEQ ID NO: 43 based on the SignalP program that predicts nucleotides 1 to 51 of SEQ ID NO: 43 encode a signal peptide. In another aspect, the mature polypeptide coding sequence is nucleotides 125 to 1424 of SEQ ID NO: 45 based on the SignalP program that predicts nucleotides 1 to 124 of SEQ ID NO: 45 encode a signal peptide. In another aspect, the mature polypeptide coding sequence is nucleotides 116 to 1435 of SEQ ID NO: 47 based on the SignalP program that predicts nucleotides 1 to 115 of SEQ ID NO: 47 encode a signal peptide. In another aspect, the mature polypeptide coding sequence is nucleotides 67 to 1218 of SEQ ID NO: 49 based on the SignalP program that predicts nucleotides 1 to 66 of SEQ ID NO: 49 encode a signal peptide. In another aspect, the mature polypeptide coding sequence is nucleotides 49 to 1349 of SEQ ID NO: 51 based on the SignalP program that predicts nucleotides 1 to 48 of SEQ ID NO: 51 encode a signal peptide. The term "mature polypeptide coding sequence" herein shall be understood to include the cDNA sequence of the genomic DNA sequence or the genomic DNA sequence of the cDNA sequence.

Medium stringency conditions: The term "medium stringency conditions" means for probes of at least 100 nucleotides in length, prehybridization and hybridization at 42° C. in 5×SSPE, 0.3% SDS, 200 µg/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 µg/ml sheared and denatured salmon sperm DNA, and 35% formamide, following standard Southern blotting procedures for 12 to 24 hours. The carrier material is finally washed three times each for 15 minutes using 0.2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent xylanase: The term "parent" or "parent xylanase" means a xylanase to which an alteration, i.e., a substitution, insertion, and/or deletion, at one or more (e.g., several) positions, is made to produce the xylanase variants of the present invention. The parent may be a naturally occurring (wild-type) polypeptide or a variant or fragment thereof.

Polypeptide having cellulolytic enhancing activity: The term "polypeptide having cellulolytic enhancing activity" means an AA9 polypeptide that catalyzes the enhancement of the hydrolysis of a cellulosic material by enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40-80° C., e.g., 50° C., 55° C., 60° C., 65° C., or 70° C., and a suitable pH, such as 4-9, e.g., 4.5, 5.0, 5.5, 6.0, 6.5, 7.0, 7.5, 8.0, or 8.5, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes NS, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 02/095014) of cellulase protein loading is used as the source of the cellulolytic activity.

AA9 polypeptide enhancing activity can also be determined by incubating the AA9 polypeptide with 0.5% phosphoric acid swollen cellulose (PASO), 100 mM sodium acetate pH 5, 1 mM $MnSO_4$, 0.1% gallic acid, 0.025 mg/ml of *Aspergillus fumigatus* beta-glucosidase, and 0.01% TRITON® X100 for 24-96 hours at 40° C. followed by determination of the glucose released from the PASO.

AA9 polypeptide enhancing activity can also be determined according to WO 2013/028928 for high temperature compositions.

The AA9 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence, wherein the subsequence encodes a fragment having xylanase activity. In one aspect, a subsequence contains at least 85% of the nucleotides, e.g., at least 90% of the nucleotides or at least 95% of the nucleotides of the mature polypeptide coding sequence of a xylanase.

Variant: The term "variant" means a polypeptide having xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the xylanase activity of their parent xylanases.

Very high stringency conditions: The term "very high stringency conditions" means for probes of at least 100 nucleotides in length, prehybridization and hybridization at 42° C. in 5×SSPE, 0.3% SDS, 200 µg/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 µg/ml sheared and denatured salmon sperm DNA, and 25% formamide, following standard Southern blotting procedures for 12 to 24 hours. The carrier material is finally washed three times each for 15 minutes using 0.2×SSC, 0.2% SDS at 45° C.

Wild-type xylanase: The term "wild-type" xylanase means a xylanase naturally produced by a microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, *Interlaboratory testing of methods for assay of xylanase activity, Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6. Xylanase activity can also be determined with 0.83 mM 4-nitrophenyl 3-D-xylopyranoside as substrate in 50 mM sodium acetate pH 4.5 buffer at ambient temperature. The reaction is stopped and absorbance of released nitrophenol is changed by addition of $NaCO_3$ to a final concentration of 294 mM. The absorbance at 405 nm can be measured using a SPECTRAMAX® 340pc spectrophotometric plate reader (Molecular Devices, Sunnyvale, Calif., USA).

Conventions for Designation of Variants

For purposes of the present invention, the mature polypeptide disclosed in SEQ ID NO: 2 is used to determine the corresponding amino acid residue in another xylanase. The amino acid sequence of another xylanase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are a gap open penalty of 10, a gap extension penalty of 0.5, and the EBLOSUM62 (EMBOSS version of BLOSUM62) substitution matrix. Numbering of the amino acid positions is based on the full-length polypeptide (e.g., including the signal peptide) of SEQ ID NO: 2 wherein position 1 is the first amino acid of the signal peptide (i.e., Met) and position 20 is Ala of SEQ ID NO: 2.

Identification of the corresponding amino acid residue in another xylanase can be determined by an alignment of multiple polypeptide sequences using several computer programs including, but not limited to MUSCLE (multiple sequence comparison by log-expectation; version 3.5 or later; Edgar, 2004, *Nucleic Acids Research* 32: 1792-1797); MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When another xylanase has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the xylanase variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple Substitutions.

Variants comprising multiple substitutions are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Substitutions.

Where different substitutions can be introduced at a position, the different substitutions are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:

"Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to isolated xylanase variants, comprising a substitution at one or more (e.g., several) positions corresponding to positions 82, 87, 88, 98, 111, 154, 211, 213, 218, 238, 246, 278, 294, 332, 342, and 351 of the mature polypeptide of SEQ ID NO: 2, wherein the variants have xylanase activity.

Variants

In an embodiment, the variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, to the amino acid sequence of the parent xylanase.

In another embodiment, the variant has at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

In one aspect, the number of substitutions in the variants of the present invention is 1-16, e.g., 1, 2, 3, 4, 5, 6, 7, 8, 9, 10, 11, 12, 13, 14, 15, and 16 substitutions.

In another aspect, a variant comprises a substitution at one or more (e.g., several) positions corresponding to positions 82, 87, 88, 98, 111, 154, 211, 213, 218, 238, 246, 278, 294, 332, 342, and 351. In another aspect, a variant comprises a substitution at two positions corresponding to any of positions 82, 87, 88, 98, 111, 154, 211, 213, 218, 238, 246, 278, 294, 332, 342, and 351. In another aspect, a variant comprises a substitution at three positions corresponding to any of positions 82, 87, 88, 98, 111, 154, 211, 213, 218, 238, 246, 278, 294, 332, 342, and 351. In another aspect, a variant comprises a substitution at four positions corresponding to any of positions 82, 87, 88, 98, 111, 154, 211, 213, 218, 238, 246, 278, 294, 332, 342, and 351. In another aspect, a variant comprises a substitution at five positions corresponding to any of positions 82, 87, 88, 98, 111, 154, 211, 213, 218, 238, 246, 278, 294, 332, 342, and 351. In another aspect, a variant comprises a substitution at six positions corresponding to any of positions 82, 87, 88, 98, 111, 154, 211, 213, 218, 238, 246, 278, 294, 332, 342, and 351. In another aspect, a variant comprises a substitution at seven positions corresponding to any of positions 82, 87, 88, 98, 111, 154, 211, 213, 218, 238, 246, 278, 294, 332, 342, and 351. In another aspect, a variant comprises a substitution at eight positions corresponding to any of positions 82, 87, 88, 98, 111, 154, 211, 213, 218, 238, 246, 278, 294, 332, 342, and 351. In another aspect, a variant comprises a substitution at nine positions corresponding to any of positions 82, 87, 88, 98, 111, 154, 211, 213, 218, 238, 246, 278, 294, 332, 342, and 351. In another aspect, a variant comprises a substitution at ten positions corresponding to any of positions 82, 87, 88, 98, 111, 154, 211, 213, 218, 238, 246, 278, 294, 332, 342, and 351. In another aspect, a variant comprises a substitution at eleven positions corresponding to any of positions 82, 87, 88, 98, 111, 154, 211, 213, 218, 238, 246, 278, 294, 332, 342, and 351. In another aspect, a variant comprises a substitution at twelve positions corresponding to any of positions 82, 87, 88, 98, 111, 154, 211, 213, 218, 238, 246, 278, 294, 332, 342, and 351. In another aspect, a variant comprises a substitution at thirteen positions corresponding to any of positions 82, 87, 88, 98, 111, 154, 211, 213, 218, 238, 246, 278, 294, 332, 342, and 351. In another aspect, a variant comprises a substitution at fourteen positions corresponding to any of positions 82, 87, 88, 98, 111, 154, 211, 213, 218, 238, 246, 278, 294, 332, 342, and 351. In another aspect, a variant comprises a substitution at fifteen positions corresponding to any of positions 82, 87, 88, 98, 111, 154, 211, 213, 218, 238, 246, 278, 294, 332, 342, and 351. In another aspect, a variant comprises a substitution at each position corresponding to positions 82, 87, 88, 98, 111, 154, 211, 213, 218, 238, 246, 278, 294, 332, 342, and 351.

In another aspect, the variant comprises or consists of a substitution at a position corresponding to position 82. In another aspect, the amino acid at a position corresponding to position 82 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the substitution A82T of the mature polypeptide of SEQ ID NO: 2.

In another aspect, the variant comprises or consists of a substitution at a position corresponding to position 87. In another aspect, the amino acid at a position corresponding to position 87 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution V87I of the mature polypeptide of SEQ ID NO: 2.

In another aspect, the variant comprises or consists of a substitution at a position corresponding to position 88. In another aspect, the amino acid at a position corresponding to position 88 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ala. In another aspect, the variant comprises or consists of the substitution V88A of the mature polypeptide of SEQ ID NO: 2.

In another aspect, the variant comprises or consists of a substitution at a position corresponding to position 98. In another aspect, the amino acid at a position corresponding to position 98 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution M98L of the mature polypeptide of SEQ ID NO: 2.

In another aspect, the variant comprises or consists of a substitution at a position corresponding to position 111. In another aspect, the amino acid at a position corresponding to position 111 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ser. In another aspect, the variant comprises or consists of the substitution N111S of the mature polypeptide of SEQ ID NO: 2.

In another aspect, the variant comprises or consists of a substitution at a position corresponding to position 154. In another aspect, the amino acid at a position corresponding to position 154 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asp. In another aspect, the variant comprises or consists of the substitution E154D of the mature polypeptide of SEQ ID NO: 2.

In another aspect, the variant comprises or consists of a substitution at a position corresponding to position 211. In another aspect, the amino acid at a position corresponding to position 211 is substituted with Ala, Arg, Asn, Asp, Cys, Gln, Glu, Gly, His, Ile, Leu, Lys, Met, Phe, Pro, Ser, Thr, Trp, Tyr, or Val, preferably with Leu. In another aspect, the variant comprises or consists of the substitution M211L of the mature polypeptide of SEQ ID NO: 2.

In another aspect, the variant comprises or consists of a substitution at a position corresponding to position 213. In another aspect, the amino acid at a position corresponding to position 213 is substituted with Ala, Arg, Asn, Asp, Cys, Gln, Glu, Gly, His, Ile, Leu, Lys, Met, Phe, Pro, Ser, Thr, Trp, Tyr, or Val, preferably with Gln. In another aspect, the variant comprises or consists of the substitution K213Q of the mature polypeptide of SEQ ID NO: 2.

In another aspect, the variant comprises or consists of a substitution at a position corresponding to position 218. In another aspect, the amino acid at a position corresponding to position 218 is substituted with Ala, Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution K218R of the mature polypeptide of SEQ ID NO: 2.

In another aspect, the variant comprises or consists of a substitution at a position corresponding to position 238. In another aspect, the amino acid at a position corresponding to position 238 is substituted with Ala, Arg, Asn, Asp, Cys, Gln, Glu, Gly, His, Ile, Leu, Lys, Met, Phe, Pro, Ser, Thr, Trp, Tyr, or Val, preferably with Asn. In another aspect, the variant comprises or consists of the substitution D238N of the mature polypeptide of SEQ ID NO: 2.

In another aspect, the variant comprises or consists of a substitution at a position corresponding to position 246. In another aspect, the amino acid at a position corresponding to position 246 is substituted with Ala, Arg, Asn, Asp, Cys, Gln, Glu, Gly, His, Ile, Leu, Lys, Met, Phe, Pro, Ser, Thr, Trp, Tyr, or Val, preferably with Phe. In another aspect, the variant comprises or consists of the substitution Y246F of the mature polypeptide of SEQ ID NO: 2.

In another aspect, the variant comprises or consists of a substitution at a position corresponding to position 278. In another aspect, the amino acid at a position corresponding to position 278 is substituted with Ala, Arg, Asn, Asp, Cys, Gln, Glu, Gly, His, Ile, Leu, Lys, Met, Phe, Pro, Ser, Thr, Trp, Tyr, or Val, preferably with Tyr. In another aspect, the variant comprises or consists of the substitution F278Y of the mature polypeptide of SEQ ID NO: 2.

In another aspect, the variant comprises or consists of a substitution at a position corresponding to position 294. In another aspect, the amino acid at a position corresponding to position 294 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution V294I of the mature polypeptide of SEQ ID NO: 2.

In another aspect, the variant comprises or consists of a substitution at a position corresponding to position 332. In another aspect, the amino acid at a position corresponding to position 332 is substituted with Ala, Arg, Asn, Asp, Cys, Gln, Glu, Gly, His, Ile, Leu, Lys, Met, Phe, Pro, Ser, Thr, Trp, Tyr, or Val, preferably with Ile. In another aspect, the variant comprises or consists of the substitution L332I of the mature polypeptide of SEQ ID NO: 2.

In another aspect, the variant comprises or consists of a substitution at a position corresponding to position 342. In another aspect, the amino acid at a position corresponding to position 342 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the substitution G342T of the mature polypeptide of SEQ ID NO: 2.

In another aspect, the variant comprises or consists of a substitution at a position corresponding to position 351. In another aspect, the amino acid at a position corresponding to position 351 is substituted with Ala, Arg, Asn, Asp, Cys, Gln, Glu, Gly, His, Ile, Leu, Lys, Met, Phe, Pro, Ser, Thr, Trp, Tyr, or Val, preferably with Thr. In another aspect, the variant comprises or consists of the substitution S351T of the mature polypeptide of SEQ ID NO: 2.

In another aspect, the variant comprises or consists of one or more (e.g., several) substitutions selected from the group consisting of A82T, V87I, V88A, M98L, N111S, E154D, M211L, K213Q, K218R, D238N, Y246F, F278Y, V294I, L332I, G342T, and S351T; or the one or more (e.g., several) substitutions selected from the group consisting of A82T, V87I, V88A, M98L, N111S, E154D, M211L, K213Q, K218R, D238N, Y246F, F278Y, V294I, L332I, G342T, and S351T at positions corresponding to the mature polypeptide of SEQ ID NO: 2 in other xylanases described herein.

In each of the aspects below, the variant comprises or consists of the one or more (e.g., several) substitutions described below at positions corresponding to SEQ ID NO: 2 in other xylanases described herein.

In another aspect, the variant comprises or consists of the substitutions K218R+S351T of the mature polypeptide of SEQ ID NO: 2. In another aspect, the variant comprises or consists of the substitutions K218R+D238N of the mature polypeptide of SEQ ID NO: 2. In another aspect, the variant comprises or consists of the substitutions V87I+D238N of the mature polypeptide of SEQ ID NO: 2.

In another aspect, the variant comprises or consists of the substitutions F278Y+V294I+L332I of the mature polypeptide of SEQ ID NO: 2. In another aspect, the variant comprises or consists of the substitutions V87I+V88A+M98L of the mature polypeptide of SEQ ID NO: 2. In another aspect, the variant comprises or consists of the substitutions K218R+D238N+S351T of the mature polypeptide of SEQ ID NO: 2. In another aspect, the variant comprises or consists of the substitutions V87I+N111S+D238N of the mature polypeptide of SEQ ID NO: 2.

In another aspect, the variant comprises or consists of the substitutions E154D+M211L+Y246F+V294I of the mature polypeptide of SEQ ID NO: 2.

In another aspect, the variant comprises or consists of the substitutions E154D+M211L+K218R+Y246F+V294I of the mature polypeptide of SEQ ID NO: 2. In another aspect, the variant comprises or consists of the substitutions E154D+M211L+D238N+Y246F+V294I of the mature polypeptide of SEQ ID NO: 2.

In another aspect, the variant comprises or consists of the substitutions E154D+M211L+K218R+Y246F+V294I+S351T of the mature polypeptide of SEQ ID NO: 2. In another aspect, the variant comprises or consists of the substitutions E154D+M211L+K218R+D238N+Y246F+V294I of the mature polypeptide of SEQ ID NO: 2. In another aspect, the variant comprises or consists of the substitutions V87I+E154D+M211L+D238N+Y246F+V294I of the mature polypeptide of SEQ ID NO: 2.

In another aspect, the variant comprises or consists of the substitutions E154D+M211L+K218R+D238N+Y246F+V294I+S351T of the mature polypeptide of SEQ ID NO: 2. In another aspect, the variant comprises or consists of the substitutions V87I+N111S+E154D+M211L+D238N+Y246F+V294I of the mature polypeptide of SEQ ID NO: 2.

The variants may further comprise one or more additional alterations, e.g., substitutions, insertions, or deletions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, LeuNal, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for xylanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids in xylanases correspond to positions 22, 107, 194, and/or 196 of the mature polypeptide of SEQ ID NO: 2.

The variants may consist of at least 85% of the amino acid residues, e.g., at least 90% of the amino acid residues or at least 95% of the amino acid residues of the mature polypeptides of the corresponding parent xylanases.

In an embodiment, the variants have increased thermostability compared to their parent xylanases.

In one aspect, the thermostability of the variant relative to the parent is determined at pH 3.0 and 45° C. In another aspect, the thermostability of the variant relative to the parent is determined at pH 3.0 and 50° C. In another aspect, the thermostability of the variant relative to the parent is determined at pH 3.0 and 55°. In another aspect, the thermostability of the variant relative to the parent is determined at pH 3.0 and 60° C. In another aspect, the thermostability of the variant relative to the parent is determined at pH 3.0 and 65° C. In another aspect, the thermostability of the variant relative to the parent is determined at pH 3.0 and 70° C. In another aspect, the thermostability of the variant relative to the parent is determined at pH 3.0 and 73° C. In another aspect, the thermostability of the variant relative to the parent is determined at pH 3.0 and 75° C. In another aspect, the thermostability of the variant relative to the parent is determined at pH 3.0 and 80° C. In another aspect, the thermostability of the variant relative to the parent is determined at pH 3.0 and 85° C. In another aspect, the thermostability of the variant relative to the parent is determined at pH 3.0 and 90° C. In another aspect, the thermostability of the variant relative to the parent is determined at pH 3.0 and 95° C.

In another aspect, the thermostability of the variant relative to the parent is determined at pH 3.5 and 45° C. In another aspect, the thermostability of the variant relative to the parent is determined at pH 3.5 and 50° C. In another aspect, the thermostability of the variant relative to the parent is determined at pH 3.5 and 55° C. In another aspect, the thermostability of the variant relative to the parent is determined at pH 3.5 and 60° C. In another aspect, the thermostability of the variant relative to the parent is determined at pH 3.5 and 65° C. In another aspect, the thermostability of the variant relative to the parent is determined at pH 3.5 and 70° C. In another aspect, the thermostability of the variant relative to the parent is determined at pH 3.5 and 73° C. In another aspect, the thermostability of the variant relative to the parent is determined at pH 3.5 and 75° C. In another aspect, the thermostability of the variant relative to the parent is determined at pH 3.5 and 80° C. In another aspect, the thermostability of the variant relative to the parent is determined at pH 3.5 and 85° C. In another aspect, the thermostability of the variant relative to the parent is determined at pH 3.5 and 90°. In another aspect, the thermostability of the variant relative to the parent is determined at pH 3.5 and 95° C.

In another aspect, the thermostability of the variant relative to the parent is determined at pH 4.0 and 45° C. In another aspect, the thermostability of the variant relative to the parent is determined at pH 4.0 and 50° C. In another aspect, the thermostability of the variant relative to the parent is determined at pH 4.0 and 55° C. In another aspect, the thermostability of the variant relative to the parent is determined at pH 4.0 and 60° C. In another aspect, the thermostability of the variant relative to the parent is determined at pH 4.0 and 65° C. In another aspect, the thermostability of the variant relative to the parent is determined at pH 4.0 and 70° C. In another aspect, the thermostability of the variant relative to the parent is determined at pH 4.0 and 73° C. In another aspect, the thermostability of the variant relative to the parent is determined at pH 4.0 and 75° C. In another aspect, the thermostability of the variant relative to the parent is determined at pH 4.0 and 80° C. In another aspect, the thermostability of the variant relative to the parent is determined at pH 4.0 and 85° C. In another aspect, the thermostability of the variant relative to the parent is determined at pH 4.0 and 90° C. In another aspect, the thermostability of the variant relative to the parent is determined at pH 4.0 and 95° C.

In another aspect, the thermostability of the variant relative to the parent is determined at pH 4.5 and 45° C. In another aspect, the thermostability of the variant relative to the parent is determined at pH 4.5 and 50° C. In another aspect, the thermostability of the variant relative to the parent is determined at pH 4.5 and 55° C. In another aspect, the thermostability of the variant relative to the parent is determined at pH 4.5 and 60° C. In another aspect, the thermostability of the variant relative to the parent is determined at pH 4.5 and 65° C. In another aspect, the thermostability of the variant relative to the parent is determined at pH 4.5 and 70° C. In another aspect, the thermostability of the variant relative to the parent is determined at pH 4.5 and 73° C. In another aspect, the thermostability of the variant relative to the parent is determined at pH 4.5 and 75° C. In another aspect, the thermostability of the variant relative to the parent is determined at pH 4.5 and 80° C. In another aspect, the thermostability of the variant relative to the parent is determined at pH 4.5 and 85° C. In another aspect, the thermostability of the variant relative to the parent is determined at pH 4.5 and 90° C. In another aspect, the thermostability of the variant relative to the parent is determined at pH 4.5 and 95° C.

In another aspect, the thermostability of the variant relative to the parent is determined at pH 5.0 and 45° C. In another aspect, the thermostability of the variant relative to the parent is determined at pH 5.0 and 50° C. In another aspect, the thermostability of the variant relative to the parent is determined at pH 5.0 and 55° C. In another aspect, the thermostability of the variant relative to the parent is determined at pH 5.0 and 60° C. In another aspect, the thermostability of the variant relative to the parent is determined at pH 5.0 and 65° C. In another aspect, the thermostability of the variant relative to the parent is determined at pH 5.0 and 70° C. In another aspect, the thermostability of the variant relative to the parent is determined at pH 5.0 and 73° C. In another aspect, the thermostability of the variant relative to the parent is determined at pH 5.0 and 75° C. In another aspect, the thermostability of the variant relative to the parent is determined at pH 5.0 and 80° C. In another aspect, the thermostability of the variant relative to the parent is determined at pH 5.0 and 85° C. In another aspect, the thermostability of the variant relative to the parent is determined at pH 5.0 and 90° C. In another aspect, the thermostability of the variant relative to the parent is determined at pH 5.0 and 95° C.

In another aspect, the thermostability of the variant relative to the parent is determined at pH 5.5 and 45° C. In another aspect, the thermostability of the variant relative to the parent is determined at pH 5.5 and 50° C. In another aspect, the thermostability of the variant relative to the parent is determined at pH 5.5 and 55° C. In another aspect, the thermostability of the variant relative to the parent is determined at pH 5.5 and 60° C. In another aspect, the thermostability of the variant relative to the parent is determined at pH 5.5 and 65° C. In another aspect, the thermostability of the variant relative to the parent is determined at pH 5.5 and 70° C. In another aspect, the thermostability of the variant relative to the parent is determined at pH 5.5 and 73° C. In another aspect, the thermostability of the variant relative to the parent is determined at pH 5.5 and 75° C. In another aspect, the thermostability of the variant relative to the parent is determined at pH 5.5 and 80° C. In another aspect, the thermostability of the variant relative to the parent is determined at pH 5.5 and 85° C. In another aspect, the thermostability of the variant relative to the parent is determined at pH 5.5 and 90° C. In another aspect, the thermostability of the variant relative to the parent is determined at pH 5.5 and 95° C.

In another aspect, the thermostability of the variant relative to the parent is determined at pH 6.0 and 45° C. In another aspect, the thermostability of the variant relative to the parent is determined at pH 6.0 and 50° C. In another aspect, the thermostability of the variant relative to the parent is determined at pH 6.0 and 55° C. In another aspect, the thermostability of the variant relative to the parent is determined at pH 6.0 and 60° C. In another aspect, the thermostability of the variant relative to the parent is determined at pH 6.0 and 65° C. In another aspect, the thermostability of the variant relative to the parent is determined at pH 6.0 and 70° C. In another aspect, the thermostability of the variant relative to the parent is determined at pH 6.0 and 73° C. In another aspect, the thermostability of the variant relative to the parent is determined at pH 6.0 and 75° C. In another aspect, the thermostability of the variant relative to the parent is determined at pH 6.0 and 80° C. In another aspect, the thermostability of the variant relative to the parent is determined at pH 6.0 and 85° C. In another aspect, the thermostability of the variant relative to the parent is determined at pH 6.0 and 90° C. In another aspect, the thermostability of the variant relative to the parent is determined at pH 6.0 and 95° C.

In another aspect, the thermostability of the variant relative to the parent is determined at pH 6.5 and 45° C. In another aspect, the thermostability of the variant relative to the parent is determined at pH 6.5 and 50° C. In another aspect, the thermostability of the variant relative to the parent is determined at pH 6.5 and 55° C. In another aspect, the thermostability of the variant relative to the parent is determined at pH 6.5 and 60° C. In another aspect, the thermostability of the variant relative to the parent is determined at pH 6.5 and 65° C. In another aspect, the thermostability of the variant relative to the parent is determined at pH 6.5 and 70° C. In another aspect, the thermostability of the variant relative to the parent is determined at pH 6.5 and 73° C. In another aspect, the thermostability of the variant relative to the parent is determined at pH 6.5 and 75° C. In another aspect, the thermostability of the variant relative to the parent is determined at pH 6.5 and 80° C. In another aspect, the thermostability of the variant relative to the parent is determined at pH 6.5 and 85° C. In another aspect, the thermostability of the variant relative to the parent is determined at pH 6.5 and 90° C. In another aspect, the thermostability of the variant relative to the parent is determined at pH 6.5 and 95° C.

In another aspect, the thermostability of the variant relative to the parent is determined at pH 7.0 and 45° C. In another aspect, the thermostability of the variant relative to the parent is determined at pH 7.0 and 50° C. In another aspect, the thermostability of the variant relative to the parent is determined at pH 7.0 and 55° C. In another aspect, the thermostability of the variant relative to the parent is determined at pH 7.0 and 60° C. In another aspect, the thermostability of the variant relative to the parent is determined at pH 7.0 and 65° C. In another aspect, the thermostability of the variant relative to the parent is determined at pH 7.0 and 70° C. In another aspect, the thermostability of the variant relative to the parent is determined at pH 7.0 and 73° C. In another aspect, the thermostability of the variant relative to the parent is determined at pH 7.0 and 75° C. In another aspect, the thermostability of the variant relative to the parent is determined at pH 7.0 and 80° C. In another aspect, the thermostability of the variant relative to the parent is determined at pH 7.0 and 85° C. In another aspect, the thermostability of the variant relative to the parent is determined at pH 7.0 and 90° C. In another aspect, the thermostability of the variant relative to the parent is determined at pH 7.0 and 95° C.

In another aspect, the thermostability of the variant relative to the parent is determined at pH 7.5 and 45° C. In another aspect, the thermostability of the variant relative to the parent is determined at pH 7.5 and 50° C. In another aspect, the thermostability of the variant relative to the parent is determined at pH 7.5 and 55° C. In another aspect, the thermostability of the variant relative to the parent is determined at pH 7.5 and 60° C. In another aspect, the thermostability of the variant relative to the parent is determined at pH 7.5 and 65° C. In another aspect, the thermostability of the variant relative to the parent is determined at pH 7.5 and 70° C. In another aspect, the thermostability of the variant relative to the parent is determined at pH 7.5 and 73° C. In another aspect, the thermostability of the variant relative to the parent is determined at pH 7.5 and 75° C. In another aspect, the thermostability of the variant relative to the parent is determined at pH 7.5 and 80° C. In another aspect, the thermostability of the variant relative to the parent is determined at pH 7.5 and 85° C. In another aspect, the thermostability of the variant relative to the parent is determined at pH 7.5 and 90° C. In another aspect, the thermostability of the variant relative to the parent is determined at pH 7.5 and 95° C.

In another aspect, the thermostability of the variant relative to the parent is determined at pH 8.0 and 45° C. In another aspect, the thermostability of the variant relative to the parent is determined at pH 8.0 and 50° C. In another aspect, the thermostability of the variant relative to the parent is determined at pH 8.0 and 55° C. In another aspect, the thermostability of the variant relative to the parent is determined at pH 8.0 and 60° C. In another aspect, the thermostability of the variant relative to the parent is determined at pH 8.0 and 65° C. In another aspect, the thermostability of the variant relative to the parent is determined at pH 8.0 and 70° C. In another aspect, the thermostability of the variant relative to the parent is determined at pH 8.0 and 73° C. In another aspect, the thermostability of the variant relative to the parent is determined at pH 8.0 and 75° C. In another aspect, the thermostability of the variant relative to the parent is determined at pH 8.0 and 80° C. In another aspect, the thermostability of the variant relative to the parent is determined at pH 8.0 and 85° C. In another aspect, the thermostability of the variant relative to the parent is determined at pH 8.0 and 90° C. In another aspect, the thermostability of the variant relative to the parent is determined at pH 8.0 and 95° C.

In another aspect, the thermostability of the variant relative to the parent is determined at pH 8.5 and 45° C. In another aspect, the thermostability of the variant relative to the parent is determined at pH 8.5 and 50° C. In another aspect, the thermostability of the variant relative to the parent is determined at pH 8.5 and 55° C. In another aspect, the thermostability of the variant relative to the parent is determined at pH 8.5 and 60° C. In another aspect, the thermostability of the variant relative to the parent is determined at pH 8.5 and 65° C. In another aspect, the thermostability of the variant relative to the parent is determined at pH 8.5 and 70° C. In another aspect, the thermostability of the variant relative to the parent is determined at pH 8.5 and 73° C. In another aspect, the thermostability of the variant relative to the parent is determined at pH 8.5 and 75° C. In another aspect, the thermostability of the variant relative to the parent is determined at pH 8.5 and 80° C. In another aspect, the thermostability of the variant relative to the parent is determined at pH 8.5 and 85° C. In another aspect, the thermostability of the variant relative to the parent is determined at pH 8.5 and 90° C. In another aspect, the thermostability of the variant relative to the parent is determined at pH 8.5 and 95° C.

In another aspect, the thermostability of the variant relative to the parent is determined at pH 9.0 and 45° C. In another aspect, the thermostability of the variant relative to the parent is determined at pH 9.0 and 50° C. In another aspect, the thermostability of the variant relative to the parent is determined at pH 9.0 and 55° C. In another aspect, the thermostability of the variant relative to the parent is determined at pH 9.0 and 60° C. In another aspect, the thermostability of the variant relative to the parent is determined at pH 9.0 and 65° C. In another aspect, the thermostability of the variant relative to the parent is determined at pH 9.0 and 70° C. In another aspect, the thermostability of the variant relative to the parent is determined at pH 9.0 and 73° C. In another aspect, the thermostability of the variant relative to the parent is determined at pH 9.0 and 75° C. In another aspect, the thermostability of the variant relative to the parent is determined at pH 9.0 and 80° C. In another aspect, the thermostability of the variant relative to the parent is determined at pH 9.0 and 85° C. In another aspect, the thermostability of the variant relative to the parent is determined at pH 9.0 and 90° C. In another aspect, the thermostability of the variant relative to the parent is determined at pH 9.0 and 95° C.

In each of the aspects above, the thermostability of the variant relative to the parent can be determined by incubating the variant and parent for 1 minute. In each of the aspects above, the thermostability of the variant relative to the parent can be determined by incubating the variant and parent for 5 minutes. In each of the aspects above, the thermostability of the variant relative to the parent can be determined by incubating the variant and parent for 10 minutes. In each of the aspects above, the thermostability of the variant relative to the parent can be determined by incubating the variant and parent for 15 minutes. In each of the aspects above, the thermostability of the variant relative to the parent can be determined by incubating the variant and parent for 20 minutes. In each of the aspects above, the thermostability of the variant relative to the parent can be determined by incubating the variant and parent for 25 minutes. In each of the aspects above, the thermostability of the variant relative to the parent can be determined by incubating the variant and parent for 30 minutes. In each of the aspects above, the thermostability of the variant relative to the parent can be determined by incubating the variant and parent for 45 minutes. In each of the aspects above, the thermostability of the variant relative to the parent can be determined by incubating the variant and parent for 60 minutes. A time period longer than 60 minutes can also be used.

In one aspect, the thermostability of the variant having xylanase activity is increased at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to more thermostable than the parent.

Parent Xylanases

The parent xylanase may be any polypeptide having xylanase activity.

The parent xylanase may be (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51, or (ii) the full-length complement of (i); or (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51.

In one aspect, the parent has a sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have xylanase activity.

In one embodiment, the amino acid sequence of the parent differs by up to 10 amino acids, e.g., 1, 2, 3, 4, 5, 6, 7, 8, 9, or 10 from the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

In another embodiment, the parent comprises or consists of the amino acid sequence of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

In another embodiment, the parent comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

In another embodiment, the parent is a fragment containing at least 85% of the amino acid residues, e.g., at least 90% of the amino acid residues or at least 95% of the amino acid residues of the mature polypeptide of a xylanase.

In another embodiment, the parent is an allelic variant of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51, or the full-length complements thereof (Sambrook et al., 1989, *Molecular Cloning*, A Laboratory Manual, 2d edition, Cold Spring Harbor, N.Y.).

The polynucleotide of SEQ ID NO: 1, 3, 5, 7, 9, 11, 13, 15, 17, 19, 21, 23, 25, 27, 29, 31, 33, 35, 37, 39, 41, 43, 45, 47, 49, or 51, or subsequences thereof, as well as the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52, or fragments thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^3$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, 7, 9, 11, 13, 15, 17, 19, 21, 23, 25, 27, 29, 31, 33, 35, 37, 39, 41, 43, 45, 47, 49, or 51, or subsequences thereof, the carrier material is used in a Southern blot.

For purposes of the present invention, hybridization indicates that the polynucleotide hybridizes to a labeled nucleic acid probe corresponding to (i) SEQ ID NO: 1, 3, 5, 7, 9, 11, 13, 15, 17, 19, 21, 23, 25, 27, 29, 31, 33, 35, 37, 39, 41, 43, 45, 47, 49, or 51; (ii) the mature polypeptide coding sequence thereof; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51.

In another embodiment, the nucleic acid probe is a polynucleotide that encodes the polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52; the mature polypeptide thereof; or a fragment thereof.

In another embodiment, the nucleic acid probe is SEQ ID NO: 1, 3, 5, 7, 9, 11, 13, 15, 17, 19, 21, 23, 25, 27, 29, 31, 33, 35, 37, 39, 41, 43, 45, 47, 49, or 51.

In another aspect, the parent is encoded by a polynucleotide having a sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512;

Collins-Racie et al., 1995, *Biotechnology* 13: 982-987; Carter et al., 1989, *Proteins: Structure*, Function, and *Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one embodiment, the parent is secreted extracellularly.

The parent may be a bacterial xylanase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* xylanase, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* xylanase.

In one embodiment, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* xylanase.

The parent may be a fungal xylanase. For example, the parent may be a yeast xylanase such as a *Candida, Kluyveromyces, Pichia, Saccharomyces, Schizosaccharomyces*, or *Yarrowia* xylanase; or a filamentous fungal xylanase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* xylanase.

In another embodiment, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* xylanase.

In another embodiment, the parent is an *Acremonium cellulolyticus, Aspergillus aculeatus, Aspergillus awamori, Aspergillus foetidus, Aspergillus fumigatus, Aspergillus japonicus, Aspergillus lentulus, Aspergillus nidulans, Aspergillus niger, Aspergillus oryzae, Aspergillus terreus, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fennellia nivea, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium pinophilum, Penicillium purpurogenum, Phanerochaete chlysosporium, Talaromyces leycettanus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma iongibrachiatum, Trichoderma reesei*, or *Trichoderma viride* xylanase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a xylanase variant, comprising: (a) introducing into a parent xylanase a substitution at one or more (e.g., several) positions corresponding to positions 82, 87, 88, 98, 111, 154, 211, 213, 218, 238, 246, 278, 294, 332, 342, and 351 of the mature polypeptide of SEQ ID NO: 2, wherein the variant has xylanase activity; and optionally (b) recovering the variant.

The variants can be prepared using any mutagenesis procedure known in the art, such as site-directed mutagenesis, site-saturation mutagenesis, synthetic gene construction, semi-synthetic gene construction, shuffling, etc.

Site-directed mutagenesis is a technique in which one or more (e.g., several) mutations are introduced at one or more defined sites in a polynucleotide encoding the parent. Any site-directed mutagenesis procedure can be used in the present invention. There are many commercial kits available that can be used to prepare variants.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Site-saturation mutagenesis systematically replaces a polypeptide coding sequence with sequences encoding all 19 amino acids at one or more (e.g., several) specific positions (Parikh and Matsumura, 2005, *J. Mol. Biol.* 352: 621-628).

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to isolated polynucleotides encoding xylanase variants of the present invention.

Nucleic Acid Constructs

The present invention also relates to nucleic acid constructs comprising a polynucleotide encoding a xylanase variant of the present invention operably linked to one or more control sequences that direct the expression of the coding sequence in a suitable host cell under conditions compatible with the control sequences.

The polynucleotide may be manipulated in a variety of ways to provide for expression of a xylanase variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide recognized by a host cell for expression of a polynucleotide encoding a variant of the present invention. The promoter contains transcriptional control sequences that mediate the expression of the xylanase variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the xylanase variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the xylanase variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the xylanase variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a xylanase variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a xylanase variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the xylanase variant and the signal peptide sequence is positioned next to the N-terminus of the propeptide sequence.

It may also be desirable to add regulatory sequences that regulate expression of the xylanase variant relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked to the regulatory sequence.

Expression Vectors

The present invention also relates to recombinant expression vectors comprising a polynucleotide encoding a xylanase variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system. The vector preferably contains an element(s) that permits integration of the vector into the host cell's genome or autonomous replication of the vector in the cell independent of the genome.

For integration into the host cell genome, the vector may rely on the polynucleotide's sequence encoding the xylanase variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a xylanase variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a xylanase variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a xylanase variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Talaromyces emersonii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp. 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a xylanase variant, comprising: (a) cultivating a recombinant host cell of the present invention under conditions conducive for production of the variant; and optionally (b) recovering the variant.

The host cells are cultivated in a nutrient medium suitable for production of the xylanase variant using methods known in the art. For example, the cells may be cultivated by multi-well plates such as 24, 48, or 96 well plates, shake flask cultivation, or small-scale or large-scale fermentation (including continuous, batch, fed-batch, or solid state fermentations) in laboratory or industrial fermentors in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The xylanase variant may be detected using methods known in the art that are specific for the variant. These detection methods include, but are not limited to, use of specific antibodies, formation of an enzyme product, or disappearance of an enzyme substrate. For example, an enzyme assay, as described herein, may be used to determine the activity of the variant.

The xylanase variants may be recovered using methods known in the art. For example, the variant may be recovered from the nutrient medium by conventional procedures including, but not limited to, collection, centrifugation, filtration, extraction, spray-drying, evaporation, or precipitation. In one aspect, a whole fermentation broth comprising a variant of the present invention is recovered.

The xylanase variants may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the xylanase variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The fermentation broth formulations or cell compositions may further comprise multiple enzymatic activities, such as one or more (e.g., several) enzymes selected from the group consisting of a cellulase, a hemicellulase, an AA9 polypeptide, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Enzyme Compositions

The present invention also relates to compositions comprising a variant of the present invention. Preferably, the compositions are enriched in such a variant. The term "enriched" indicates that the xylanase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The present invention is also directed to the following processes for using the xylanase variants, or compositions thereof.

The present invention also relates to processes for degrading a cellulosic or xylan-containing material, comprising: treating the cellulosic or xylan-containing material with an enzyme composition comprising a xylanase variant of the present invention. In one aspect, the processes further comprise recovering the degraded or converted cellulosic or xylan-containing material. Soluble products of degradation or conversion of the cellulosic or xylan-containing material can be separated from insoluble cellulosic or xylan-containing material using a method known in the art such as, for example, centrifugation, filtration, or gravity settling.

The present invention also relates to processes of producing a fermentation product, comprising: (a) saccharifying a cellulosic or xylan-containing material with an enzyme composition comprising a xylanase variant of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition comprising a xylanase variant of the present invention. In one aspect, the fermenting of the cellulosic or xylan-containing material produces a fermentation product. In another aspect, the processes further comprise recovering the fermentation product from the fermentation.

The processes of the present invention can be used to saccharify the cellulosic or xylan-containing material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic or xylan-containing material typically involves pretreatment, enzymatic hydrolysis (saccharification), and fermentation.

The processing of the cellulosic or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic or xylan-containing material to fermentable sugars, e.g., glucose, cellobiose, and pentose monomers, and then ferment the fermentable sugars to ethanol. In SSF, the enzymatic hydrolysis of the cellulosic or xylan-containing material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan and Himmel, 1999, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic or xylan-containing material to fermentable sugars and to convert the fermentable sugars into a final product (Lynd et al., 2002, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic or xylan-containing material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or xylan-containing material is heated to disrupt the plant cell wall components, including lignin, hemicellulose, and cellulose to make the cellulose and other fractions, e.g., hemicellulose, accessible to enzymes. The cellulosic or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Application Publication No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, *Bioresource Technology* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic or xylan-containing material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt. % acid, e.g., 0.05 to 5 wt. % acid or 0.1 to 2 wt. % acid. The acid is contacted with the cellulosic or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or xylan-containing material is present during pretreatment in amounts preferably between 10-80 wt. %, e.g., 20-70 wt. % or 30-60 wt. %, such as around 40 wt. %. The pretreated cellulosic or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperature in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Saccharification.

In the hydrolysis step, also known as saccharification, the cellulosic or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition comprising a xylanase variant of the present invention. The enzymes of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 4.5 to about 5.5. The dry solids content is in the range of preferably about 5 to about 50 wt. %, e.g., about 10 to about 40 wt. % or about 20 to about 30 wt. %.

The enzyme compositions can comprise any protein useful in degrading the cellulosic or xylan-containing material.

In one aspect, the enzyme composition comprises or further comprises one or more (e.g., several) proteins selected from the group consisting of a cellulase, an AA9 polypeptide having cellulolytic enhancing activity, a hemicellulase, an esterase, an expansin, a ligninolytic enzyme, an oxidoreductase, a pectinase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. In another aspect, the oxidoreductase is selected from the group consisting of a catalase, a laccase, and a peroxidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises an AA9 polypeptide having cellulolytic enhancing activity. In another aspect, the enzyme composition comprises an endoglucanase and an AA9 polypeptide having cellulolytic enhancing activity. In another aspect, the enzyme composition comprises a cellobiohydrolase and an AA9 polypeptide having cellulolytic enhancing activity. In another aspect, the enzyme composition comprises a beta-glucosidase and an AA9 polypeptide having cellulolytic enhancing activity. In another aspect, the enzyme composition comprises an endoglucanase and a cellobiohydrolase. In another aspect, the enzyme composition comprises an endoglucanase and a cellobiohydrolase I, a cellobiohydrolase II, or a combination of a cellobiohydrolase I and a cellobiohydrolase II. In another aspect, the enzyme composition comprises an endoglucanase and a beta-glucosidase. In another aspect, the enzyme composition comprises a beta-glucosidase and a cellobiohydrolase. In another aspect, the enzyme composition comprises a beta-glucosidase and a cellobiohydrolase I, a cellobiohydrolase II, or a combination of a cellobiohydrolase I and a cellobiohydrolase II In another aspect, the enzyme composition comprises an endoglucanase, an AA9 polypeptide having cellulolytic enhancing activity, and a cellobiohydrolase. In another aspect, the enzyme composition comprises an endoglucanase, an AA9 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and an AA9 polypeptide having cellulolytic enhancing activity. In another aspect, the enzyme composition comprises a beta-glucosidase, an AA9 polypeptide having cellulolytic enhancing activity, and a cellobiohydrolase. In another aspect, the enzyme composition comprises a beta-glucosidase, an AA9 polypeptide having cellulolytic enhancing activity, and a cellobiohydrolase I, a cellobiohydrolase II, or a combination of a cellobiohydrolase I and a cellobiohydrolase II. In another aspect, the enzyme composition comprises an endoglucanase, a beta-glucosidase, and a cellobiohydrolase. In another aspect, the enzyme composition comprises an endoglucanase, a beta-glucosidase, and a cellobiohydrolase I, a cellobiohydrolase II, or a combination of a cellobiohydrolase I and a cellobiohydrolase II. In another aspect, the enzyme composition comprises an endoglucanase, a cellobiohydrolase, a beta-glucosidase, and an AA9 polypeptide having cellulolytic enhancing activity. In another aspect, the enzyme composition comprises an endoglucanase, a beta-glucosidase, an AA9 polypeptide having cellulolytic enhancing activity, and a cellobiohydrolase I, a cellobiohydrolase II, or a combination of a cellobiohydrolase I and a cellobiohydrolase II.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha- L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In an embodiment, the xylanase is a Family 10 xylanase. In another embodiment, the xylanase is a Family 11 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a ligninolytic enzyme. In an embodiment, the ligninolytic enzyme is a manganese peroxidase. In another embodiment, the ligninolytic enzyme is a lignin peroxidase. In another embodiment, the ligninolytic enzyme is a $H_2O_2$-producing enzyme. In another aspect, the enzyme composition comprises a pectinase. In another aspect, the enzyme composition comprises an oxidoreductase. In an embodiment, the oxidoreductase is a catalase. In another embodiment, the oxidoreductase is a laccase. In another embodiment, the oxidoreductase is a peroxidase. In another aspect, the enzyme composition comprises a protease. In another aspect, the enzyme composition comprises a swollenin.

In the processes of the present invention, the enzyme(s) can be added prior to or during saccharification, saccharification and fermentation, or fermentation.

One or more (e.g., several) components of the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme composition. It is understood herein that the recombinant proteins may be heterologous (e.g., foreign) and/or native to the host cell. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and xylanase variants depend on several factors including, but not limited to, the mixture of cellulolytic enzymes and/or hemicellulolytic enzymes, the cellulosic or xylan-containing material, the concentration of cellulosic or xylan-containing material, the pretreatment(s) of the cellulosic or xylan-containing material, temperature, time, pH, and inclusion of a fermenting organism (e.g., for Simultaneous Saccharification and Fermentation).

In one aspect, an effective amount of cellulolytic or hemicellulolytic enzyme to the cellulosic or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic or xylan-containing material.

In another aspect, an effective amount of a xylanase variant to the cellulosic or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or xylan-containing material.

In another aspect, an effective amount of a xylanase variant to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or xylan-containing material, e.g., AA9 polypeptides (collectively hereinafter "polypeptides having enzyme activity") can be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

A polypeptide having enzyme activity may be a bacterial polypeptide. For example, the polypeptide may be a Gram-positive bacterial polypeptide having enzyme activity, or a Gram-negative bacterial polypeptide having enzyme activity.

The polypeptide having enzyme activity may also be a fungal polypeptide, e.g., a yeast polypeptide having enzyme activity or a filamentous fungal polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host can be a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® CTec3 (Novozymes NS), CELLUCLAST™ (Novozymes A/S), NOVOZYM™ 188 (Novozymes A/S), SPEZYME™ CP (Genencor Int.), ACCELERASE™ TRIO (DuPont), FILTRASE® NL (DSM); METHAPLUS® S/L 100 (DSM), ROHAMENT™ 7069 W (Röhm GmbH), or ALTERNAFUEL® CMAX3™ (Dyadic International, Inc.). The cellulolytic enzyme preparation is added in an amount effective from about 0.001 to about 5.0 wt. % of solids, e.g., about 0.025 to about 4.0 wt. % of solids or about 0.005 to about 2.0 wt. % of solids.

Examples of bacterial endoglucanases that can be used in the processes of the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 2005/093050), *Erwinia carotovara* endoglucanase (Saarilahti et al., 1990, *Gene* 90: 9-14), *Thermobifida fusca* endoglucanase III (WO 2005/093050), and *Thermobifida fusca* endoglucanase V (WO 2005/093050).

Examples of fungal endoglucanases that can be used in the present invention, include, but are not limited to, *Trichoderma reesei* endoglucanase I (Penttila et al., 1986, *Gene* 45: 253-263, *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), *Aspergillus aculeatus* endoglucanase (Ooi et al., 1990, *Nucleic Acids Research* 18: 5884), *Aspergillus kawachfi* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank:AB003107), *Melanocarpus albomyces* endoglucanase (GenBank:MAL515703), *Neurospora crassa* endoglucanase (GenBank:XM_324477), *Humicola insolens* endoglucanase V, *Myceliophthora thermophila* CBS 117.65 endoglucanase, *Thermoascus aurantiacus* endoglucanase I (Gen Bank:AF487830), and *Trichoderma reesei* strain No. VTT-D-80133 endoglucanase (GenBank:M15665).

Examples of cellobiohydrolases useful in the present invention include, but are not limited to, *Aspergillus aculeatus* cellobiohydrolase II (WO 2011/059740), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (Gen Bank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 02/095014), *Penicillium brasilianum* IBT 20888 (WO 2007/019442 and WO 2010/088387), *Thielavia terrestris* (WO 2011/035029), and *Trichophaea saccata* (WO 2007/019442).

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

In the processes of the present invention, any AA9 polypeptide having cellulolytic enhancing activity can be used as a component of the enzyme composition.

Examples of AA9 polypeptides useful in the processes of the present invention include, but are not limited to, AA9 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, and WO 2009/085868), *Aspergillus fumigatus* (WO 2010/138754), *Penicillium pinophilum* (WO 2011/005867), *Thermoascus* sp. (WO 2011/039319), *Penicillium* sp. (WO 2011/041397), *Thermoascus crustaceous* (WO 2011/041504), *Aspergillus aculeatus* (WO 2012/125925), *Thermomyces lanuginosus* (WO 2012/113340, WO 2012/129699, and WO 2012/130964), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), and *Chaetomium thermophilum* (WO 2012/101206).

In one aspect, the AA9 polypeptide is used in the presence of a soluble activating divalent metal cation according to WO 2008/151043, e.g., manganese or copper.

In another aspect, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic or xylan-containing material such as pretreated corn stover (WO 2012/021394, WO 2012/021395, WO 2012/021396, WO 2012/021399, WO 2012/021400, WO 2012/021401, WO 2012/021408, and WO 2012/021410).

In one aspect, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/13095), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt:Q7SOW4), *Trichoderma reesei* (UniProtKB/TrEMBL:Q92458), *Talaromyces emersonii* (SwissProt:Q8X212), and *Talaromyces thermophilus* GH11 (WO 2012/13095).

Examples of acetylxylan esterases useful in the processes of the present invention include, but are not limited to, acetylxylan esterases from *Aspergillus aculeatus* (WO 2010/108918), *Chaetomium globosum* (U niProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:QOU HJ 1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt:A1 D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (Swiss Prot:QOCJ P9), *Humicola insolens* (WO 2010/014706), *Penicillium* aurantiogriseum (WO 2009/068565), *Talaromyces emersonii* (UniProt:Q8X211), and *Trichoderma reesei* (UniProt:Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, C A, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, N Y, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous.

Any suitable hydrolyzed cellulosic or xylan-containing material can be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter* saccharolyticum; and *Zymomonas*, such as *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In an aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

It is well known in the art that the organisms described above can also be used to produce other substances, as described herein.

The fermenting microorganism is typically added to the degraded cellulosic or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In one aspect, the fermentation product is an alcohol. It will be understood that the term "alcohol" encompasses a substance that contains one or more hydroxyl moieties. The alcohol can be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji at al., 2003, *World Journal of Microbiology and Biotechnology* 19(6): 595-603.

In another aspect, the fermentation product is an alkane. The alkane may be an unbranched or a branched alkane. The alkane can be, but is not limited to, pentane, hexane, heptane, octane, nonane, decane, undecane, or dodecane.

In another aspect, the fermentation product is a cycloalkane. The cycloalkane can be, but is not limited to, cyclopentane, cyclohexane, cycloheptane, or cyclooctane.

In another aspect, the fermentation product is an alkene. The alkene may be an unbranched or a branched alkene. The alkene can be, but is not limited to, pentene, hexene, heptene, or octene.

In another aspect, the fermentation product is an amino acid. The organic acid can be, but is not limited to, aspartic acid, glutamic acid, glycine, lysine, serine, or threonine. See, for example, Richard and Margaritis, 2004, *Biotechnology and Bioengineering* 87(4): 501-515.

In another aspect, the fermentation product is a gas. The gas can be, but is not limited to, methane, $H_2$, $CO_2$, or CO. See, for example, Kataoka at al., 1997, *Water Science and Technology* 36(6-7): 41-47; and Gunaseelan, 1997, *Biomass and Bioenergy* 13(1-2): 83-114.

In another aspect, the fermentation product is isoprene.

In another aspect, the fermentation product is a ketone. It will be understood that the term "ketone" encompasses a substance that contains one or more ketone moieties. The ketone can be, but is not limited to, acetone.

In another aspect, the fermentation product is an organic acid. The organic acid can be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Plants

The present invention also relates to isolated plants, e.g., a transgenic plant, plant part, or plant cell, comprising a polynucleotide of the present invention so as to express and produce a xylanase variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences (Sticklen, 2008, *Nature Reviews* 9: 433-443), is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and optionally (b) recovering the variant.

The present invention is further described by the following examples that should not be construed as limiting the scope of the invention.

EXAMPLES

Strain

*Aspergillus oryzae* strain MT3568 (U.S. Patent Application US 20110111453) was used as an expression host for the *Aspergillus fumigatus* GH10A xylanase and variants thereof.

Media and Reagents

AMG trace metals solution was composed of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4$—$H_2O$, 3 g of citric acid, and deionized water to 1 liter.

MDU2BP medium (pH 5.0) was composed of 135 g of maltose, 3 g of $MgSO_4.7H_2O$, 3 g of NaCl, 6 g of $K_2SO_4$, 36 g of $KH_2PO_4$, 21 g of yeast extract, 6 g of urea, 1.5 ml of AMG trace metals solution, and deionized water up to 1 liter.

PEG solution was composed of 6 g of polyethylene glycol 4000 (PEG 4000), 100 μl of 1 M Tris pH 7.5, 100 μl of 1 M $CaCl_2$, and deionized water to 10 ml.

2XYT agar plates were composed of 16 g of tryptone, 10 g of yeast extract, 5 g of NaCl, 15 g of Bacto agar, and deionized water to 1 liter.

2XYT+Amp agar plates were composed of 2XYT agar supplemented with 100 μg of ampicillin per ml.

Example 1: Construction of *Aspergillus fumigatus* GH10 Xylanase Gene Variants Variants of an *Aspergillus fumigatus* GH10 xylanase (SEQ ID NO: 1 for the DNA sequence and SEQ ID NO: 2 for the amino acid sequence) were constructed by performing single site-directed mutagenesis reactions on pHyGe001 (U.S. Pat. No. 7,960,160) using a QUIKCHANGE® II XL Site-Directed Mutagenesis Kit (Stratagene, La Jolla, Calif., USA). Two mutagenic primers were designed to insert the desired mutation. The PCR was composed of 12.5 ng of each primer, approximately 10 ng of template plasmid, 1× QUIKCHANGE® Reaction Buffer (Stratagene, La Jolla, Calif., USA), 1 μl of QUIKCHANGE® II XL dNTP mix (Stratagene, La Jolla, Calif., USA), and 1 μl of 2.5 U/μl Pfu ULTRA™ enzyme (Stratagene, La Jolla, Calif., USA) in a final volume of 50 μl. The amplification reaction was performed using an EPPENDORF® MASTERCYCLER® thermal cycler (Eppendorf, Hauppauge, N.Y., USA) programmed for a 95° C. hot start; 1 cycle at 95° C. for 30 seconds; 16 cycles each at 95° C. for 30 seconds, 55° C. for 1 minute, and 68° C. for 9 minutes; and a 4° C. hold. One μl of Dpn I was directly added to the amplification reaction and incubated at 37° C. for 1 hour. A 2 μl volume of the Dpn I digested reaction was used to transform *E. coli* ONE SHOT® TOP10 Ultracompetent Cells (Life Technologies, Grand Island, N.Y., USA) according to the manufacturer's instructions. *E. coli* transformants were selected on 2XYT+ Amp agar plates. Plasmid DNA from several of the resulting *E. coli* transformants was prepared using a BIOROBOT® 9600 (QIAGEN Inc., Valencia, Calif., USA). The insert was confirmed by DNA sequencing using a Model 3130xL Genetic Analyzer (Applied Biosystems, Life Technologies, Grand Island, N.Y., USA) and dye-terminator chemistry from a BIGDYE® Terminator v3.1 Cycle Sequencing Kit (Applied Biosystems, Life Technologies, Grand Island, N.Y., USA). For each reaction, one of the clones with the desired mutation was chosen. The primers used in these reactions are shown in Table 1.

TABLE 1

| Plasmid | Mutation | Parent Plasmid | Oligo ID | #Sequence |
|---|---|---|---|---|
| pMaWo135-13 | S351T | pHyGe001 | 1200232 | GTCCGTACCTCCTGTCGTAGTAGTAGTAGT AGTAGTGGTCGTTGTGG (SEQ ID NO: 53) |
|  |  |  | 1200231 | CCACAACGACCACTACTACTACTACTAC GACAGGAGGTACGGAC (SEQ ID NO: 54) |
| pMaWo140-13 | G342T | pHyGe001 | 1200242 | GTAGTAGTAGTGGTCGTTGTGGTAGTGGAG CCGCTTGCTCCAAGAC (SEQ ID NO: 55) |
|  |  |  | 1200241 | GTCTTGGAGCAAGCGGCTCCACTACCACAA CGACCACTACTACTAC (SEQ ID NO: 56) |
| ASPEFU_GH10-33 | L332I | pHyGe001 | 1200216 | GCTTGCTCCAAGACCCGCCATGATGCCATC GTACGCTGGCTTCTT (SEQ ID NO: 57) |
|  |  |  | 1200215 | AAGAAGCCAGCGTACGATGGCATCATGGC GGGTCTTGGAGCAAGC (SEQ ID NO: 58) |
| pMaWo134-10 | V294I | pHyGe001 | 1200230 | GTCGGTCCAGTCCCAGATAGTGATACCCAC GCAGCCAGTGGTGC (SEQ ID NO: 59) |
|  |  |  | 1200229 | GCACCACTGGCTGCGTGGGTATCACTATCT GGGACTGGACCGAC (SEQ ID NO: 60) |
| ASPEFU_GH10-17 | F278Y | pHyGe001 | 1200208 | CATGCTGCGGCCACGCCTTGGTAGTCAGTG GACTGCTGGGCCA (SEQ ID NO: 61) |
|  |  |  | 1200207 | TGGCCCAGCAGTCCACTGACTACCAAGGC GTGGCCGCAGCATG (SEQ ID NO: 62) |
| ASPEFU_GH10-9 | Y246F | pHyGe001 | 1200204 | CACCTCAACGCCGAGAGCAGTGAAGCCCTT CAAGACGGTCGTCAG (SEQ ID NO: 63) |
|  |  |  | 1200203 | CTGACGACCGTCTTGAAGGGCTTCACTGCT CTCGGCGTTGAGGTG (SEQ ID NO: 64) |
| pMaWo149-10 | D238N | pHyGe001 | 1200896 | GCCCTTCAAGACGGTCGTCAGATTCGATTG ACTCGGAGTGCTGCC (SEQ ID NO: 65) |
|  |  |  | 1200895 | GGCAGCACTCCGAGTCAATCGAATCTGACG ACCGTCTTGAAGGGC (SEQ ID NO: 66) |

TABLE 1-continued

| Plasmid | Mutation | Parent Plasmid | Oligo ID # | Sequence |
|---|---|---|---|---|
| pMaWo145-7 | K218R | pHyGe001 | 1200890 | GGAGGCCGACGCCGTCGATTCGCGCGCCG TAGGCCTTGATCA (SEQ ID NO: 67) |
| | | | 1200889 | TGATCAAGGCCTACGGCGCGCGAATCGAC GGCGTCGGCCTCC (SEQ ID NO: 68) |
| ASPEFU_GH10-37 | K213Q | pHyGe001 | 1200218 | TCGATCTTCGCGCCGTAGGCCTGGATCATC TTGACGATATTCTGCG (SEQ ID NO: 69) |
| | | | 1200217 | CGCAGAATATCGTCAAGATGATCCAGGCCT ACGGCGCGAAGATCGA (SEQ ID NO: 70) |
| pMaWo132-3 | M211L | pHyGe001 | 1200226 | CTTCGCGCCGTAGGCCTTGATCAGCTTGAC GATATTCTGCGCAGCA (SEQ ID NO: 71) |
| | | | 1200225 | TGCTGCGCAGAATATCGTCAAGCTGATCAA GGCCTACGGCGCGAAG (SEQ ID NO: 72) |
| pMaWo143-4 | E154D | pHyGe001 | 1200248 | CAGAGTTACGGAAAGTACCGTCGTCGTTCA GGGCTAGATTGACAGGC (SEQ ID NO: 73) |
| | | | 1200247 | GCCTGTCAATCTAGCCCTGAACGACGACGG TACTTTCCGTAACTCTG (SEQ ID NO: 74) |
| ASPEFU_GH10-45 | N111S | pHyGe001 | 1200222 | AGACAAGACGTTTACATACCCCAGCTCGGT AGCTGACTGTGCCAGAC (SEQ ID NO: 75) |
| | | | 1200221 | GTCTGGCACAGTCAGCTACCGAGCTGGGG TATGTAAACGTCTTGTCT (SEQ ID NO: 76) |
| ASPEFU_GH10-41 | V87I | pHyGe001 | 1200220 | CCATTCTTGTTCGCCAGATTGACGATGGCG TCTCCATTTGCGAACGA (SEQ ID NO: 77) |
| | | | 1200219 | TCGTTCGCAAATGGAGACGCCATCGTCAAT CTGGCGAACAAGAATGG (SEQ ID NO: 78) |
| pMaWo141-16 | A82T | pHyGe001 | 1200244 | GATTGACCACGGCGTCTCCATTAGTGAACG AAAAAGAATTCTGAGAAGG (SEQ ID NO: 79) |
| | | | 1200243 | CCTTCTCAGAATTCTTTTTCGTTCACTAATG GAGACGCCGTGGTCAATC (SEQ ID NO: 80) |

Example 2: Construction of *Aspergillus fumigatus* Family GH10 Xylanase Combinatorial Variants Ten variants (pTiaH0041-12, pTiaH0042-1, pTiaH0042-5, pTiaH0042-9, pTiaH0042-15, pLsBf55, pLsBf56, pLsBf59, pLsBf60, and pLsBf62) of the *Aspergillus fumigatus* GH10 xylanase were constructed via multi-site-directed mutagenesis using a QUIKCHANGE® Lightning Multi Site-Directed Mutagenesis Kit (Stratagene, La Jolla, Calif., USA). One mutagenic primer was designed for each desired mutation. One hundred ng of each primer (Table 2) were used in a PCR containing approximately 100 ng of template plasmid, 1× QUIKCHANGE® Lightning Multi Buffer (Stratagene, La Jolla, Calif., USA), 0.5 µl of QUIKSOLUTION® (Stratagene, La Jolla, Calif., USA), 1 µl of dNTP mix, and 1 µl of QUIKCHANGE® Lightning Multi enzyme blend (Stratagene, La Jolla, Calif., USA) in a final volume of 25 µl. Each amplification reaction was performed using an EPPENDORF® MASTERCYCLER® thermal cycler programmed for 1 cycle at 95° C. for 2 minutes; 30 cycles each at 95° C. for 20 seconds, 55° C. for 30 seconds, and 65° C. for 5 minutes; 1 cycle at 65° C. for 5 minutes, and a 4° C. hold. One µl of Dpn I was directly added to the amplification reaction and incubated at 37° C. for 5 minutes. A 1.5 µl volume of the Dpn I digested reaction was transformed into *E. coli* XL10-GOLD® Ultracompetent Cells (Stratagene, La Jolla, Calif., USA) according to the manufacturer's instructions. *E. coli* transformants were selected on 2XYT+Amp agar plates. Plasmid DNA from several of the resulting *E. coli* transformants was prepared using a BIOROBOT® 9600. The insert was confirmed by DNA sequencing using a Model 3130xL Genetic Analyzer and dye-terminator chemistry from the BIGDYE® Terminator v3.1 Cycle Sequencing Kit. One clone for each of the desired mutations was designated as each plasmid listed below.

TABLE 2

| Plasmid | Parent Mutations | Parent Plasmid | Oligo ID # | Sequence |
|---|---|---|---|---|
| pTiaH0041-12 | E154D, M211L, Y246F, V294I | pMAWO134 | 1200247 | GCCTGTCAATCTAGCCCTGAACGACGACGG TACTTTCCGTAACTCTG (SEQ ID NO: 81) |
| | | | 1200203 | CTGACGACCGTCTTGAAGGGCTTCACTGCT CTCGGCGTTGAGGTG (SEQ ID NO: 82) |
| | | | 1200229 | GCACCACTGGCTGCGTGGGTATCACTATCT GGGACTGGACCGAC (SEQ ID NO: 83) |
| | | | 1200225 | TGCTGCGCAGAATATCGTCAAGCTGATCAAG GCCTACGGCGCGAAG (SEQ ID NO: 84) |
| pTiaH0042-1 | E154D, M211L, | pTiaH0041-12 | 1200889 | TGATCAAGGCCTACGGCGCGCGAATCGACG GCGTCGGCCTCC (SEQ ID NO: 85) |

TABLE 2-continued

| Plasmid | Mutations | Parent Plasmid | Oligo ID | #Sequence |
|---|---|---|---|---|
| | Y246F, V294I, K218R | | 1200231 1200895 | CCACAACGACCACTACTACTACTACTACTAC GACAGGAGGTACGAC (SEQ ID NO: 86) GGCAGCACTCCGAGTCAATCGAATCTGACG ACCGTCTTGAAGGGC (SEQ ID NO: 87) |
| pTiaH0042-5 | E154D, M211L, Y246F, V294I, K218R, S351T | pTiaH0041-12 | 1200889 1200231 1200895 | TGATCAAGGCCTACGGCGCGCGAATCGACG GCGTCGGCCTCC (SEQ ID NO: 88) CCACAACGACCACTACTACTACTACTACTAC GACAGGAGGTACGAC (SEQ ID NO: 89) GGCAGCACTCCGAGTCAATCGAATCTGACG ACCGTCTTGAAGGGC (SEQ ID NO: 90) |
| pTiaH0042-9 | E154D, M211L, Y246F, V294I, K218R, D238N | pTiaH0041-12 | 1200889 1200231 1200895 | TGATCAAGGCCTACGGCGCGCGAATCGACG GCGTCGGCCTCC (SEQ ID NO: 91) CCACAACGACCACTACTACTACTACTACTAC GACAGGAGGTACGAC (SEQ ID NO: 92) GGCAGCACTCCGAGTCAATCGAATCTGACG ACCGTCTTGAAGGGC (SEQ ID NO: 93) |
| pTiaH0042-15 | E154D, M211L, Y246F, V294I, K218R, D238N, S351T | pTiaH0041-12 | 1200889 1200231 1200895 | TGATCAAGGCCTACGGCGCGCGAATCGACG GCGTCGGCCTCC (SEQ ID NO: 94) CCACAACGACCACTACTACTACTACTACTAC GACAGGAGGTACGAC (SEQ ID NO: 95) GGCAGCACTCCGAGTCAATCGAATCTGACG ACCGTCTTGAAGGGC (SEQ ID NO: 96) |
| pLsBf55 | E154D, M211L, Y246F, V294I, V87I, N111S, D238N | pTiaH0041-12 | 1200219 1200221 1200895 | TCGTTCGCAAATGGAGACGCCATCGTCAATCTGGC GAACAAGAATGG (SEQ ID NO: 97) GTCTGGCACAGTCAGCTACCGAGCTGGGGTATGT AAACGTCTTGTCT (SEQ ID NO: 98) GGCAGCACTCCGAGTCAATCGAATCTGACGACCGT CTTGAAGGGC (SEQ ID NO: 99) |
| pLsBf59 | E154D, M211L, Y246F, V294I, D238N | pTiaH0041-12 | 1200219 1200221 1200895 | TCGTTCGCAAATGGAGACGCCATCGTCAATCTGGC GAACAAGAATGG (SEQ ID NO: 100) GTCTGGCACAGTCAGCTACCGAGCTGGGGTATGT AAACGTCTTGTCT (SEQ ID NO: 101) GGCAGCACTCCGAGTCAATCGAATCTGACGACCGT CTTGAAGGGC (SEQ ID NO: 102) |
| pLsBf60 | E154D, M211L, Y246F, V294I, V87I, D238N | pTiaH0041-12 | 1200219 1200221 1200895 | TCGTTCGCAAATGGAGACGCCATCGTCAATCTGGC GAACAAGAATGG (SEQ ID NO: 103) GTCTGGCACAGTCAGCTACCGAGCTGGGGTATGT AAACGTCTTGTCT (SEQ ID NO: 104) GGCAGCACTCCGAGTCAATCGAATCTGACGACCGT CTTGAAGGGC (SEQ ID NO: 105) |
| pLsBf62 | F278Y, V294I, L332I | pHyGe001 | 1200207 1200215 1200229 1200213 | TGGCCCAGCAGTCCACTGACTACCAAGGCGTGGC CGCAGCATG (SEQ ID NO: 106) AAGAAGCCAGCGTACGATGGCATCATGGCGGGTC TTGGAGCAAGC (SEQ ID NO: 107) GCACCACTGGCTGCGTGGGTATCACTATCTGGGA CTGGACCGAC (SEQ ID NO: 108) TCCACTGACTTCCAAGGCGTGGTCGCAGCATGCGT TAGCACCACT (SEQ ID NO: 109) |
| pLsBf56 | V87I, V88A, M98L | GH10-41 | 1200201 1200211 | GCGAACAAGAATGGCCAGCTGCTGCGATGCCATA CTCTGGTCTGG (SEQ ID NO: 110) TTCGCAAATGGAGACGCCGTGGCCAATCTGGCGA ACAAGAATGGCC (SEQ ID NO: 111) |

For pTiaH0042-1, pTiaH0042-5, pTiaH0042-9, pTiaH0042-15, pLsBf55, pLsBf59, pLsBf60, and pLsBf62, not all mutagenic primers used in the reactions resulted in introduced mutations (as shown in Table 3 below).

TABLE 3

| Plasmid Name | Parent Plasmid | Planned Mutations | Introduced Mutations |
|---|---|---|---|
| pTiaH0042-1 | pTiaH0041-12 | K218R, D238N, S351T | K218R |
| pTiaH0042-5 | | | K218R, S351T |
| pTiaH0042-9 | | | K218R, D238N |
| pTiaH0042-15 | | | K218R, D238N, S351T |
| pLsBf55 | pTiaH0041-12 | V87I, N111S, D238N | V87I, N111S, D238N |
| pLsBf59 | | | D238N |
| pLsBf60 | | | V87I, D238N |
| pLsBf62 | pHyGe001 | F278Y, V294I, L332I | F278Y, V294I, L332I |

Example 3: Expression of the *Aspergillus fumigatus* GH10 Xylanase Variants in *Aspergillus oryzae* MT3568

*Aspergillus oryzae* MT3568 protoplasts were prepared according to the method of Christensen et al., 1988, *Bio/Technology* 6: 1419-1422, and transformed with 5 µg of each of the variant expression vectors described in Example 1 and Example 2, as well as pHyGe001 for the parent xylanase. The transformations yielded about 1-10 transformants for each vector. Up to four transformants for each transformation were isolated to individual PDA plates.

Confluent PDA plates of the transformants were washed with 8 ml of 0.01% TWEEN® 20 and inoculated separately into 1 ml of MDU2BP medium in sterile 24 well tissue culture plates and incubated at 34° C. Four days after incubation, 20 µl of harvested broth from each culture were analyzed using 8-16% Tris-Glycine SDS-PAGE gels (Invitrogen, Carlsbad, Calif., USA) according to the manufacturer's instructions. SDS-PAGE profiles of the cultures showed that several transformants had a new major band of approximately 45 kDa.

A confluent plate of one transformant for each transformation (grown on PDA) was washed with 8 ml of 0.01% TWEEN® 20 and inoculated into 125 ml glass baffled shake flasks containing 25 ml of MDU2BP medium and incubated at 34° C. with agitation at 225 rpm to generate broths for characterization of the variants. The flasks were harvested on day 4 and filtered using a 0.22 µm GP Express plus Membrane (Millipore, Bedford, Mass., USA).

Example 4: Measuring Thermostability of *Aspergillus fumigatus* Family GH10A Xylanase Variants Three ml of filtered broth for each culture from Example 3 were desalted into 50 mM sodium acetate pH 4.5 using ECONO-PAC® 10DG Desalting Columns (Bio-Rad Laboratories, Inc., Hercules, Calif., USA). Protein in the desalted broths was concentrated to an approximately 0.5 ml volume using VIVASPIN® 6 (5 kDa cutoff) ultrafilters (Argos Technology, Elgin, Ill., USA).

The concentrated broths were diluted to 1 mg/ml protein concentration or greater using 50 mM sodium acetate pH 4.5. Before carrying out the thermostability measurements, stocks were diluted to 1 mg/ml in 50 mM sodium acetate pH 4.5. Protein concentration was determined using absorbance at 280 nm, with a theoretical extinction coefficient of 2.3 for 1 mg/ml protein. Four 25 µl aliquots of each 1 mg/ml variant protein sample as well as three 25 µl aliquots of 1 mg/ml wild-type protein sample were added to THERMOWELL® tube strip PCR tubes (Corning, Corning, N.Y., USA). Two aliquots of the parent xylanase and each variant were kept on ice while the other two aliquots of the parent xylanase and each variant were heated in an EPPENDORF® MASTERCYCLER® ep gradient S thermocycler (Eppendorf Scientific, Inc., Westbury, N.Y., USA) for 20 minutes at 73° C. and then cooled to 4° C. before being placed on ice. All samples were then diluted with 75 µl of 50 mM sodium acetate pH 4.5.

Residual activity of the heated samples was then measured by determining the activity of the heated samples and the samples kept on ice using 4-nitrophenyl β-D-xylopyranoside as substrate. Twenty µl of each sample were added in duplicate, as well as one quadruplicate of 50 mM sodium acetate pH 4.5 buffer alone as a blank, to a 96 well PCR plate (Eppendorf, Westbury, N.Y., USA). Then 100 µl of 1 mM 4-nitrophenyl beta-D-xylopyranoside in 50 mM sodium acetate pH 4.5 were added to the 20 µl of each sample and mixed. The resulting mixtures were incubated for 30 minutes at ambient temperature. The reactions were stopped and absorbance of released nitrophenol was changed by addition of 50 µl of 1 M $NaCO_3$ to each well. The absorbance at 405 nm was then measured using a SPECTRAMAX® 340pc spectrophotometric plate reader (Molecular Devices, Sunnyvale, Calif., USA). Residual activity was then calculated by dividing the background subtracted absorbance at 405 nm from 4-nitrophenyl beta-D-xylopyranoside hydrolyzed by a heated sample by the background subtracted absorbance at 405 nm from 4-nitrophenyl beta-D-xylopyranoside hydrolyzed by a corresponding sample that was kept on ice. Residual activity of the GH10 xylanase variants was divided by the residual activity of the parent xylanase (pHyGe001) to determine relative stability. A value of greater than 1 indicates that the variant is more stable than the wild-type parent.

The results shown in Table 4 demonstrated an increase in thermostability by a higher residual activity for indicated variants compared to the parent enzyme.

TABLE 4

| Plasmid | Mutation(s) | Relative Stability |
|---|---|---|
| pHyGe001 | None | 1.00 |
| pMaWo135-13 | S351T | 1.07 |
| pMaWo140-13 | G342T | 1.04 |
| ASPEFU_GH10-33 | L332I | 1.11 |
| pMaWo134-10 | V294I | 1.061 |
| ASPEFU_GH10-17 | F278Y | 1.05 |
| ASPEFU_GH10-9 | Y246F | 1.09 |
| pMaWo149-10 | D238N | 1.04 |
| pMaWo145-7 | K218R | 1.07 |
| ASPEFU_GH10-37 | K213Q | 1.10 |
| pMaWo132-3 | M211L | 1.077 |

TABLE 4-continued

| Plasmid | Mutation(s) | Relative Stability |
|---|---|---|
| pMaWo143-4 | E154D | 1.108 |
| ASPEFU_GH10-45 | N111S | 1.20 |
| ASPEFU_GH10-41 | V87I | 1.43 |
| pMaWo141-16 | A82T | 1.05 |
| pLsBf55 | V87I, N111S, E154D, M211L, D238N, Y246F, V294I | 1.48 |
| pLsBf56 | V87I, V88A, M98L | 1.07 |
| pLsBf59 | E154D, M211L, D238N, Y246F, V294I | 1.21 |
| pLsBf60 | V87I, E154D, M211L, D238N, Y246F, V294I | 1.49 |
| pLsBf62 | F278Y, V294I, L332I | 1.32 |
| pTiaH0041-12 | E154D, M211L, Y246F, V294I | 1.24 |
| pTiaH0042-1 | E154D, M211L, K218R, Y246F, V294I | 1.24 |
| pTiaH0042-15 | E154D, M211L, K218R, D238N, Y246F, V294I, S351T | 1.26 |
| pTiaH0042-5 | E154D, M211L, K218R, Y246F, V294I, S351T | 1.28 |
| pTiaH0042-9 | E154D, M211L, K218R, D238N, Y246F, V294I | 1.29 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention is further defined by the following paragraphs:

Paragraph 1. A xylanase variant, comprising a substitution at one or more positions corresponding to positions 82, 87, 88, 98, 111, 154, 211, 213, 218, 238, 246, 278, 294, 332, 342, and 351 of the mature polypeptide of SEQ ID NO: 2, wherein the variant has xylanase activity and the variant has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the amino acid sequence of a parent xylanase.

Paragraph 2. The variant of paragraph 1, wherein the parent xylanase is selected from the group consisting of: (a) a polypeptide having at least 60% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52; (b) a polypeptide encoded by a polynucleotide that hybridizes under at least low stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51, or (ii) the full-length complement of (i); (c) a polypeptide encoded by a polynucleotide having at least 60% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51; and (d) a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52, which has xylanase activity.

Paragraph 3. The variant of paragraph 2, wherein the parent xylanase has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

Paragraph 4. The variant of paragraph 2, wherein the parent xylanase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51 or (ii) the full-length complement of (i).

Paragraph 5. The variant of paragraph 2, wherein the parent xylanase is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, 3, 5, 7, 9, 11, 13, 15, 17, 19, 21, 23, 25, 27, 29, 31, 33, 35, 37, 39, 41, 43, 45, 47, 49, or 51.

Paragraph 6. The variant of paragraph 2, wherein the parent xylanase comprises or consists of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

Paragraph 7. The variant of paragraph 2, wherein the parent xylanase is a fragment of the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52, wherein the fragment has xylanase activity.

Paragraph 8. The variant of any of paragraphs 1-7, which has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, or 52.

Paragraph 9. The variant of any of paragraphs 2-8, wherein the fragment consists of at least 85% of the amino acid residues, e.g., at least 90% of the amino acid residues or at least 95% of the amino acid residues of the mature polypeptide of the parent xylanase.

Paragraph 10. The variant of any of paragraphs 1-9, wherein the number of substitutions is 1-16, e.g., 1, 2, 3, 4, 5, 6, 7, 8, 9, 10, 11, 12, 13, 14, 15, and 16 substitutions.

Paragraph 11. The variant of any of paragraphs 1-10, which comprises a substitution at a position corresponding to position 82.

Paragraph 12. The variant of paragraph 11, wherein the substitution is Thr.

Paragraph 13. The variant of any of paragraphs 1-12, which comprises a substitution at a position corresponding to position 87.

Paragraph 14. The variant of paragraph 13, wherein the substitution is Ile.

Paragraph 15. The variant of any of paragraphs 1-14, which comprises a substitution at a position corresponding to position 88.

Paragraph 16. The variant of paragraph 15, wherein the substitution is Ala.

Paragraph 17. The variant of any of paragraphs 1-16, which comprises a substitution at a position corresponding to position 98.

Paragraph 18. The variant of paragraph 17, wherein the substitution is Leu.

Paragraph 19. The variant of any of paragraphs 1-18, which comprises a substitution at a position corresponding to position 111.

Paragraph 20. The variant of paragraph 19, wherein the substitution is Ser.

Paragraph 21. The variant of any of paragraphs 1-20, which comprises a substitution at a position corresponding to position 154.

Paragraph 22. The variant of paragraph 21, wherein the substitution is Asp.

Paragraph 23. The variant of any of paragraphs 1-22, which comprises a substitution at a position corresponding to position 211.

Paragraph 24. The variant of paragraph 23, wherein the substitution is Leu.

Paragraph 25. The variant of any of paragraphs 1-24, which comprises a substitution at a position corresponding to position 213.

Paragraph 26. The variant of paragraph 25, wherein the substitution is Gln.

Paragraph 27. The variant of any of paragraphs 1-26, which comprises a substitution at a position corresponding to position 218.

Paragraph 28. The variant of paragraph 27, wherein the substitution is Arg.

Paragraph 29. The variant of any of paragraphs 1-28, which comprises a substitution at a position corresponding to position 238.

Paragraph 30. The variant of paragraph 29, wherein the substitution is Asn.

Paragraph 31. The variant of any of paragraphs 1-30, which comprises a substitution at a position corresponding to position 246.

Paragraph 32. The variant of paragraph 31, wherein the substitution is Phe.

Paragraph 33. The variant of any of paragraphs 1-32, which comprises a substitution at a position corresponding to position 278.

Paragraph 34. The variant of paragraph 33, wherein the substitution is Tyr.

Paragraph 35. The variant of any of paragraphs 1-34, which comprises a substitution at a position corresponding to position 294.

Paragraph 36. The variant of paragraph 35, wherein the substitution is Ile.

Paragraph 37. The variant of any of paragraphs 1-36, which comprises a substitution at a position corresponding to position 332.

Paragraph 38. The variant of paragraph 37, wherein the substitution is Ile.

Paragraph 39. The variant of any of paragraphs 1-38, which comprises a substitution at a position corresponding to position 342.

Paragraph 40. The variant of paragraph 39, wherein the substitution is Thr.

Paragraph 41. The variant of any of paragraphs 1-40, which comprises a substitution at a position corresponding to position 351.

Paragraph 42. The variant of paragraph 41, wherein the substitution is Thr.

Paragraph 43. The variant of any of paragraphs 1-42, which comprises a substitution at two positions corresponding to any of positions 82, 87, 88, 98, 111, 154, 211, 213, 218, 238, 246, 278, 294, 332, 342, and 351.

Paragraph 44. The variant of any of paragraphs 1-42, which comprises a substitution at three positions corresponding to any of positions 82, 87, 88, 98, 111, 154, 211, 213, 218, 238, 246, 278, 294, 332, 342, and 351.

Paragraph 45. The variant of any of paragraphs 1-42, which comprises a substitution at four positions corresponding to any of positions 82, 87, 88, 98, 111, 154, 211, 213, 218, 238, 246, 278, 294, 332, 342, and 351.

Paragraph 46. The variant of any of paragraphs 1-42, which comprises a substitution at five positions corresponding to any of positions 82, 87, 88, 98, 111, 154, 211, 213, 218, 238, 246, 278, 294, 332, 342, and 351.

Paragraph 47. The variant of any of paragraphs 1-42, which comprises a substitution at six positions corresponding to any of positions 82, 87, 88, 98, 111, 154, 211, 213, 218, 238, 246, 278, 294, 332, 342, and 351.

Paragraph 48. The variant of any of paragraphs 1-42, which comprises a substitution at seven positions corresponding to any of positions 82, 87, 88, 98, 111, 154, 211, 213, 218, 238, 246, 278, 294, 332, 342, and 351.

Paragraph 49. The variant of any of paragraphs 1-42, which comprises a substitution at eight positions corresponding to any of positions 82, 87, 88, 98, 111, 154, 211, 213, 218, 238, 246, 278, 294, 332, 342, and 351.

Paragraph 50. The variant of any of paragraphs 1-42, which comprises a substitution at nine positions corresponding to any of positions 82, 87, 88, 98, 111, 154, 211, 213, 218, 238, 246, 278, 294, 332, 342, and 351.

Paragraph 51. The variant of any of paragraphs 1-42, which comprises a substitution at ten positions corresponding to any of positions 82, 87, 88, 98, 111, 154, 211, 213, 218, 238, 246, 278, 294, 332, 342, and 351.

Paragraph 52. The variant of any of paragraphs 1-42, which comprises a substitution at eleven positions corresponding to any of positions 82, 87, 88, 98, 111, 154, 211, 213, 218, 238, 246, 278, 294, 332, 342, and 351.

Paragraph 53. The variant of any of paragraphs 1-42, which comprises a substitution at twelve positions corresponding to any of positions 82, 87, 88, 98, 111, 154, 211, 213, 218, 238, 246, 278, 294, 332, 342, and 351.

Paragraph 54. The variant of any of paragraphs 1-42, which comprises a substitution at thirteen positions corresponding to any of positions 82, 87, 88, 98, 111, 154, 211, 213, 218, 238, 246, 278, 294, 332, 342, and 351.

Paragraph 55. The variant of any of paragraphs 1-42, which comprises a substitution at fourteen positions corresponding to any of positions 82, 87, 88, 98, 111, 154, 211, 213, 218, 238, 246, 278, 294, 332, 342, and 351.

Paragraph 56. The variant of any of paragraphs 1-42, which comprises a substitution at fifteen positions corresponding to any of positions 82, 87, 88, 98, 111, 154, 211, 213, 218, 238, 246, 278, 294, 332, 342, and 351.

Paragraph 57. The variant of any of paragraphs 1-42, which comprises a substitution at each position corresponding to positions 82, 87, 88, 98, 111, 154, 211, 213, 218, 238, 246, 278, 294, 332, 342, and 351.

Paragraph 58. The variant of any of paragraphs 1-57, which comprises one or more substitutions selected from the group consisting of A82T, V87I, V88A, M98L, N111S, E154D, M211L, K213Q, K218R, D238N, Y246F, F278Y, V294I, L332I, G342T, and S351T.

Paragraph 59. The variant of any of paragraphs 1-58, which comprises the substitutions K218R+S351T of the mature polypeptide of SEQ ID NO: 2.

Paragraph 60. The variant of any of paragraphs 1-59, which comprises the substitutions K218R+D238N of the mature polypeptide of SEQ ID NO: 2.

Paragraph 61. The variant of any of paragraphs 1-59, which comprises the substitutions V87I+D238N of the mature polypeptide of SEQ ID NO: 2.

Paragraph 62. The variant of any of paragraphs 1-59, which comprises the substitutions F278Y+V294I+L332I of the mature polypeptide of SEQ ID NO: 2.

Paragraph 63. The variant of any of paragraphs 1-59, which comprises the substitutions V87I+V88A+M98L of the mature polypeptide of SEQ ID NO: 2.

Paragraph 64. The variant of any of paragraphs 1-59, which comprises the substitutions K218R+D238N+S351T of the mature polypeptide of SEQ ID NO: 2.

Paragraph 65. The variant of any of paragraphs 1-59, which comprises the substitutions V87I+N111S+D238N of the mature polypeptide of SEQ ID NO: 2.

Paragraph 66. The variant of any of paragraphs 1-59, which comprises the substitutions E154D+M211L+Y246F+V294I of the mature polypeptide of SEQ ID NO: 2.

Paragraph 67. The variant of any of paragraphs 1-59, which comprises the substitutions E154D+M211L+K218R+Y246F+V294I of the mature polypeptide of SEQ ID NO: 2.

Paragraph 68. The variant of any of paragraphs 1-59, which comprises the E154D+M211L+D238N+Y246F+V294I of the mature polypeptide of SEQ ID NO: 2.

Paragraph 69. The variant of any of paragraphs 1-59, which comprises the substitutions E154D+M211L+K218R+Y246F+V294I+S351T of the mature polypeptide of SEQ ID NO: 2.

Paragraph 70. The variant of any of paragraphs 1-59, which comprises the substitutions E154D+M211L+K218R+D238N+Y246F+V294I of the mature polypeptide of SEQ ID NO: 2.

Paragraph 71. The variant of any of paragraphs 1-59, which comprises the substitutions V87I+E154D+M211L+D238N+Y246F+V294I of the mature polypeptide of SEQ ID NO: 2.

Paragraph 72. The variant of any of paragraphs 1-59, which comprises the substitutions E154D+M211L+K218R+D238N+Y246F+V294I+S351T of the mature polypeptide of SEQ ID NO: 2.

Paragraph 73. The variant of any of paragraphs 1-59, which comprises the substitutions V87I+N111S+E154D+M211L+D238N+Y246F+V294I of the mature polypeptide of SEQ ID NO: 2.

Paragraph 74. The variant of any of paragraphs 1-73, which has an increased thermostability of at least 1.01-fold, e.g., at least 1.05-fold, at least 1.1-fold, at least 1.2-fold, at least 1.3-fold, at least 1.4-fold, at least 1.5-fold, at least 1.8-fold, at least 2-fold, at least 5-fold, at least 10-fold, at least 15-fold, at least 20-fold, at least 25-fold, at least 30-fold, at least 50-fold, at least 75-fold, or at least 100-fold compared to the parent.

Paragraph 75. An isolated polynucleotide encoding the variant of any of paragraphs 1-74.

Paragraph 76. A nucleic acid construct comprising the polynucleotide of paragraph 75.

Paragraph 77. An expression vector comprising the polynucleotide of paragraph 75.

Paragraph 78. A recombinant host cell comprising the polynucleotide of paragraph 75.

Paragraph 79. A method of producing a xylanase variant, comprising: cultivating the host cell of paragraph 78 under conditions suitable for expression of the variant.

Paragraph 80. The method of paragraph 79, further comprising recovering the variant.

Paragraph 81. A transgenic plant, plant part or plant cell transformed with the polynucleotide of paragraph 75.

Paragraph 82. A method of producing a variant of any of paragraphs 1-74, comprising: cultivating a transgenic plant or a plant cell comprising a polynucleotide encoding the variant under conditions conducive for production of the variant.

Paragraph 83. The method of paragraph 82, further comprising recovering the variant.

Paragraph 84. A method for obtaining a xylanase variant, comprising introducing into a parent xylanase a substitution at one or more positions corresponding to positions 82, 87, 88, 98, 111, 154, 211, 213, 218, 238, 246, 278, 294, 332, 342, and 351 of the mature polypeptide of SEQ ID NO: 2, wherein the variant has xylanase activity; and recovering the variant.

Paragraph 85. A process for degrading a cellulosic or xylan-containing material, comprising: treating the cellulosic or xylan-containing material with an enzyme composition comprising the xylanase variant of any of paragraphs 1-74.

Paragraph 86. The process of paragraph 85, wherein the cellulosic or xylan-containing material is pretreated.

Paragraph 87. The process of paragraph 85 or 86, further comprising recovering the degraded cellulosic or xylan-containing material.

Paragraph 88. The process of any of paragraphs 85-87, wherein the enzyme composition comprises one or more enzymes selected from the group consisting of a cellulase, an AA9 polypeptide having cellulolytic enhancing activity, a hemicellulase, an esterase, an expansin, a laccase, a ligninolytic enzyme, a pectinase, an oxidoreductase, a protease, and a swollenin.

Paragraph 89. The process of paragraph 88, wherein the cellulase is one or more enzymes selected from the group consisting of an endoglucanase, a cellobiohydrolase, and a beta-glucosidase.

Paragraph 90. The process of paragraph 89, wherein the hemicellulase is one or more enzymes selected from the group consisting of a xylanase, an acetyxylan esterase, a feruloyl esterase, an arabinofuranosidase, a xylosidase, and a glucuronidase.

Paragraph 91. The process of any of paragraphs 85-90, wherein the degraded cellulosic or xylan-containing material is a sugar.

Paragraph 92. The process of paragraph 91, wherein the sugar is selected from the group consisting of glucose, xylose, mannose, galactose, and arabinose.

Paragraph 93. A process for producing a fermentation product, comprising: (a) saccharifying a cellulosic or xylan-containing material with an enzyme composition comprising the xylanase variant of any of paragraphs 1-74; (b) fermenting the saccharified cellulosic or xylan-containing material with one or more fermenting microorganisms to produce the fermentation product; and (c) recovering the fermentation product from the fermentation.

Paragraph 94. The process of paragraph 93, wherein the cellulosic or xylan-containing material is pretreated.

Paragraph 95. The process of paragraph 93 or 94, wherein the enzyme composition comprises one or more enzymes selected from the group consisting of a cellulase, an AA9 polypeptide having cellulolytic enhancing activity, a hemicellulase, an esterase, an expansin, a laccase, a ligninolytic enzyme, a pectinase, an oxidoreductase, a protease, and a swollenin.

Paragraph 96. The process of paragraph 95, wherein the cellulase is one or more enzymes selected from the group consisting of an endoglucanase, a cellobiohydrolase, and a beta-glucosidase.

Paragraph 97. The process of paragraph 95, wherein the hemicellulase is one or more enzymes selected from the group consisting of a xylanase, an acetyxylan esterase, a feruloyl esterase, an arabinofuranosidase, a xylosidase, and a glucuronidase.

Paragraph 98. The process of any of paragraphs 93-97, wherein steps (a) and (b) are performed simultaneously in a simultaneous saccharification and fermentation.

Paragraph 99. The process of any of paragraphs 93-98, wherein the fermentation product is an alcohol, an alkane, a cycloalkane, an alkene, an amino acid, a gas, isoprene, a ketone, an organic acid, or polyketide.

Paragraph 100. A process of fermenting a cellulosic or xylan-containing material, comprising: fermenting the cellulosic or xylan-containing material with one or more fermenting microorganisms, wherein the cellulosic or xylan-containing material is saccharified with an enzyme composition comprising the xylanase variant of any of paragraphs 1-74.

Paragraph 101. The process of paragraph 100, wherein the cellulosic or xylan-containing material is pretreated before saccharification.

Paragraph 102. The process of paragraph 100 or 101, wherein the enzyme composition comprises one or more enzymes selected from the group consisting of a cellulase, an AA9 polypeptide having cellulolytic enhancing activity, a hemicellulase, an esterase, an expansin, a laccase, a ligninolytic enzyme, a pectinase, an oxidoreductase, a protease, and a swollenin.

Paragraph 103. The process of paragraph 103, wherein the cellulase is one or more enzymes selected from the group consisting of an endoglucanase, a cellobiohydrolase, and a beta-glucosidase.

Paragraph 104. The process of paragraph 102, wherein the hemicellulase is one or more enzymes selected from the group consisting of a xylanase, an acetyxylan esterase, a feruloyl esterase, an arabinofuranosidase, a xylosidase, and a glucuronidase.

Paragraph 105. The process of any of paragraphs 100-104, wherein the fermenting of the cellulosic or xylan-containing material produces a fermentation product.

Paragraph 106. The process of paragraph 105, further comprising recovering the fermentation product from the fermentation.

Paragraph 107. The process of paragraph 105 or 106, wherein the fermentation product is an alcohol, an alkane, a cycloalkane, an alkene, an amino acid, a gas, isoprene, a ketone, an organic acid, or polyketide.

Paragraph 108. A composition comprising the variant of any of paragraphs 1-74.

Paragraph 109. A whole broth formulation or cell culture composition, comprising the variant of any of paragraphs 1-74.

What is claimed is:

1. A xylanase variant, comprising a substitution at one or more positions corresponding to positions 82, 87, 88, 98, 111, 154, 211, 213, 218, 238, 246, 278, 294, 332, 342, and 351 of the mature polypeptide of SEQ ID NO: 2, wherein the variant has xylanase activity and wherein the parent of the xylanase variant is selected from the group consisting of: (a) a polypeptide having at least 90% sequence identity to the mature polypeptide of SEQ ID NO: 2, 14, 20, or 22, or at least 95% sequence identity to the mature polypeptide of SEQ ID NO: 12; (b) a polypeptide encoded by a polynucleotide that hybridizes under very high stringency conditions with the full-length complement of the mature polypeptide coding sequence of SEQ ID NO: 1, 13, 19, or 21, wherein the very high stringency conditions are defined as prehybridization and hybridization at 42° C. in 5×SSPE, 0.3% SDS, 200 μg/ml sheared and denatured salmon sperm DNA, and 50% formamide, and washing three times each for 15 minutes using 0.2×SSC, 0.2% SDS at 70° C.; (c) a polypeptide encoded by a polynucleotide having at least 90% sequence identity to the mature polypeptide coding sequence of SEQ ID NO: 1, 13, 19, or 21, or at least 95% sequence identity to the mature polypeptide coding sequence of SEQ ID NO: 11; and (d) a fragment of the mature polypeptide of SEQ ID NO: 2, 12, 14, 20, or 22, which has xylanase activity.

2. The variant of claim 1, wherein the parent xylanase has at least 90% sequence identity to the mature polypeptide of SEQ ID NO: 2, 14, 20, or 22 or at least 95% sequence identity to the mature polypeptide of SEQ ID NO: 12.

3. The variant of claim 1, wherein the parent xylanase comprises the mature polypeptide of SEQ ID NO: 2, 12, 14, 20, or 22.

4. The variant of claim 1, wherein the parent xylanase is a fragment of the mature polypeptide of SEQ ID NO: 2, 12, 14, 20, or 22, wherein the fragment has xylanase activity.

5. The variant of claim 1, which has at least 90%, but less than 100%, sequence identity to the mature polypeptide of SEQ ID NO: 2, 14, 20, or 22 or at last 95%, but less than 100%, sequence identity to SEQ ID NO: 12.

6. The variant of claim 1, wherein the number of substitutions is 1-16 substitutions.

7. The variant of claim 1, which comprises one or more substitutions selected from the group consisting of A82T, V87I, V88A, M98L, N111S, E154D, M211L, K213Q, K218R, D238N, Y246F, F278Y, V294I, L332I, G342T, and S351T.

8. The variant of claim 1, which has an increased thermostability of at least 1.01-fold compared to the parent.

9. An isolated polynucleotide encoding the variant of claim 1.

10. A nucleic acid construct comprising the polynucleotide of claim 9.

11. An isolated recombinant host cell comprising the polynucleotide of claim 9.

12. A method of producing a xylanase variant, comprising: cultivating the recombinant host cell of claim 11 under conditions suitable for expression of the variant.

13. A composition, whole broth formulation, or cell culture composition, comprising the variant of claim 1.

14. The variant of claim 1, wherein the parent xylanase is a polypeptide having at least 95% sequence identity to the mature polypeptide of SEQ ID NO: 2, 12, 14, 20, or 22.

15. The variant of claim 1, wherein the parent xylanase is a polypeptide having at least 96% sequence identity to the mature polypeptide of SEQ ID NO: 2, 12, 14, 20, or 22.

16. The variant of claim 1, wherein the parent xylanase is a polypeptide having at least 97% sequence identity to the mature polypeptide of SEQ ID NO: 2, 12, 14, 20, or 22.

17. The variant of claim 1, wherein the parent xylanase is a polypeptide having at least 98% sequence identity to the mature polypeptide of SEQ ID NO: 2, 12, 14, 20, or 22.

18. The variant of claim 1, wherein the parent xylanase is a polypeptide having at least 99% sequence identity to the mature polypeptide of SEQ ID NO: 2, 12, 14, 20, or 22.

* * * * *

SEQUENCE LISTING

```
<160> NUMBER OF SEQ ID NOS: 111

<210> SEQ ID NO 1
<211> LENGTH: 1415
<212> TYPE: DNA
<213> ORGANISM: Aspergillus fumigatus

<400> SEQUENCE: 1
atggtccatc tatcttcatt ggcagcagcc ctggctgctc tgcctctgta tgtttaccca      60
ctcacgagag gaggaacagc tttgacattg ctatagtgta tatggagctg gcctgaacac     120
agcagccaaa gccaaaggac taaagtactt tggttccgcc acggacaatc cagagctcac     180
ggactctgcg tatgtcgcgc aactgagcaa caccgatgat tttggtcaaa tcacacccgg     240
aaactccatg aaggtttgct tacgtctgcc tccctggagc attgcctcaa aagctaattg     300
gttgttttgt ttggatagtg ggatgccacc gagccttctc agaattcttt ttcgttcgca     360
aatggagacg ccgtggtcaa tctggcgaac aagaatggcc agctgatgcg atgccatact     420
ctggtctggc acagtcagct accgaactgg ggtatgtaaa cgtcttgtct attctcaaat     480
actctctaac agttgacagt ctctagcggg tcatggacca atgcgaccct tttggcggcc     540
atgaagaatc atatcaccaa tgtggttact cactacaagg ggaagtgcta cgcctgggat     600
gttgtcaatg aaggtttgtt gctccatcta tcctcaatag ttcttttgaa actgacaagc     660
ctgtcaatct agccctgaac gaggacggta cttccgtaa ctctgtcttc taccagatca     720
```

-continued

```
tcggcccagc atacattcct attgcgttcg ccacggctgc tgccgcagat cccgacgtga      780
aactctacta caacgactac aacattgaat actcaggcgc caaagcgact gctgcgcaga      840
atatcgtcaa gatgatcaag gcctacggcg cgaagatcga cggcgtcggc ctccaggcac      900
actttatcgt cggcagcact ccgagtcaat cggatctgac gaccgtcttg aagggctaca      960
ctgctctcgg cgttgaggtg gcctataccg aacttgacat ccgcatgcag ctgccctcga     1020
ccgccgcaaa gctggcccag cagtccactg acttccaagg cgtggccgca gcatgcgtta     1080
gcaccactgg ctgcgtgggt gtcactatct gggactggac cgacaagtac tcctgggtcc     1140
ccagcgtgtt ccaaggctac ggcgcccat tgccttggga tgagaactat gtgaagaagc      1200
cagcgtacga tggcctgatg cgggtcttg gagcaagcgg ctccggcacc acaacgacca      1260
ctactactac ttctactacg acaggaggta cggaccctac tggagtcgct cagaaatggg     1320
gacagtgtgg cggtattggc tggaccgggc caacaacttg tgtcagtggt accacttgcc     1380
aaaagctgaa tgactggtac tcacagtgcc tgtaa                                1415
```

<210> SEQ ID NO 2
<211> LENGTH: 397
<212> TYPE: PRT
<213> ORGANISM: Aspergillus fumigatus
<400> SEQUENCE: 2

```
Met Val His Leu Ser Ser Leu Ala Ala Ala Leu Ala Ala Leu Pro Leu
1               5                  10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
    50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
        115                 120                 125

Asn His Ile Thr Asn Val Val Thr His Tyr Lys Gly Lys Cys Tyr Ala
    130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
    210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
```

|     |     |     | 245 |     |     |     | 250 |     |     |     | 255 |     |
| --- | --- | --- | --- | --- | --- | --- | --- | --- | --- | --- | --- | --- |
| Glu | Leu | Asp | Ile | Arg | Met | Gln | Leu | Pro | Ser | Thr | Ala | Ala | Lys | Leu | Ala |
|     |     |     | 260 |     |     |     | 265 |     |     |     | 270 |     |

Gln Gln Ser Thr Asp Phe Gln Gly Val Ala Ala Cys Val Ser Thr
            275                 280                 285

Thr Gly Cys Val Gly Val Thr Ile Trp Asp Trp Thr Asp Lys Tyr Ser
    290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
                325                 330                 335

Gly Ala Ser Gly Ser Gly Thr Thr Thr Thr Thr Thr Thr Ser Thr
            340                 345                 350

Thr Thr Gly Gly Thr Asp Pro Thr Gly Val Ala Gln Lys Trp Gly Gln
            355                 360                 365

Cys Gly Gly Ile Gly Trp Thr Gly Pro Thr Thr Cys Val Ser Gly Thr
    370                 375                 380

Thr Cys Gln Lys Leu Asn Asp Trp Tyr Ser Gln Cys Leu
385                 390                 395

<210> SEQ ID NO 3
<211> LENGTH: 1145
<212> TYPE: DNA
<213> ORGANISM: Aspergillus fumigatus

<400> SEQUENCE: 3

| atgcgtttct | cccttgccgc | caccgctctt | ctcgctggcc | tggccacggc | agcgccttcg | 60 |
| agcaacaaga | caacgtcaa  | tcttgataag | cttgctcggc | gtaatggcat | gctttggttc | 120 |
| ggcactgcag | ccgatatccc | tggtacctca | gaaacaaccg | acaagcctta | tctgagcatc | 180 |
| ctgcgcaagc | agttcggcga | aatgacaccc | gcaaacgcat | tgaaggtgag | ccagagtgat | 240 |
| agtacacctc | atctcgtgtc | ggcgctgacc | agacgatgtt | attcacatag | ttcatgtata | 300 |
| ccgagcccga | gcagaatgtc | ttcaacttca | ctcaagggga | ctacttcatg | gacttggccg | 360 |
| atcactatgg | tcacgccgtg | cgctgccata | acctcgtctg | ggccagccaa | gtgtccgact | 420 |
| gggtcacctc | caggaactgg | accgccacag | aactcaaaga | agtgatgaag | aaccacatat | 480 |
| tcaagaccgt | ccaacatttt | ggcaagcgct | gctacgcgtg | ggacgtcgtc | aatgaagcta | 540 |
| ttaatgggga | cgggaccttt | tcctccagtg | tgtggtacga | cacaattggc | gaggaatact | 600 |
| tctaccttgc | attccagtat | gcccaggaag | ccctggcgca | gattcacgcc | aaccaggtca | 660 |
| agctttacta | taacgactat | ggcattgaga | accccggccc | caaggcagat | gctgttctga | 720 |
| agctagtcgc | cgagttgcgg | aagcggggca | ttcgcattga | cggagtcggt | ctcgagtccc | 780 |
| acttcatcgt | cggcgagact | ccttcgctgg | ctgaccagct | cgccaccaag | aaggcttata | 840 |
| tcgaggccgg | acttgaggtc | gccatcaccg | aacttgacgt | ccgcttttct | cagccccgt  | 900 |
| tctacaccgc | cgaggcccaa | aagcagcagg | ctgccgacta | ctatgctagc | gtcgccagtt | 960 |
| gcaagcatgc | cggaccgcgc | tgtgttggtg | ttgtagtctg | ggatttcgat | gacgcctact | 1020 |
| cgtggattcc | gggtaccttc | gagggacagg | gtggcgcctg | tctatataat | gagacactcg | 1080 |
| aggtgaagcc | ggccttctat | gctgctgccg | aggcgttgga | gaacaagccc | tgcactgtat | 1140 |
| gctag      |            |            |            |            |            | 1145 |

<210> SEQ ID NO 4

```
<211> LENGTH: 364
<212> TYPE: PRT
<213> ORGANISM: Aspergillus fumigatus

<400> SEQUENCE: 4

Met Arg Phe Ser Leu Ala Ala Thr Ala Leu Ala Gly Leu Ala Thr
1               5                   10                  15

Ala Ala Pro Ser Ser Asn Lys Asn Val Asn Leu Asp Lys Leu Ala
                20                  25                  30

Arg Arg Asn Gly Met Leu Trp Phe Gly Thr Ala Ala Asp Ile Pro Gly
            35                  40                  45

Thr Ser Glu Thr Thr Asp Lys Pro Tyr Leu Ser Ile Leu Arg Lys Gln
    50                  55                  60

Phe Gly Glu Met Thr Pro Ala Asn Ala Leu Lys Val Ser Gln Ser Asp
65                  70                  75                  80

Phe Met Tyr Thr Glu Pro Glu Gln Asn Val Phe Asn Phe Thr Gln Gly
                85                  90                  95

Asp Tyr Phe Met Asp Leu Ala Asp His Tyr Gly His Ala Val Arg Cys
            100                 105                 110

His Asn Leu Val Trp Ala Ser Gln Val Ser Asp Trp Val Thr Ser Arg
        115                 120                 125

Asn Trp Thr Ala Thr Glu Leu Lys Glu Val Met Lys Asn His Ile Phe
130                 135                 140

Lys Thr Val Gln His Phe Gly Lys Arg Cys Tyr Ala Trp Asp Val Val
145                 150                 155                 160

Asn Glu Ala Ile Asn Gly Asp Gly Thr Phe Ser Ser Ser Val Trp Tyr
                165                 170                 175

Asp Thr Ile Gly Glu Glu Tyr Phe Tyr Leu Ala Phe Gln Tyr Ala Gln
            180                 185                 190

Glu Ala Leu Ala Gln Ile His Ala Asn Gln Val Lys Leu Tyr Tyr Asn
        195                 200                 205

Asp Tyr Gly Ile Glu Asn Pro Gly Pro Lys Ala Asp Ala Val Leu Lys
    210                 215                 220

Leu Val Ala Glu Leu Arg Lys Arg Gly Ile Arg Ile Asp Gly Val Gly
225                 230                 235                 240

Leu Glu Ser His Phe Ile Val Gly Glu Thr Pro Ser Leu Ala Asp Gln
                245                 250                 255

Leu Ala Thr Lys Lys Ala Tyr Ile Glu Ala Gly Leu Glu Val Ala Ile
            260                 265                 270

Thr Glu Leu Asp Val Arg Phe Ser Gln Ala Pro Phe Tyr Thr Ala Glu
        275                 280                 285

Ala Gln Lys Gln Gln Ala Ala Asp Tyr Tyr Ala Ser Val Ala Ser Cys
    290                 295                 300

Lys His Ala Gly Pro Arg Cys Val Gly Val Val Trp Asp Phe Asp
305                 310                 315                 320

Asp Ala Tyr Ser Trp Ile Pro Gly Thr Phe Glu Gly Gln Gly Gly Ala
                325                 330                 335

Cys Leu Tyr Asn Glu Thr Leu Glu Val Lys Pro Ala Phe Tyr Ala Ala
            340                 345                 350

Ala Glu Ala Leu Glu Asn Lys Pro Cys Thr Val Cys
        355                 360

<210> SEQ ID NO 5
<211> LENGTH: 1400
<212> TYPE: DNA
```

<213> ORGANISM: Aspergillus fumigatus

<400> SEQUENCE: 5

```
atggtcgtcc tcagcaagct cgtcagcagc attctctttg tctccctggt ttcggcgggc      60
gtgatcgacg aacgccaggc agccggcatc aaccaggcgt ttacctccca tggcaagaag     120
tactttggca ccgccagtga ccaagctctg ctccagaagt cgcagaatga ggccattgtg     180
cgcaaagact ttggccagct gacgccggag aatagcatga gtgggatgc gactgagcgt      240
aggtctctcg ccactgtgg ctgacgttaa cttgttgaca tgactgtctg tgtagcatcg      300
caaggaagat tcaacttcgc tggtgctgat ttcctggtat gcaatctgct catctcggtc     360
gagctcctgc tgaaggacaa taataggtc aactatgcaa acagaatgg caagaaggtc       420
cgcggacaca ccttaggtat tcatgcgccc tcacggcatt tcgaggatac agccaagctg     480
acagtgtagt ctggcactcc caactcccgt cctgggtgtc ggctatcagc gacaaaaaca     540
ccctgacctc ggtgctgaag aaccacatca ccaccgtcat gacccggtac aagggccaga     600
tctacgcctg gtattttgc cctctatccc acacaatgcc agcccagct aatagctgca       660
aaggacgtcg tcaacgagat cttcaacgag gacggctccc tccgcgacag cgtcttctcc     720
cgcgtgctgg cgaggactt tgtgcggatt gccttcgaga cggcgcgctc tgtggatccc      780
tcggcgaagc tgtacatcaa cgattacaag taagcttgtg gttttgtcga gagatgtact     840
ccgtcctgga tctgaccatc acagtctcga ctcggctagc tatggcaaaa cccagggggat    900
ggtgagatat gtcaagaagt ggctggctgc gggcattcct atcgatggaa tcggtgagca     960
caggtcgcgg agctgtgtgt gatgattgta cgctgactct tcctgaaggc actcaaaccc    1020
accttggtgc gggtgcttcg tccagcgtca aggataagt ctccttggtt ttcttgccta     1080
cgtaacgctg accccccgtg tacagcattg actgctcttg cgtcttccgg cgtctctgag    1140
gtcgccatta ccgagctgga tatcgcgggt gcgagctccc aggactacgt caatgtatgt    1200
ctcctgattg ccagtggcag ggtcatcgat actaatagaa acaggtcgtc aaggcatgcc    1260
tggatgtccc caagtgtgtg ggaatcaccg tctgggggt gtcggacagg gactcgtggc     1320
gctccggctc gtctccgctg ctgttcgaca gcaactacca gcccaaggcg gcgtataatg    1380
ccatcattgc tgctctctga                                                1400
```

<210> SEQ ID NO 6
<211> LENGTH: 323
<212> TYPE: PRT
<213> ORGANISM: Aspergillus fumigatus

<400> SEQUENCE: 6

```
Met Val Val Leu Ser Lys Leu Val Ser Ser Ile Leu Phe Val Ser Leu
1               5                   10                  15

Val Ser Ala Gly Val Ile Asp Glu Arg Gln Ala Ala Gly Ile Asn Gln
            20                  25                  30

Ala Phe Thr Ser His Gly Lys Lys Tyr Phe Gly Thr Ala Ser Asp Gln
        35                  40                  45

Ala Leu Leu Gln Lys Ser Gln Asn Glu Ala Ile Val Arg Lys Asp Phe
    50                  55                  60

Gly Gln Leu Thr Pro Glu Asn Ser Met Lys Trp Asp Ala Thr Glu Ala
65                  70                  75                  80

Ser Gln Gly Arg Phe Asn Phe Ala Gly Ala Asp Phe Leu Val Asn Tyr
                85                  90                  95

Ala Lys Gln Asn Gly Lys Lys Val Arg Gly His Thr Leu Trp His Ser
```

```
            100                 105                 110
Gln Leu Pro Ser Trp Val Ser Ala Ile Ser Asp Lys Asn Thr Leu Thr
        115                 120                 125

Ser Val Leu Lys Asn His Ile Thr Thr Val Met Thr Arg Tyr Lys Gly
    130                 135                 140

Gln Ile Tyr Ala Trp Asp Val Val Asn Glu Ile Phe Asn Glu Asp Gly
145                 150                 155                 160

Ser Leu Arg Asp Ser Val Phe Ser Arg Val Leu Gly Glu Asp Phe Val
                165                 170                 175

Arg Ile Ala Phe Glu Thr Ala Arg Ser Val Asp Pro Ser Ala Lys Leu
            180                 185                 190

Tyr Ile Asn Asp Tyr Lys Leu Asp Ser Ala Ser Tyr Gly Lys Thr Gln
        195                 200                 205

Gly Met Val Arg Tyr Val Lys Lys Trp Leu Ala Ala Gly Ile Pro Ile
    210                 215                 220

Asp Gly Ile Gly Gln Thr His Leu Gly Ala Gly Ala Ser Ser Ser Val
225                 230                 235                 240

Lys Gly Ala Leu Thr Ala Leu Ala Ser Ser Gly Val Ser Glu Val Ala
                245                 250                 255

Ile Thr Glu Leu Asp Ile Ala Gly Ala Ser Ser Gln Asp Tyr Val Asn
            260                 265                 270

Val Val Lys Ala Cys Leu Asp Val Pro Lys Cys Val Gly Ile Thr Val
        275                 280                 285

Trp Gly Val Ser Asp Arg Asp Ser Trp Arg Ser Gly Ser Ser Pro Leu
    290                 295                 300

Leu Phe Asp Ser Asn Tyr Gln Pro Lys Ala Ala Tyr Asn Ala Ile Ile
305                 310                 315                 320

Ala Ala Leu

<210> SEQ ID NO 7
<211> LENGTH: 1110
<212> TYPE: DNA
<213> ORGANISM: Thielavia terrestris

<400> SEQUENCE: 7
atgcatctcg cctccgcgtt gctcttcctc gcctcgctgc ccctcgggct ggcgggcaag    60
gacaagggca agccgtgcaa gaagggcctc aacacgctcg ccaagcaggc cggcctcaag   120
tacttcggct cggccaccga ctcgccgggc ttccgcgagc gcgccggcta cgaggccgtg   180
tacccgcagt acgaccagat catgtggaag tcgggcgagt ccacatgac  gacgcccacc   240 aacggcatga agtgggtctt caccgagccg agcgcggcg  tgttcaactt caccgagggc   300
gagatcgtgg cgtcgctcgc caagcagaac ggcttcatgc tgcgctgcca cgcgctcgtc   360
tggcacagcc agctccccga ctgggtcacg gcgaccaact ggaccgccgc tgaactgcgc   420
cagatcatcg tcaaccacat cacccacgtg gtcggccatt ggaagggcca gtgctatgcc   480
tgggacgtcg ttaacgaggc gctcaacgag gacggcacct accgcgactc catcttctac   540
caggtgctcg gcgaggagta catcaagctg gcctttgaga ctgcctccaa gattgacccg   600
catgccaagc tgtactacaa cgactacaac ctcgagtatc ccggcccaa  ggtcaccggc   660 gcccagaaca tcgtcaagat gctcaagacc gctggcatcc gcatcgacgg cgtcggcctg   720
cagtcgcacc tcgtcgccga gagccacccg acgctcgacc agcacatcga cgccatccgg   780
tccttctcca gcctcggcgt cgaggtcgcc ctgaccgagc tcgacgtccg cctgacgctg   840
```

```
cccgccaacg cgacgaacct ggccgagcag aacgacgcct acaagaacat cgtcggcgcc    900
tgcgtccagg tccgcggctg catcggcgtc accatctggg acttctacga ccccttcagc    960
tgggtccccg ccaccttccc cggccagggc gcgccgctgc tgtggttcga aacttcacc    1020 acccacccgg cgtaccacgg cgtcgccgag gccctgacga acaagaccac ccgcggccgg    1080
gcccggcgcg cccagctgcg gagcgcctaa                                     1110
```

<210> SEQ ID NO 8
<211> LENGTH: 369
<212> TYPE: PRT
<213> ORGANISM: Thielavia terrestris

<400> SEQUENCE: 8

```
Met His Leu Ala Ser Ala Leu Leu Phe Leu Ala Ser Leu Pro Leu Gly
1               5                   10                  15

Leu Ala Gly Lys Asp Lys Gly Lys Pro Cys Lys Lys Gly Leu Asn Thr
            20                  25                  30

Leu Ala Lys Gln Ala Gly Leu Lys Tyr Phe Gly Ser Ala Thr Asp Ser
        35                  40                  45

Pro Gly Phe Arg Glu Arg Ala Gly Tyr Glu Ala Val Tyr Pro Gln Tyr
    50                  55                  60

Asp Gln Ile Met Trp Lys Ser Gly Glu Phe His Met Thr Thr Pro Thr
65                  70                  75                  80

Asn Gly Met Lys Trp Val Phe Thr Glu Pro Glu Arg Gly Val Phe Asn
                85                  90                  95

Phe Thr Glu Gly Glu Ile Val Ala Ser Leu Ala Lys Gln Asn Gly Phe
            100                 105                 110

Met Leu Arg Cys His Ala Leu Val Trp His Ser Gln Leu Pro Asp Trp
        115                 120                 125

Val Thr Ala Thr Asn Trp Thr Ala Ala Glu Leu Arg Gln Ile Ile Val
    130                 135                 140

Asn His Ile Thr His Val Val Gly His Trp Lys Gly Gln Cys Tyr Ala
145                 150                 155                 160

Trp Asp Val Val Asn Glu Ala Leu Asn Glu Asp Gly Thr Tyr Arg Asp
                165                 170                 175

Ser Ile Phe Tyr Gln Val Leu Gly Glu Glu Tyr Ile Lys Leu Ala Phe
            180                 185                 190

Glu Thr Ala Ser Lys Ile Asp Pro His Ala Lys Leu Tyr Tyr Asn Asp
        195                 200                 205

Tyr Asn Leu Glu Tyr Pro Gly Pro Lys Val Thr Gly Ala Gln Asn Ile
    210                 215                 220

Val Lys Met Leu Lys Thr Ala Gly Ile Arg Ile Asp Gly Val Gly Leu
225                 230                 235                 240

Gln Ser His Leu Val Ala Glu Ser His Pro Thr Leu Asp Gln His Ile
                245                 250                 255

Asp Ala Ile Arg Ser Phe Ser Ser Leu Gly Val Glu Val Ala Leu Thr
            260                 265                 270

Glu Leu Asp Val Arg Leu Thr Leu Pro Ala Asn Ala Thr Asn Leu Ala
        275                 280                 285

Glu Gln Asn Asp Ala Tyr Lys Asn Ile Val Gly Ala Cys Val Gln Val
    290                 295                 300

Arg Gly Cys Ile Gly Val Thr Ile Trp Asp Phe Tyr Asp Pro Phe Ser
305                 310                 315                 320

Trp Val Pro Ala Thr Phe Pro Gly Gln Gly Ala Pro Leu Leu Trp Phe
```

325             330             335
Glu Asn Phe Thr Thr His Pro Ala Tyr His Gly Val Ala Glu Ala Leu
        340                 345                 350

Thr Asn Lys Thr Thr Arg Gly Arg Ala Arg Arg Ala Gln Leu Arg Ser
        355                 360                 365

Ala

<210> SEQ ID NO 9
<211> LENGTH: 1245
<212> TYPE: DNA
<213> ORGANISM: Thielavia terrestris

<400> SEQUENCE: 9
atgcgctccc aggctgtgtg ggccgcgata ctcgcgccgg ccaccgtgtc ggccacgctc      60
aacgacctcg ccgtccgggc cgggctcaag tacttcggca cctgcctcag cgagagttac     120
atcaacagcg atagccagta tgcggccctc atcaatgaca agaccgagtt cggcgggctc     180
gtgcctgaga acggcatgaa gtgggacgcc accgagccca gccagggcca gttcagcttc     240
agccagggcg acatcaccgg gaacacggcc aagaagaacg ccaggtcct gcgctgccac      300
accctggtct ggtacagcca gcttccagga tgggtgacgt cgggctcctg gaccaggagc     360
acgctgcagt cggtcatgca gacgcacatc acgaacgtca tgggccacta caagggccag     420
tgctatgcgt gggacgtggt gaacgaggcc atcgccgacg acggcacgtg gcgcaccagc     480
gtgttctaca cacccttctc gaccgactac atcccgcttg ccttcaacat cgccaagacg     540
gccgacccca cgccaagct gtactacaac gactacaacc tcgagtacaa cggcgccaag     600
acggacacgg ccgtgcagct cgtgcagctc gtgcagtcgg ccggcgcgcc catcgacggc     660
gtcggcttcc agggccacct gatcgtcggc agcacgcccg ccgcagcag cctggcgacc     720
gcgctcaagc gcttcaccgc cctcggcctg gaggtggcct acacggagct cgacatccgg     780
cactccagcc tgccgccgtc cacctcggcg ctcgcgacgc agggcaacga cttcgccaac     840
gtggtcggct cgtgcctcga cgtcgccggc tgcatcggcg tgaccgtctg gggcgtgacc     900
gacaagtact cgtggatccc gcagaccttc ccgggcgccg cgacgcccct gctctacgac     960
gacaactaca acaagaagcc cgcctggacc tcggtctcgt ccgtcctcgc cgccaaggcc    1020
accagcccgc cgcctcgtc gtccaccacc ctcaccaccg tcatcaccac ggccccaacc    1080
tccacccga cgagcaccac cgcgcccacc accacgtcgt cctcgaacgg cgcccagcag    1140
acccactggg gccagtgcgg tggcattggc tggaccggcg ctacgcagtg ccagagcccg    1200
tacacctgcc agaagctgaa cgactggtac atcagtgcc tgtaa                    1245

<210> SEQ ID NO 10
<211> LENGTH: 414
<212> TYPE: PRT
<213> ORGANISM: Thielavia terrestris

<400> SEQUENCE: 10

Met Arg Ser Gln Ala Val Trp Ala Ala Ile Leu Ala Pro Ala Thr Val
1               5                   10                  15

Ser Ala Thr Leu Asn Asp Leu Ala Val Arg Ala Gly Leu Lys Tyr Phe
            20                  25                  30

Gly Thr Cys Leu Ser Glu Ser Tyr Ile Asn Ser Asp Ser Gln Tyr Ala
        35                  40                  45

Ala Leu Ile Asn Asp Lys Thr Glu Phe Gly Gly Leu Val Pro Glu Asn
    50                  55                  60

Gly Met Lys Trp Asp Ala Thr Glu Pro Ser Gln Gly Gln Phe Ser Phe
65                  70                  75                  80

Ser Gln Gly Asp Ile Thr Ala Asn Thr Ala Lys Lys Asn Gly Gln Val
                85                  90                  95

Leu Arg Cys His Thr Leu Val Trp Tyr Ser Gln Leu Pro Gly Trp Val
            100                 105                 110

Thr Ser Gly Ser Trp Thr Arg Ser Thr Leu Gln Ser Val Met Gln Thr
        115                 120                 125

His Ile Thr Asn Val Met Gly His Tyr Lys Gly Gln Cys Tyr Ala Trp
    130                 135                 140

Asp Val Val Asn Glu Ala Ile Ala Asp Gly Thr Trp Arg Thr Ser
145                 150                 155                 160

Val Phe Tyr Asn Thr Phe Ser Thr Asp Tyr Ile Pro Leu Ala Phe Asn
                165                 170                 175

Ile Ala Lys Thr Ala Asp Pro Asn Ala Lys Leu Tyr Tyr Asn Asp Tyr
            180                 185                 190

Asn Leu Glu Tyr Asn Gly Ala Lys Thr Asp Thr Ala Val Gln Leu Val
        195                 200                 205

Gln Leu Val Gln Ser Ala Gly Ala Pro Ile Asp Gly Val Gly Phe Gln
    210                 215                 220

Gly His Leu Ile Val Gly Ser Thr Pro Gly Arg Ser Ser Leu Ala Thr
225                 230                 235                 240

Ala Leu Lys Arg Phe Thr Ala Leu Gly Leu Glu Val Ala Tyr Thr Glu
                245                 250                 255

Leu Asp Ile Arg His Ser Ser Leu Pro Pro Ser Thr Ser Ala Leu Ala
            260                 265                 270

Thr Gln Gly Asn Asp Phe Ala Asn Val Val Gly Ser Cys Leu Asp Val
        275                 280                 285

Ala Gly Cys Ile Gly Val Thr Val Trp Gly Val Thr Asp Lys Tyr Ser
    290                 295                 300

Trp Ile Pro Gln Thr Phe Pro Gly Ala Gly Asp Ala Leu Leu Tyr Asp
305                 310                 315                 320

Asp Asn Tyr Asn Lys Lys Pro Ala Trp Thr Ser Val Ser Ser Val Leu
                325                 330                 335

Ala Ala Lys Ala Thr Ser Pro Pro Ala Ser Ser Ser Thr Thr Leu Thr
            340                 345                 350

Thr Val Ile Thr Thr Ala Pro Thr Ser Thr Pro Thr Ser Thr Thr Ala
        355                 360                 365

Pro Thr Thr Thr Ser Ser Ser Asn Gly Ala Gln Gln Thr His Trp Gly
    370                 375                 380

Gln Cys Gly Gly Ile Gly Trp Thr Gly Ala Thr Gln Cys Gln Ser Pro
385                 390                 395                 400

Tyr Thr Cys Gln Lys Leu Asn Asp Trp Tyr Tyr Gln Cys Leu
                405                 410

<210> SEQ ID NO 11
<211> LENGTH: 1387
<212> TYPE: DNA
<213> ORGANISM: Penicillium emersonii

<400> SEQUENCE: 11
atggttcgcc tcagtccagt cctgctggca tcgatcgcag gctctggcct gcctctgtac    60
gcacaagcag ccggcctcaa caccgccgcc aaagccatcg gcctgaaata cttcggcacg   120

```
gcgaccgaca accccgaact gagcgacacc gcgtacgaga cggaactgaa caacacgcag    180
gatttcgggc agttgacacc tgcgaattcg atgaaggtga gtctgacagc tccccccct     240 cctggggtga gtgagtgagt tcgacgctaa tggttttgc agtgggacgc aaccgagccc     300
cagcaaaaca ctttcacgtt cagcggcggc gatcagatcg ctaacctggc caaggcgaat    360
ggccagatgt tgaggtgcca taatcttgtt tggtataatc agttgccgtc gtggggtatg    420
tatagtacct gcgtacttgt ttgtaatgat tgtcttggct gatttgtgaa gtcaccggtg    480
gatcctggac caacgagacg ctgcttgctg ccatgaagaa tcacatcacc aacgtcgtta    540
cccattacaa gggccagtgc tatgcatggg atgtcgtgaa tgagggtacg tccatataat    600
tgctgttact atcgagagga atcagctaat gacgacagcc ctcaacgacg acggcaccta    660
ccgcagcaac gtcttctacc agtatatcgg ggaggcgtac atccccatcg ccttcgcgac    720
ggccgccgcc gccgaccccg acgccaagct gtactacaac gactacaaca tcgagtaccc    780
cggcgccaag gccacggcgg cgcagaacat cgtcaagctg gtgcagtcgt acggggcgcg    840
catcgacggc gtcggcctgc agtcgcactt catcgtgggc cagacgccca gcacgagcgc    900
ccagcagcag aacatggccg ccttcaccgc gctgggcgtc gaggtcgcca tcaccgagct    960
cgacatccgc atgcagctgc ccgagacgtc cgcgcagctg acgcagcagg cgaccgacta   1020
ccagagcacg gtccaggcct gcgtcaacac cgacagctgc gtcggcatta ccctctggga   1080
ctggaccgac aagtactcgt gggtgcccag caccttctca ggctggggcg acgcctgtcc   1140
ctgggacgac aactaccaga agaaacccgc gtacaacggc atcctcactg ctctgggagg   1200
cacgccctcc tccagtacca gctacacgct cacgccgacg acgacctcaa gcggcggcag   1260
tggcagcccg actgacgtgg cccagcattg ggagcagtgc ggtggcctgg ctggactgg    1320 gccgacggtt tgcgccagtg gcttcacttg cactgtcatc aacgagtatt actcgcagtg   1380
tctgtaa                                                            1387
```

<210> SEQ ID NO 12
<211> LENGTH: 403
<212> TYPE: PRT
<213> ORGANISM: Penicillium emersonii

<400> SEQUENCE: 12

```
Met Val Arg Leu Ser Pro Val Leu Leu Ala Ser Ile Ala Gly Ser Gly
1               5                   10                  15

Leu Pro Leu Tyr Ala Gln Ala Ala Gly Leu Asn Thr Ala Ala Lys Ala
            20                  25                  30

Ile Gly Leu Lys Tyr Phe Gly Thr Ala Thr Asp Asn Pro Glu Leu Ser
        35                  40                  45

Asp Thr Ala Tyr Glu Thr Glu Leu Asn Asn Thr Gln Asp Phe Gly Gln
    50                  55                  60

Leu Thr Pro Ala Asn Ser Met Lys Trp Asp Ala Thr Glu Pro Gln Gln
65                  70                  75                  80

Asn Thr Phe Thr Phe Ser Gly Gly Asp Gln Ile Ala Asn Leu Ala Lys
                85                  90                  95

Ala Asn Gly Gln Met Leu Arg Cys His Asn Leu Val Trp Tyr Asn Gln
            100                 105                 110

Leu Pro Ser Trp Val Thr Gly Gly Ser Trp Thr Asn Glu Thr Leu Leu
        115                 120                 125

Ala Ala Met Lys Asn His Ile Thr Asn Val Val Thr His Tyr Lys Gly
    130                 135                 140
```

Gln Cys Tyr Ala Trp Asp Val Val Asn Glu Ala Leu Asn Asp Asp Gly
145                 150                 155                 160

Thr Tyr Arg Ser Asn Val Phe Tyr Gln Tyr Ile Gly Glu Ala Tyr Ile
            165                 170                 175

Pro Ile Ala Phe Ala Thr Ala Ala Ala Asp Pro Asp Ala Lys Leu
        180                 185                 190

Tyr Tyr Asn Asp Tyr Asn Ile Glu Tyr Pro Gly Ala Lys Ala Thr Ala
        195                 200                 205

Ala Gln Asn Ile Val Lys Leu Val Gln Ser Tyr Gly Ala Arg Ile Asp
    210                 215                 220

Gly Val Gly Leu Gln Ser His Phe Ile Val Gly Gln Thr Pro Ser Thr
225                 230                 235                 240

Ser Ala Gln Gln Gln Asn Met Ala Ala Phe Thr Ala Leu Gly Val Glu
                245                 250                 255

Val Ala Ile Thr Glu Leu Asp Ile Arg Met Gln Leu Pro Glu Thr Ser
                260                 265                 270

Ala Gln Leu Thr Gln Gln Ala Thr Asp Tyr Gln Ser Thr Val Gln Ala
            275                 280                 285

Cys Val Asn Thr Asp Ser Cys Val Gly Ile Thr Leu Trp Asp Trp Thr
    290                 295                 300

Asp Lys Tyr Ser Trp Val Pro Ser Thr Phe Ser Gly Trp Gly Asp Ala
305                 310                 315                 320

Cys Pro Trp Asp Asp Asn Tyr Gln Lys Lys Pro Ala Tyr Asn Gly Ile
                325                 330                 335

Leu Thr Ala Leu Gly Gly Thr Pro Ser Ser Ser Thr Ser Tyr Thr Leu
            340                 345                 350

Thr Pro Thr Thr Thr Ser Ser Gly Gly Ser Gly Ser Pro Thr Asp Val
            355                 360                 365

Ala Gln His Trp Glu Gln Cys Gly Gly Leu Gly Trp Thr Gly Pro Thr
    370                 375                 380

Val Cys Ala Ser Gly Phe Thr Cys Thr Val Ile Asn Glu Tyr Tyr Ser
385                 390                 395                 400

Gln Cys Leu

<210> SEQ ID NO 13
<211> LENGTH: 1197
<212> TYPE: DNA
<213> ORGANISM: Trichophaea saccata

<400> SEQUENCE: 13
atgcgtacct tctcgtctct tctcggtgtt gcccttctct tgggtgcagc taatgcccag    60
gtcgcggttt ggggacagtg tggtggcatt ggttactctg ctcgacaac  ctgcgctgcg   120 ggaacgactt gtgttaagct gaacgactac tactcccaat gccaacccgg cggtaccact   180
ttgacaacca ccaccaaacc cgccaccact accactacca ccacggcaac ttctccctca   240
tcttctcccg gattaaatgc cctggcacaa agagcggcc  ggtacttcgg tagtgcaact   300
gacaacccag agctctccga tgcggcatac attgccatcc tgagcaacaa aaacgagttt   360
gggatcatca cgcctggaaa ctcgatgaaa tgggatgcta ctgaaccgtc cgcggggagt   420
ttctcgttca ctggtggaca gcaaattgtt gattttgcgc agggcaatgg gcaggctatc   480
agaggccata ctcttgtctg gtactcccag ttgccgtcct gggttactag cggaaacttc   540
gataaagcta cattgacatc gatcatgcaa aatcacatta caactcttgt cagccactgg   600
aagggccagc tcgcctactg ggatgttgtc aacgaagcat tcaacgatga tggcactttc   660

-continued

```
cgtcaaaacg tgttctacac aaccattgga gaggactaca tccagctcgc cttcgaagcc      720
gcccgtgccg ccgacccgac cgcaaagctc tgcatcaacg actacaacat cgagggcact      780
ggagccaagt caacagccat gtacaatctc gtctcgaagc tgaaatccgc cggcgttccc      840
atcgactgta ttggtgttca gggacacctc atcgtcggtg aagttcccac caccatccaa      900
gcaaaccttg cccagtttgc gtctttgggt gtggatgtcg cgatcacgga gctagatatc      960
agaatgacgc tgccatctac gactgcattg ctccagcagc aggctaagga ttacgtctcg     1020
gttgttacag cctgcatgaa tgttcccagg tgtatcggta tcaccatctg ggactacact     1080
gataaatact cttgggtgcc acaaaccttc agcggccagg gcgatgcttg cccatgggat     1140
gccaacctgc agaagaagcc agcctactcc gctattgcgt ctgctcttgc ggcttga       1197
```

<210> SEQ ID NO 14
<211> LENGTH: 398
<212> TYPE: PRT
<213> ORGANISM: Trichophaea saccata

<400> SEQUENCE: 14

```
Met Arg Thr Phe Ser Ser Leu Leu Gly Val Ala Leu Leu Gly Ala
1               5                   10                  15

Ala Asn Ala Gln Val Ala Val Trp Gly Gln Cys Gly Gly Ile Gly Tyr
            20                  25                  30

Ser Gly Ser Thr Thr Cys Ala Ala Gly Thr Thr Cys Val Lys Leu Asn
        35                  40                  45

Asp Tyr Tyr Ser Gln Cys Gln Pro Gly Gly Thr Thr Leu Thr Thr Thr
    50                  55                  60

Thr Lys Pro Ala Thr Thr Thr Thr Thr Thr Ala Thr Ser Pro Ser
65                  70                  75                  80

Ser Ser Pro Gly Leu Asn Ala Leu Ala Gln Lys Ser Gly Arg Tyr Phe
                85                  90                  95

Gly Ser Ala Thr Asp Asn Pro Glu Leu Ser Asp Ala Ala Tyr Ile Ala
            100                 105                 110

Ile Leu Ser Asn Lys Asn Glu Phe Gly Ile Ile Thr Pro Gly Asn Ser
        115                 120                 125

Met Lys Trp Asp Ala Thr Glu Pro Ser Arg Gly Ser Phe Ser Phe Thr
    130                 135                 140

Gly Gly Gln Gln Ile Val Asp Phe Ala Gln Gly Asn Gly Gln Ala Ile
145                 150                 155                 160

Arg Gly His Thr Leu Val Trp Tyr Ser Gln Leu Pro Ser Trp Val Thr
                165                 170                 175

Ser Gly Asn Phe Asp Lys Ala Thr Leu Thr Ser Ile Met Gln Asn His
            180                 185                 190

Ile Thr Thr Leu Val Ser His Trp Lys Gly Gln Leu Ala Tyr Trp Asp
        195                 200                 205

Val Val Asn Glu Ala Phe Asn Asp Gly Thr Phe Arg Gln Asn Val
    210                 215                 220

Phe Tyr Thr Thr Ile Gly Glu Asp Tyr Ile Gln Leu Ala Phe Glu Ala
225                 230                 235                 240

Ala Arg Ala Ala Asp Pro Thr Ala Lys Leu Cys Ile Asn Asp Tyr Asn
                245                 250                 255

Ile Glu Gly Thr Gly Ala Lys Ser Thr Ala Met Tyr Asn Leu Val Ser
            260                 265                 270

Lys Leu Lys Ser Ala Gly Val Pro Ile Asp Cys Ile Gly Val Gln Gly
```

```
            275                 280                 285
His Leu Ile Val Gly Glu Val Pro Thr Thr Ile Gln Ala Asn Leu Ala
    290                 295                 300

Gln Phe Ala Ser Leu Gly Val Asp Val Ala Ile Thr Glu Leu Asp Ile
305                 310                 315                 320

Arg Met Thr Leu Pro Ser Thr Thr Ala Leu Leu Gln Gln Gln Ala Lys
                325                 330                 335

Asp Tyr Val Ser Val Val Thr Ala Cys Met Asn Val Pro Arg Cys Ile
                340                 345                 350

Gly Ile Thr Ile Trp Asp Tyr Thr Asp Lys Tyr Ser Trp Val Pro Gln
                355                 360                 365

Thr Phe Ser Gly Gln Gly Asp Ala Cys Pro Trp Asp Ala Asn Leu Gln
    370                 375                 380

Lys Lys Pro Ala Tyr Ser Ala Ile Ala Ser Ala Leu Ala Ala
385                 390                 395

<210> SEQ ID NO 15
<211> LENGTH: 1442
<212> TYPE: DNA
<213> ORGANISM: Penicillium pinophilum

<400> SEQUENCE: 15
atgactctag taaaggctat tcttttagcg cttgctgtgg gccacgttgc ccaggcccaa      60
ttgaacacgg ccgcaaaagc agctggtcta ttgtactttg gtactgcggt tgacaatcca     120
gacttgagcg actccaaata tattgcaaac cttgagactg cggatttcgg tcagatcacg     180
ccagcaaatg caatgaaagt cagtggccaa tcactactgt atacaaccag ctaagtgatg     240
acaatttagt ggcaacccac cgagccgtct caaggctctt atactttcac tcagggtgac     300
cagattgcga gcctggccaa gtctaataat gactacttga gatgccacaa tctggtctgg     360
tacaaccagt tgccatcata cggtaagcaa gcatacgacc tccatgaatt gtcatccaac     420
atccacgata gcaagctgat acggtatctg tctagttact tcgggttcat ggacaaacgc     480
aacccttatt gctgccttga aggagcatat caatggagtt gtcacgcatt acaagggaca     540
atgctacgcg tgggatgttg taaacgaagg tatgcgatat tatatacagg ccctttctct     600
gcatccttac atcttttttta tctccattct acgtaatcgt gtcgagctaa gtgaagtatc     660
tagccttgaa cgaagacggc acctatcgtc aaaatgtttt ctaccaatat ataggcgagg     720
catacattcc aattgcgttt gctgccgctg cagccgcgga ccctaatgcc aagttgtact     780
acaacgacta caacatcgaa tacgctgggt caaaggcaac tggtgctcag cgcattgtaa     840
aattaattca gctgctggt ggtcgtatcg atggcgtggg tcttcagtct cacttcattg     900
tgggacaaac ccctagtctt gctactcaga aagcaaacat ggctgctttt actgctctcg     960
gtgttgatgt tgccattact gagcttgaca ttcgtatgac tctcccggat accagcgctc    1020
ttcaaactca gcagtccacc gactaccaga ccaccactac tgcctgcgtc agactaaag    1080 gctgtgttgg tatcacgcta tgggattaca cagacaagta ctcatgggtt cccggtacct    1140
tctctggcca gggtgatgct tgtccatggg actcaaatta caacaagaag ccggcatact    1200
atggtatcct tgctggctta caatctggca ctggttcttc atcgtcaact tctagcacca    1260
ccctaacaac caccacaaca cccactaccg cttcaagtac tacgtcaacg actagcacaa    1320
gcgctacctc aggtgctgca cactggggac aatgcgagg cattggctgg tctggtccta    1380
ccatttgtgt ttcgccctac acttgtcaag tgttgaaccc atactactcc caatgtttgt    1440
```

```
ga                                                                   1442
```

<210> SEQ ID NO 16
<211> LENGTH: 407
<212> TYPE: PRT
<213> ORGANISM: Penicillium pinophilum

<400> SEQUENCE: 16

Met Thr Leu Val Lys Ala Ile Leu Leu Ala Leu Ala Val Gly His Val
1               5                   10                  15

Ala Gln Ala Gln Leu Asn Thr Ala Ala Lys Ala Ala Gly Leu Leu Tyr
            20                  25                  30

Phe Gly Thr Ala Val Asp Asn Pro Asp Leu Ser Asp Ser Lys Tyr Ile
        35                  40                  45

Ala Asn Leu Glu Thr Ala Asp Phe Gly Gln Ile Thr Pro Ala Asn Ala
    50                  55                  60

Met Lys Trp Gln Pro Thr Glu Pro Ser Gln Gly Ser Tyr Thr Phe Thr
65                  70                  75                  80

Gln Gly Asp Gln Ile Ala Ser Leu Ala Lys Ser Asn Asn Asp Tyr Leu
                85                  90                  95

Arg Cys His Asn Leu Val Trp Tyr Asn Gln Leu Pro Ser Tyr Val Thr
            100                 105                 110

Ser Gly Ser Trp Thr Asn Ala Thr Leu Ile Ala Ala Leu Lys Glu His
        115                 120                 125

Ile Asn Gly Val Val Thr His Tyr Lys Gly Gln Cys Tyr Ala Trp Asp
130                 135                 140

Val Val Asn Glu Ala Leu Asn Glu Asp Gly Thr Tyr Arg Gln Asn Val
145                 150                 155                 160

Phe Tyr Gln Tyr Ile Gly Glu Ala Tyr Ile Pro Ile Ala Phe Ala Ala
                165                 170                 175

Ala Ala Ala Ala Asp Pro Asn Ala Lys Leu Tyr Tyr Asn Asp Tyr Asn
            180                 185                 190

Ile Glu Tyr Ala Gly Ser Lys Ala Thr Gly Ala Gln Arg Ile Val Lys
        195                 200                 205

Leu Ile Gln Ala Ala Gly Gly Arg Ile Asp Gly Val Gly Leu Gln Ser
210                 215                 220

His Phe Ile Val Gly Gln Thr Pro Ser Leu Ala Thr Gln Lys Ala Asn
225                 230                 235                 240

Met Ala Ala Phe Thr Ala Leu Gly Val Asp Val Ala Ile Thr Glu Leu
                245                 250                 255

Asp Ile Arg Met Thr Leu Pro Asp Thr Ser Ala Leu Gln Thr Gln Gln
            260                 265                 270

Ser Thr Asp Tyr Gln Thr Thr Thr Ala Cys Val Gln Thr Lys Gly
        275                 280                 285

Cys Val Gly Ile Thr Leu Trp Asp Tyr Thr Asp Lys Tyr Ser Trp Val
290                 295                 300

Pro Gly Thr Phe Ser Gly Gln Gly Asp Ala Cys Pro Trp Asp Ser Asn
305                 310                 315                 320

Tyr Asn Lys Lys Pro Ala Tyr Tyr Gly Ile Leu Ala Gly Leu Gln Ser
                325                 330                 335

Gly Thr Gly Ser Ser Ser Ser Thr Ser Ser Thr Thr Leu Thr Thr Thr
            340                 345                 350

Thr Thr Pro Thr Thr Ala Ser Ser Thr Thr Ser Thr Thr Ser Thr Ser
        355                 360                 365

-continued

```
Ala Thr Ser Gly Ala Ala His Trp Gly Gln Cys Gly Gly Ile Gly Trp
        370                 375                 380

Ser Gly Pro Thr Ile Cys Val Ser Pro Tyr Thr Cys Gln Val Leu Asn
385                 390                 395                 400

Pro Tyr Tyr Ser Gln Cys Leu
                405

<210> SEQ ID NO 17
<211> LENGTH: 1168
<212> TYPE: DNA
<213> ORGANISM: Talaromyces leycettanus

<400> SEQUENCE: 17
atgcgtttct ccttggccac tgcagctctt ctcgctggcc ctgccctggc agcgccacca      60
gctcctcgtc acgatgacaa ggatgttggg ctcaacgccc tggcccagag agcaggcaag     120
ctctggttcg gcactgctgc tgatatcccc ggcaccgacg agacgaccga tgctgcgtac     180
ctaaaaatct tggaaaatcc cgccaacttc ggcgagatca cccctgccaa cgccatgaag     240
gtacggagct gcttgacaag tcggaggatc atgcctacga gcaacaaac ttccgatgct      300 gacgcattga cagttcatgt acaccgagcc agagcagaac gtgttcaact acaccggcgg     360
tgactacgtc ctgaacctcg ccgagcgcca cggccagcgt gtccgctgcc acaacctcgt     420
ctgggccagc cagctgtccg acttcgtcaa caacggcaac tggaccaagg agtccctcac     480
ggccgtgatg cggaaccaca tcttccacgt cgtccagcac ttcggccggc gctgctactc     540
gtgggatgtc gtcaacgagg ccctcaacgg cgacggcacc ttctcctcca gcatctggta     600
cgacaccatc ggcgaggact acttctacct cgccttccag tacgcccagg aggccctcgc     660
ggagatccac gccaacgacg tcaagctcta ctacaacgac tacggcatcg agaaccccgg     720
caccaaggcc gatgccgtgc acaacctcgt caaggagctg cgcaagcgcg acatccgcat     780
cgacggcatc ggtctcgagt cccacttcga ggtcggtttc accccctccc tacaggacca     840
gctcagcacc aagcagggct acatcgcgct cggtctcgac gtcgccatca ccgagctgga     900
cgtgcgcttc acccaggccc cttactacga tgccgcgggc gagaagcagc aggcccagga     960 ctactataccc agcgtttcta gctgcatcga ggccggcccc aagtgcatcg tatcaccgt    1020 ctgggacttc gatgacaagt actcgtgggt tccttacact ttcgccggcc agggtggtgc    1080
agatatctac aatgctacct gcaggccaa gcctgcctac tatgccattg ccgatgctct    1140
tcagggcaag gcctgcagcg tctgctag                                        1168

<210> SEQ ID NO 18
<211> LENGTH: 364
<212> TYPE: PRT
<213> ORGANISM: Talaromyces leycettanus

<400> SEQUENCE: 18

Met Arg Phe Ser Leu Ala Thr Ala Ala Leu Leu Ala Gly Pro Ala Leu
1               5                   10                  15

Ala Ala Pro Pro Ala Pro Arg His Asp Asp Lys Asp Val Gly Leu Asn
                20                  25                  30

Ala Leu Ala Gln Arg Ala Gly Lys Leu Trp Phe Gly Thr Ala Ala Asp
            35                  40                  45

Ile Pro Gly Thr Asp Glu Thr Thr Asp Ala Ala Tyr Leu Lys Ile Leu
        50                  55                  60

Glu Asn Pro Ala Asn Phe Gly Glu Ile Thr Pro Ala Asn Ala Met Lys
65                  70                  75                  80
```

Phe Met Tyr Thr Glu Pro Glu Gln Asn Val Phe Asn Tyr Thr Gly Gly
            85                  90                  95
Asp Tyr Val Leu Asn Leu Ala Glu Arg His Gly Gln Arg Val Arg Cys
            100                 105                 110
His Asn Leu Val Trp Ala Ser Gln Leu Ser Asp Phe Val Asn Asn Gly
            115                 120                 125
Asn Trp Thr Lys Glu Ser Leu Thr Ala Val Met Arg Asn His Ile Phe
130                 135                 140
His Val Val Gln His Phe Gly Arg Arg Cys Tyr Ser Trp Asp Val Val
145                 150                 155                 160
Asn Glu Ala Leu Asn Gly Asp Gly Thr Phe Ser Ser Ile Trp Tyr
                165                 170                 175
Asp Thr Ile Gly Glu Asp Tyr Phe Tyr Leu Ala Phe Gln Tyr Ala Gln
            180                 185                 190
Glu Ala Leu Ala Glu Ile His Ala Asn Asp Val Lys Leu Tyr Tyr Asn
            195                 200                 205
Asp Tyr Gly Ile Glu Asn Pro Gly Thr Lys Ala Asp Ala Val His Asn
            210                 215                 220
Leu Val Lys Glu Leu Arg Lys Arg Asp Ile Arg Ile Asp Gly Ile Gly
225                 230                 235                 240
Leu Glu Ser His Phe Glu Val Gly Phe Thr Pro Ser Leu Gln Asp Gln
                245                 250                 255
Leu Ser Thr Lys Gln Gly Tyr Ile Ala Leu Gly Leu Asp Val Ala Ile
            260                 265                 270
Thr Glu Leu Asp Val Arg Phe Thr Gln Ala Pro Tyr Tyr Asp Ala Ala
            275                 280                 285
Gly Glu Lys Gln Gln Ala Gln Asp Tyr Tyr Thr Ser Val Ser Ser Cys
            290                 295                 300
Ile Glu Ala Gly Pro Lys Cys Ile Gly Ile Thr Val Trp Asp Phe Asp
305                 310                 315                 320
Asp Lys Tyr Ser Trp Val Pro Tyr Thr Phe Ala Gly Gln Gly Gly Ala
                325                 330                 335
Asp Ile Tyr Asn Ala Thr Leu Gln Ala Lys Pro Ala Tyr Ala Ile
            340                 345                 350
Ala Asp Ala Leu Gln Gly Lys Ala Cys Ser Val Cys
            355                 360

<210> SEQ ID NO 19
<211> LENGTH: 1708
<212> TYPE: DNA
<213> ORGANISM: Talaromyces leycettanus

<400> SEQUENCE: 19
atggtccgtc tttccgctgg acttatcgtc ctcccctcg tgtccgccgc ggccgtcgat    60
ctccagagcc gccaggcggc acagagcatc aacaccctca tccaggccaa gggcaagaag   120
tactggggca cttgcgccga tgagggccga ttgaccgaga actcgcaaaa cccggccatc   180
gccaaggcgg actttggcca ggtgacgcca gagaacagca tgaagtggga tgctactgag   240
cgttagtcag gatgtccatg tgcaatatat agatggatgg ctaactgctg ttgatgtgta   300
gcaagccagg gccagttcaa ctttgctcag gctgattggt tggtaagtga agctggcatg   360
ttgttcagat cctagactgt acggctggct gactgttctc aaggtcaact gggcgcagca   420
aaatggcaag ctgatccgag gccacaacct gggtgagtcc tgttcatcat cacaatcgtc   480

```
atagtagcta cgaacacgct aacttatgtg tcaacagtgt ggcactccca gctcccatcc      540
tgggtgtgcg gtatcaccga caagacggca ttgaccaatg ccatgaccaa ccacatcacc      600
accctggtga gccgctataa ggggaagatc tatgcctggg taagtgtttt tcttttctct      660
actgatatca gttccagaga aacggaggcc actgacagtt gtacaggacg tcgtcaacga      720
acccttcaac gaagatggaa gtcttcgtca gacctgcttc tacaacgtca tcggacctga      780
ctacatcaag attgccttcc aaacagctcg tgcggccgat ccgaacgcga agctctacgt      840
caatgattac aagtaagact gatcaagtcc cagccttagc tgcgttaatc cgctgacatt      900
cataacctca gccttgactc cgcttcctac gccaagacca ccggcgtggc gaaccaggtc      960
aagcagtgga ttgcacaggg tgtcccgatt gacggtattg gttctgagtc tcaccttagg     1020
tatagctgac tcccatgtct caagtcaatg ctagttgtga acgtgtactt acgactttca     1080
aaaacagcgc cggtgcagga gcgggtgtgc cagctgccct gcaagtgctc gccaattccg     1140
gagtctccga ggtcgcgatc accgaactcg atatcgccca gcctcatccc actgactatg     1200
acaacgtaag aagaactctt ctgatatcct ctttaaacca taaagtgtcg tgtgactaac     1260
actctttttt tttcaacata ggtcgcccaa gcctgcctga acgtcgcgaa gtgtgttggt     1320
atcacttcct ggggtatctc tgataaggtc cgtttcatgc ctgcatttcc cttccctgaa     1380
agacaagatg tgtctttcca ttgattgctg acgcctaaat caataacagg actcctggcg     1440
ctccagcgag aaccctgatc tcttcgacag caactatcag cccaaggctg cctacaatgc     1500
tcttgtgacc ttgctcggtg gaagctccgg ctccggctct ggctctggct ctggctctgg     1560
ctctggctca ggctcaggct caggctcagg ctccggccag gctcaacact ggggtcagtg     1620
tggtggcgaa ggctggaccg gaccaacgtc ctgtgtctct ccatacactt gccagtacca     1680
gaaccagtgg tactcccagt gcttgtaa                                         1708
```

<210> SEQ ID NO 20
<211> LENGTH: 389
<212> TYPE: PRT
<213> ORGANISM: Talaromyces leycettanus

<400> SEQUENCE: 20

```
Met Val Arg Leu Ser Ala Gly Leu Ile Val Leu Pro Leu Val Ser Ala
1               5                   10                  15

Ala Ala Val Asp Leu Gln Ser Arg Gln Ala Ala Gln Ser Ile Asn Thr
            20                  25                  30

Leu Ile Gln Ala Lys Gly Lys Lys Tyr Trp Gly Thr Cys Ala Asp Glu
        35                  40                  45

Gly Arg Leu Thr Glu Asn Ser Gln Asn Pro Ala Ile Ala Lys Ala Asp
    50                  55                  60

Phe Gly Gln Val Thr Pro Glu Asn Ser Met Lys Trp Asp Ala Thr Glu
65                  70                  75                  80

Pro Ser Gln Gly Gln Phe Asn Phe Ala Gln Ala Asp Trp Leu Val Asn
                85                  90                  95

Trp Ala Gln Gln Asn Gly Lys Leu Ile Arg Gly His Asn Leu Val Trp
            100                 105                 110

His Ser Gln Leu Pro Ser Trp Val Cys Gly Ile Thr Asp Lys Thr Ala
        115                 120                 125

Leu Thr Asn Ala Met Thr Asn His Ile Thr Thr Leu Val Ser Arg Tyr
    130                 135                 140

Lys Gly Lys Ile Tyr Ala Trp Asp Val Val Asn Glu Pro Phe Asn Glu
145                 150                 155                 160
```

```
Asp Gly Ser Leu Arg Gln Thr Cys Phe Tyr Asn Val Ile Gly Pro Asp
                165                 170                 175

Tyr Ile Lys Ile Ala Phe Gln Thr Ala Arg Ala Ala Asp Pro Asn Ala
            180                 185                 190

Lys Leu Tyr Val Asn Asp Tyr Asn Leu Asp Ser Ala Ser Tyr Ala Lys
        195                 200                 205

Thr Thr Gly Val Ala Asn Gln Val Lys Gln Trp Ile Ala Gln Gly Val
    210                 215                 220

Pro Ile Asp Gly Ile Gly Ser Glu Ser His Leu Ser Ala Gly Ala Gly
225                 230                 235                 240

Ala Gly Val Pro Ala Ala Leu Gln Val Leu Ala Asn Ser Gly Val Ser
                245                 250                 255

Glu Val Ala Ile Thr Glu Leu Asp Ile Ala Gln Ala Ser Ser Thr Asp
            260                 265                 270

Tyr Asp Asn Val Ala Gln Ala Cys Leu Asn Val Ala Lys Cys Val Gly
        275                 280                 285

Ile Thr Ser Trp Gly Ile Ser Asp Lys Asp Ser Trp Arg Ser Ser Glu
    290                 295                 300

Asn Pro Asp Leu Phe Asp Ser Asn Tyr Gln Pro Lys Ala Ala Tyr Asn
305                 310                 315                 320

Ala Leu Val Thr Leu Leu Gly Ser Ser Gly Ser Gly Ser Gly Ser
                325                 330                 335

Gly Ser Gly Ser Gly Ser Gly Ser Gly Ser Gly Ser Gly Ser Gly Ser
                340                 345                 350

Gly Gln Ala Gln His Trp Gly Gln Cys Gly Gly Glu Gly Trp Thr Gly
                355                 360                 365

Pro Thr Ser Cys Val Ser Pro Tyr Thr Cys Gln Tyr Gln Asn Gln Trp
            370                 375                 380

Tyr Ser Gln Cys Leu
385
```

<210> SEQ ID NO 21
<211> LENGTH: 1520
<212> TYPE: DNA
<213> ORGANISM: Talaromyces leycettanus

<400> SEQUENCE: 21

```
atggtccatc tttcttccct ggccctggct ttggccgccg gctcgcagct gtatgtgatc      60
catgccatga ctcgagaagt gctcccaaaa ctgactccaa gtctcaatct tagtgcccaa     120
gctgcaggtc ttaacactgc tgccaaagcg attggaaagc tctatttcgg taccgcaacc     180
gacaacccgg agctgtccga cagcacatac atgcaggaga cggataacac cgatgatttc     240
ggccaactca ccccagctaa ctccatgaag gttcgctgac atcttagttc ccccccccctt     300
ttgggaatct gcgcggagat atgctgagcc ttcaaaacta gtgggatgcc accgagccct     360
ctcagaacac cttcaccttc accaacggtg atcagatcgc aaaccttgct aagagcaacg     420
gtcagatgct gagatgccac aacctggtgt ggtacaacca gttgcccagc tggggtaagc     480
aaccggttct gttaatatca tcagcgtgac cgcatcgatc gtattgcgcg agattggaa      540
agatttgcaa gctaatgtca ctacagtcac cagcggatct tggaccaatg ccacgcttct     600
tgcggccatg aagaaccaca tcaccaacgt tgtgacccac tacaagggac agtgctacgc     660
ttgggatgtt gtcaacgaag gtacgtttcg attcggcttc cctcggaccg tatctgcagg     720
caaaaaggtc aatcaattga caatcgtgat ccccagctct caacgatgat ggcacctacc     780
```

-continued

```
gatccaatgt cttctatcag tacatcggcg aggcatacat tcccattgcc tttgcgaccg    840
ctgccgccgc cgatccaaac gcgaagctct actacaacga ctacaacatt gagtaccccg    900
gcgccaaggc caccgccgcc cagaacatcg tcaagatggt caaggcttac ggcgcgaaaa    960
tcgacggtgt cggtctgcaa tctcacttca tcgttggcag caccccctagc cagagctccc   1020 agcagagcaa catggctgct ttcaccgcgc tcggcgtcga ggtcgccatc accgaactgg   1080
atatccgcat gacgttgcct tccaccagtg ctctcttggc ccagcaatcc accgattacc   1140
agagcactgt gtcggcttgc gtgaacactc cgaagtgcat tggtatcacc ctctgggact   1200
ggaccgacaa gtactcctgg gttcccaaca ccttctccgg ccaaggtgac gcctgccect   1260 gggattctaa ctaccagaag aagcctgcct actacggtat cttgactgcg ctcggaggca   1320
gcgcttccac ctccaccacc accactctgg tgacctccac caggacttcg actacgacca   1380
gcacttcggc cacctccacg tctactggcg ttgctcagca ctggggccag tgcggtggta   1440
tcggctggac agggccgact acctgcgcta gcccctacac ctgccaggaa ctgaatccct   1500
actactacca gtgcctgtaa                                                 1520
```

<210> SEQ ID NO 22
<211> LENGTH: 405
<212> TYPE: PRT
<213> ORGANISM: Talaromyces leycettanus

<400> SEQUENCE: 22

```
Met Val His Leu Ser Ser Leu Ala Leu Ala Leu Ala Ala Gly Ser Gln
1               5                   10                  15

Leu Ala Gln Ala Ala Gly Leu Asn Thr Ala Ala Lys Ala Ile Gly Lys
            20                  25                  30

Leu Tyr Phe Gly Thr Ala Thr Asp Asn Pro Glu Leu Ser Asp Ser Thr
        35                  40                  45

Tyr Met Gln Glu Thr Asp Asn Thr Asp Asp Phe Gly Gln Leu Thr Pro
    50                  55                  60

Ala Asn Ser Met Lys Trp Asp Ala Thr Glu Pro Ser Gln Asn Thr Phe
65                  70                  75                  80

Thr Phe Thr Asn Gly Asp Gln Ile Ala Asn Leu Ala Lys Ser Asn Gly
                85                  90                  95

Gln Met Leu Arg Cys His Asn Leu Val Trp Tyr Asn Gln Leu Pro Ser
            100                 105                 110

Trp Val Thr Ser Gly Ser Trp Thr Asn Ala Thr Leu Leu Ala Ala Met
        115                 120                 125

Lys Asn His Ile Thr Asn Val Val Thr His Tyr Lys Gly Gln Cys Tyr
    130                 135                 140

Ala Trp Asp Val Val Asn Glu Ala Leu Asn Asp Asp Gly Thr Tyr Arg
145                 150                 155                 160

Ser Asn Val Phe Tyr Gln Tyr Ile Gly Glu Ala Tyr Ile Pro Ile Ala
                165                 170                 175

Phe Ala Thr Ala Ala Ala Ala Asp Pro Asn Ala Lys Leu Tyr Tyr Asn
            180                 185                 190

Asp Tyr Asn Ile Glu Tyr Pro Gly Ala Lys Ala Thr Ala Ala Gln Asn
        195                 200                 205

Ile Val Lys Met Val Lys Ala Tyr Gly Ala Lys Ile Asp Gly Val Gly
    210                 215                 220

Leu Gln Ser His Phe Ile Val Gly Ser Thr Pro Ser Gln Ser Ser Gln
225                 230                 235                 240
```

```
Gln Ser Asn Met Ala Ala Phe Thr Ala Leu Gly Val Glu Val Ala Ile
                245                 250                 255
Thr Glu Leu Asp Ile Arg Met Thr Leu Pro Ser Thr Ser Ala Leu Leu
            260                 265                 270
Ala Gln Gln Ser Thr Asp Tyr Gln Ser Thr Val Ser Ala Cys Val Asn
        275                 280                 285
Thr Pro Lys Cys Ile Gly Ile Thr Leu Trp Asp Trp Thr Asp Lys Tyr
    290                 295                 300
Ser Trp Val Pro Asn Thr Phe Ser Gly Gln Gly Asp Ala Cys Pro Trp
305                 310                 315                 320
Asp Ser Asn Tyr Gln Lys Lys Pro Ala Tyr Tyr Gly Ile Leu Thr Ala
                325                 330                 335
Leu Gly Gly Ser Ala Ser Thr Ser Thr Thr Thr Thr Leu Val Thr Ser
            340                 345                 350
Thr Arg Thr Ser Thr Thr Thr Ser Thr Ser Ala Thr Ser Thr Ser Thr
        355                 360                 365
Gly Val Ala Gln His Trp Gly Gln Cys Gly Gly Ile Gly Trp Thr Gly
    370                 375                 380
Pro Thr Thr Cys Ala Ser Pro Tyr Thr Cys Gln Glu Leu Asn Pro Tyr
385                 390                 395                 400
Tyr Tyr Gln Cys Leu
                405

<210> SEQ ID NO 23
<211> LENGTH: 1314
<212> TYPE: DNA
<213> ORGANISM: Humicola insolens

<400> SEQUENCE: 23
atggcgaggc tctctcgcgc cctgctggcg gctgccgccg tagccgccaa tgtctcggcg      60
caacagcaac aacaagcaca agaacagctc cccgagggat gcacggcct catggtggcc      120 gccggcaagg agtatttcgg cacggcgacc gatgtcaaca gcatcgacga cgagatatat     180
cagtccatcc tcaactacca gggcgagttc ggcatggtga cgcccgaaaa ctcgcaaaag     240
tgggagttta ctcaacctcg tcgggacgag ttcgtctaca ccaacgccga caccgtcgtt     300
gggagggcac aagagattgg gcaattagta cgatgccacg ccttgacatg gcattctcaa     360
ttgccgacgt ttggtatgta ttcccctccg ccatttcaaa gccatcatcg gcgatgtgtt     420
ccacgccttt actgacatgg agttttctctt ctccccctcc ttccagtctc aaccacgcaa     480
tggaatgctt ccactctcgc tctttcccta accacccaca tcgacaacgt cgtgacccac     540
ttcgccgggc aatgctacgc ctgggacgtg gtcaacgagg cgttaaacga agacgggtcc     600 tatcgaaaact ctaccttta ccaataccetg gcgaggagt acatcacgat ctccttcgag     660
gcggccgcca agccgaccc ggccgccaag ctctactata cgacttcaa cctcgaaacc     720 tcaccgaaaa aggctgccgg tgccgagcgc atcgtccgtc cctccagga cgccggcgcg     780 cgcatcgacg gcgtcggctt ccaggcccac ctcgtcgtgg gccaaacccc gccgcgcaag     840
aacctcaccg cctcctgtc gcgcttcgcc agcctcggcg ttgaggtggc ctacacggag     900
ctcgacattg ctcacgagtt ccccaaagac agctccaacc ggaccccgga cgccgcggcg     960
ctcgagcagc aagccgaaga ctacgtcgcc gtcgttgggt cgtgcctgga cgagcccaaa    1020
tgcgtcggcg tcacggtctg gcagttcacc gacgagtaca gctgggtccc ggaaacgttt    1080
gaaggccgcg accaggcgtg cttgtggacg cgcgactaca agaagaagcc ggcctacgac    1140
```

```
gccgtgtcca atctgctgcg cgaagcggca gccaacaaca cgggcgtgaa caccaactcg    1200
actgaggata tcccggagcc gatacccctcc aacggggcag cggcggcagc gggcggttgg   1260
gtggccaggg ttgctctggg agcggccttg gttgtgggga tggctttgct ttaa          1314
```

<210> SEQ ID NO 24
<211> LENGTH: 406
<212> TYPE: PRT
<213> ORGANISM: Humicola insolens

<400> SEQUENCE: 24

```
Met Ala Arg Leu Ser Arg Ala Leu Leu Ala Ala Ala Val Ala Ala
1               5                   10                  15

Asn Val Ser Ala Gln Gln Gln Gln Ala Gln Glu Gln Leu Pro Glu
                20                  25                  30

Gly Leu His Gly Leu Met Val Ala Ala Gly Lys Glu Tyr Phe Gly Thr
                35                  40                  45

Ala Thr Asp Val Asn Ser Ile Asp Asp Glu Ile Tyr Gln Ser Ile Leu
50                  55                  60

Asn Tyr Gln Gly Glu Phe Gly Met Val Thr Pro Glu Asn Ser Gln Lys
65                  70                  75                  80

Trp Glu Phe Thr Gln Pro Arg Arg Asp Glu Phe Val Tyr Thr Asn Ala
                85                  90                  95

Asp Thr Val Val Gly Arg Ala Gln Glu Ile Gly Gln Leu Val Arg Cys
                100                 105                 110

His Ala Leu Thr Trp His Ser Gln Leu Pro Thr Phe Val Ser Thr Thr
                115                 120                 125

Gln Trp Asn Ala Ser Thr Leu Ala Ser Phe Leu Thr Thr His Ile Asp
130                 135                 140

Asn Val Val Thr His Phe Ala Gly Gln Cys Tyr Ala Trp Asp Val Val
145                 150                 155                 160

Asn Glu Ala Leu Asn Glu Asp Gly Ser Tyr Arg Asn Ser Thr Phe Tyr
                165                 170                 175

Gln Tyr Leu Gly Glu Glu Tyr Ile Thr Ile Ser Phe Glu Ala Ala
                180                 185                 190

Lys Ala Asp Pro Ala Ala Lys Leu Tyr Tyr Asn Asp Phe Asn Leu Glu
                195                 200                 205

Thr Ser Pro Lys Lys Ala Ala Gly Ala Glu Arg Ile Val Arg Leu Leu
210                 215                 220

Gln Asp Ala Gly Ala Arg Ile Asp Gly Val Gly Phe Gln Ala His Leu
225                 230                 235                 240

Val Val Gly Gln Thr Pro Pro Arg Lys Asn Leu Thr Ala Leu Leu Ser
                245                 250                 255

Arg Phe Ala Ser Leu Gly Val Glu Val Ala Tyr Thr Glu Leu Asp Ile
                260                 265                 270

Ala His Glu Phe Pro Lys Asp Ser Ser Asn Arg Thr Pro Asp Ala Ala
                275                 280                 285

Ala Leu Glu Gln Gln Ala Glu Asp Tyr Val Ala Val Gly Ser Cys
                290                 295                 300

Leu Asp Glu Pro Lys Cys Val Gly Val Thr Val Trp Gln Phe Thr Asp
305                 310                 315                 320

Glu Tyr Ser Trp Val Pro Glu Thr Phe Glu Gly Arg Asp Gln Ala Cys
                325                 330                 335

Leu Trp Thr Arg Asp Tyr Lys Lys Lys Pro Ala Tyr Asp Ala Val Ser
```

```
              340                 345                 350
Asn Leu Leu Arg Glu Ala Ala Ala Asn Asn Thr Gly Val Asn Thr Asn
            355                 360                 365

Ser Thr Glu Asp Ile Pro Glu Pro Ile Pro Ser Asn Gly Ala Ala Ala
        370                 375                 380

Ala Ala Gly Gly Trp Val Ala Arg Val Ala Leu Gly Ala Ala Leu Val
385                 390                 395                 400

Val Gly Met Ala Leu Leu
            405

<210> SEQ ID NO 25
<211> LENGTH: 1350
<212> TYPE: DNA
<213> ORGANISM: Humicola insolens

<400> SEQUENCE: 25
```

| | | | | |
|---|---|---|---|---|
| atgcgtttct ccgcctccct gctccttgcc ctgacgggct ccgctgccgc cagccctatc | 60 |
| cgggctgagg aagagatccg ggtgtacgac ttgcccatct cactgttcga tgatcgtcag | 120 |
| gctgacaaat gatgcagggc cttcacgccc cgccaagtgc agggtctgga tgctgccatg | 180 |
| aaggctgccg aagggagta catcggcacc tccctcaccg tgaggaacga cttccaggag | 240 |
| cagaacatca tccgcactga gttcggctcg atcacgcccg agaacgccca gaagtgggac | 300 |
| gccaccgagc caaccgcgg ccagtttacc ttcggtctg ccgaccagca catggactgg | 360 |
| gcccgccaga acgggaagca cgtccgctgc cacacccttg tctggtactc ccagctcccc | 420 |
| ggctgggtgt ccaacagcgg cttcaacaac gccaccttgc agcaggtgat gcagaatcac | 480 |
| atcaaccaag tgatgggccg gtaccgtggc cgctgcaacc actgggatgt cgtcaatgag | 540 |
| ggtatgtggg caaacattcc atgcatcgca gtcctttatc tccctgatat cagagtgaca | 600 |
| tttgctgaca ttttggcaaa cgctgaacg aggatggcac ctaccgtgac aatgttttcc | 660 |
| tccgagtggt aggagagaaa ccctaaccct atccccaacc tgttgttttt caagctccca | 720 |
| ggctgatggc catgcgattg cagatcggag aggcgtatat cccgattgct ttcaggatgg | 780 |
| ccgcccaggc cgatccctcg gccaagctct actacaatga ctacaacctc gagtatctcg | 840 |
| gacccaaggt tgagggtgct gcccgcatcg tgcgccttgt caagcagtac ggcgctcgca | 900 |
| tcgacggtgt cggctatcag gctccacttg tcaccgagcc caccccgact cagtccaccc | 960 |
| cgactccgtc tgaggaggac ctcatcaagg ctctgcgtat caccgctgac ctcggtgtcg | 1020 |
| atgtcgccta caccgagatt gatatccgca tgcgcacccc gtcgaacgcc cagaagctcc | 1080 |
| agcagcttgc ggatgcttac taccgcgtgg ctcgctcgtg catgaaggtt ccgcgctgcg | 1140 |
| tcggcatgac catttgggta agtccagacc tcccatgaca gaggcactcc gatcaagcgc | 1200 |
| taactccgtg tgtagggcgt cactgaccgg tactcgtggg ttcccaacac cttccgcggt | 1260 |
| gagggtgatg cgctcctttg ggacagcaac taccagagga aggccgctta caacgctttc | 1320 |
| ctccgcggca tccaggagcc cgtcaactaa | 1350 |

```
<210> SEQ ID NO 26
<211> LENGTH: 360
<212> TYPE: PRT
<213> ORGANISM: Humicola insolens

<400> SEQUENCE: 26

Met Arg Phe Ser Ala Ser Leu Leu Leu Ala Leu Thr Gly Ser Ala Ala
1               5                   10                  15
```

| Ala | Ser | Pro | Ile | Arg | Ala | Glu | Glu | Ile | Arg | Val | Ala | Phe | Thr | Pro |
|     |     |     | 20  |     |     |     | 25  |     |     |     | 30  |     |     |     |

| Arg | Gln | Val | Gln | Gly | Leu | Asp | Ala | Ala | Met | Lys | Ala | Ala | Gly | Arg | Glu |
|     |     | 35  |     |     |     |     | 40  |     |     |     |     | 45  |     |     |     |

| Tyr | Ile | Gly | Thr | Ser | Leu | Thr | Val | Arg | Asn | Asp | Phe | Gln | Glu | Gln | Asn |
|     | 50  |     |     |     |     | 55  |     |     |     |     | 60  |     |     |     |     |

| Ile | Ile | Arg | Thr | Glu | Phe | Gly | Ser | Ile | Thr | Pro | Glu | Asn | Ala | Gln | Lys |
| 65  |     |     |     |     | 70  |     |     |     |     | 75  |     |     |     |     | 80  |

| Trp | Asp | Ala | Thr | Glu | Pro | Asn | Arg | Gly | Gln | Phe | Thr | Phe | Gly | Ser | Ala |
|     |     |     |     | 85  |     |     |     |     | 90  |     |     |     |     | 95  |     |

| Asp | Gln | His | Met | Asp | Trp | Ala | Arg | Gln | Asn | Gly | Lys | His | Val | Arg | Cys |
|     |     |     | 100 |     |     |     |     | 105 |     |     |     |     | 110 |     |     |

| His | Thr | Leu | Val | Trp | Tyr | Ser | Gln | Leu | Pro | Gly | Trp | Val | Ser | Asn | Ser |
|     |     | 115 |     |     |     |     | 120 |     |     |     |     | 125 |     |     |     |

| Gly | Phe | Asn | Asn | Ala | Thr | Leu | Gln | Gln | Val | Met | Gln | Asn | His | Ile | Asn |
|     | 130 |     |     |     |     | 135 |     |     |     |     | 140 |     |     |     |     |

| Gln | Val | Met | Gly | Arg | Tyr | Arg | Gly | Arg | Cys | Asn | His | Trp | Asp | Val | Val |
| 145 |     |     |     |     | 150 |     |     |     |     | 155 |     |     |     |     | 160 |

| Asn | Glu | Ala | Leu | Asn | Glu | Asp | Gly | Thr | Tyr | Arg | Asp | Asn | Val | Phe | Leu |
|     |     |     |     | 165 |     |     |     |     | 170 |     |     |     |     | 175 |     |

| Arg | Val | Ile | Gly | Glu | Ala | Tyr | Ile | Pro | Ile | Ala | Phe | Arg | Met | Ala | Ala |
|     |     |     | 180 |     |     |     |     | 185 |     |     |     |     | 190 |     |     |

| Gln | Ala | Asp | Pro | Ser | Ala | Lys | Leu | Tyr | Tyr | Asn | Asp | Tyr | Asn | Leu | Glu |
|     |     |     | 195 |     |     |     |     | 200 |     |     |     |     | 205 |     |     |

| Tyr | Leu | Gly | Pro | Lys | Val | Glu | Gly | Ala | Ala | Arg | Ile | Val | Arg | Leu | Val |
|     | 210 |     |     |     |     | 215 |     |     |     |     | 220 |     |     |     |     |

| Lys | Gln | Tyr | Gly | Ala | Arg | Ile | Asp | Gly | Val | Gly | Tyr | Gln | Ala | His | Leu |
| 225 |     |     |     |     | 230 |     |     |     |     | 235 |     |     |     |     | 240 |

| Val | Thr | Glu | Pro | Thr | Pro | Thr | Gln | Ser | Thr | Pro | Thr | Pro | Ser | Glu | Glu |
|     |     |     |     | 245 |     |     |     |     | 250 |     |     |     |     | 255 |     |

| Asp | Leu | Ile | Lys | Ala | Leu | Arg | Ile | Thr | Ala | Asp | Leu | Gly | Val | Asp | Val |
|     |     |     | 260 |     |     |     |     | 265 |     |     |     |     | 270 |     |     |

| Ala | Tyr | Thr | Glu | Ile | Asp | Ile | Arg | Met | Arg | Thr | Pro | Ser | Asn | Ala | Gln |
|     |     | 275 |     |     |     |     | 280 |     |     |     |     | 285 |     |     |     |

| Lys | Leu | Gln | Gln | Leu | Ala | Asp | Ala | Tyr | Tyr | Arg | Val | Ala | Arg | Ser | Cys |
| 290 |     |     |     |     | 295 |     |     |     |     | 300 |     |     |     |     |     |

| Met | Lys | Val | Pro | Arg | Cys | Val | Gly | Met | Thr | Ile | Trp | Gly | Val | Thr | Asp |
| 305 |     |     |     |     | 310 |     |     |     |     | 315 |     |     |     |     | 320 |

| Arg | Tyr | Ser | Trp | Val | Pro | Asn | Thr | Phe | Arg | Gly | Glu | Gly | Asp | Ala | Leu |
|     |     |     |     | 325 |     |     |     |     | 330 |     |     |     |     | 335 |     |

| Leu | Trp | Asp | Ser | Asn | Tyr | Gln | Arg | Lys | Ala | Ala | Tyr | Asn | Ala | Phe | Leu |
|     |     |     | 340 |     |     |     |     | 345 |     |     |     |     | 350 |     |     |

| Arg | Gly | Ile | Gln | Glu | Pro | Val | Asn |
|     |     |     | 355 |     |     |     | 360 |

<210> SEQ ID NO 27
<211> LENGTH: 1199
<212> TYPE: DNA
<213> ORGANISM: Humicola insolens

<400> SEQUENCE: 27

```
atgcatctcg cttcgtcgct ctttctgctc gccactctgc ccttcggctt cgctgctggc      60
aagggcaagg caagggcaa ggacaacagc gatgttggcc tcgacgtcct ggccaaaaag     120
gctggtctga agtacttcgg tgccgccacc gacacgcccg ccagcggga gcgcgccggt     180
```

```
cttgaggata aatatcccga gtatgacagg atcatgtggc attcgcccga gttcggctcg    240
accacgccca ccaacggcca gaaggtcagt tgcaggccca gtcccggtgc accacttcta    300
tggatagtat caatactgac atgctccttc agtggctgtt tgttgagccc gagcgcggcg    360
tcttcaactt cacagagggc gacgtcgttg cctccaaggc ccgccagcac ggcaagctgc    420
tgcgctgcca cgctctcgtc tggcacagcc agctggctcc ctgggtcgag gagaccgagt    480
ggactccgga ggagctgcgc aaggtcatcg tcgaccacat caccgccgtc gccgccact    540
acaagggcca gtgctacgcc tgggacgttg tcaacgaggc gctgaacgag gacggaacct    600
accgcgagag cgttttctac aaggttctcg gcgaggagta catcaagctt gccttcgaga    660
ccgccgccaa ggtcgaccct aaggccaagc tctactacaa cgactacaac ctcgagtggc    720
cctcggccaa gacggagggc gccaagcgca tcgtcaagct cctcaaggac gccaagatcc    780
ccatccacgg cgtcggcctg caggcccacc tcatcgccga gcagcacccc acgctcgacg    840
accacattgc cgccatccgc ggcttcaccc agctcggcgt cgaggtggct ctcaccgagc    900
tcgacatccg cctcaagacc ccggccaccg aggagaacct tgccctgcag cgcgaggcct    960
acaagaacgt cgtcggcgcc tgcgtccagg tctgcggctg cgtcggtgtc accatctggg   1020
acttctatga tcccttcagc tgggtcccct acttcttcga gggcgagggt gctcccctcc   1080
tgtggttcga ggacttcagc aagcaccccg cctactacgg cgtcgttgag gccctcacca   1140
acaagactcg ccgctcgaag cgcagcattt cggaccgccg ggccaagctc ctggcttaa    1199

<210> SEQ ID NO 28
<211> LENGTH: 376
<212> TYPE: PRT
<213> ORGANISM: Humicola insolens

<400> SEQUENCE: 28

Met His Leu Ala Ser Ser Leu Phe Leu Leu Ala Thr Leu Pro Phe Gly
1               5                   10                  15

Phe Ala Ala Gly Lys Gly Lys Gly Lys Gly Lys Asp Asn Ser Asp Val
                20                  25                  30

Gly Leu Asp Val Leu Ala Lys Lys Ala Gly Leu Lys Tyr Phe Gly Ala
            35                  40                  45

Ala Thr Asp Thr Pro Gly Gln Arg Glu Arg Ala Gly Leu Glu Asp Lys
        50                  55                  60

Tyr Pro Glu Tyr Asp Arg Ile Met Trp His Ser Pro Glu Phe Gly Ser
65                  70                  75                  80

Thr Thr Pro Thr Asn Gly Gln Lys Trp Leu Phe Val Glu Pro Glu Arg
                85                  90                  95

Gly Val Phe Asn Phe Thr Glu Gly Asp Val Val Ala Ser Lys Ala Arg
            100                 105                 110

Gln His Gly Lys Leu Leu Arg Cys His Ala Leu Val Trp His Ser Gln
        115                 120                 125

Leu Ala Pro Trp Val Glu Glu Thr Glu Trp Thr Pro Glu Glu Leu Arg
    130                 135                 140

Lys Val Ile Val Asp His Ile Thr Ala Val Ala Gly His Tyr Lys Gly
145                 150                 155                 160

Gln Cys Tyr Ala Trp Asp Val Val Asn Glu Ala Leu Asn Glu Asp Gly
                165                 170                 175

Thr Tyr Arg Glu Ser Val Phe Tyr Lys Val Leu Gly Glu Glu Tyr Ile
            180                 185                 190
```

```
Lys Leu Ala Phe Glu Thr Ala Ala Lys Val Asp Pro Lys Ala Lys Leu
            195                 200                 205
Tyr Tyr Asn Asp Tyr Asn Leu Glu Trp Pro Ser Ala Lys Thr Glu Gly
        210                 215                 220
Ala Lys Arg Ile Val Lys Leu Leu Lys Asp Ala Lys Ile Pro Ile His
225                 230                 235                 240
Gly Val Gly Leu Gln Ala His Leu Ile Ala Glu Gln His Pro Thr Leu
                245                 250                 255
Asp Asp His Ile Ala Ala Ile Arg Gly Phe Thr Gln Leu Gly Val Glu
            260                 265                 270
Val Ala Leu Thr Glu Leu Asp Ile Arg Leu Lys Thr Pro Ala Thr Glu
        275                 280                 285
Glu Asn Leu Ala Leu Gln Arg Glu Ala Tyr Lys Asn Val Val Gly Ala
290                 295                 300
Cys Val Gln Val Cys Gly Cys Val Gly Val Thr Ile Trp Asp Phe Tyr
305                 310                 315                 320
Asp Pro Phe Ser Trp Val Pro Tyr Phe Phe Gly Glu Gly Ala Pro
                325                 330                 335
Leu Leu Trp Phe Glu Asp Phe Ser Lys His Pro Ala Tyr Tyr Gly Val
            340                 345                 350
Val Glu Ala Leu Thr Asn Lys Thr Arg Arg Ser Lys Arg Ser Ile Ser
        355                 360                 365
Asp Arg Arg Ala Lys Leu Leu Ala
    370                 375

<210> SEQ ID NO 29
<211> LENGTH: 1104
<212> TYPE: DNA
<213> ORGANISM: Humicola insolens

<400> SEQUENCE: 29
atgagagctc cgtcctccgt cgctgccgcg actgccctcc tcttgctggc caccccgcg      60
acggcgcagc ttcacaaact cgctgtccag gcgggtctcc gctacttcgg cgcggccacc    120
gacactcctc accagcgtga gcgcgccccc tacccggagt cctatccgca gtacgacgcc    180
atcctggcca caacgacga attcgggcaa accacgccga ccaacgggca gaagtggctc     240
ttcaccgaac ctgccccgcg cctcttcaac ttcaccgagg cgactacgt cgccgacctg     300
gcagcgtcgc agggcaagct ccttcggtgc cacgccctcg tctggcacag ccagctcgct    360
ccctggggttg aggagaccaa ctggaccgcg cccgccctgg ctgacgccat tgagcgtcac   420
atccgcgccg tcgcgggcta ctaccgtgga agatgccatg cgtgggatgt tgtcaatgag    480
gcgctagacg aggacgggtc ctatcgccag tccattttct accgggtgct ggggggaggag  540
tatcttcgcc tggctttccg ggccgcggcg gccgcggacc ctgacgcgaa gctgtactac    600
aacgactacg gcatcgagcg accaacttcc cccaagacgg ctggtgccct gaggcttgtg   660
aagatgttga aggatgccgg gctgcgagtg gatggcgtcg gtatgcaggc gcatctccat   720
gccgacaatc acccgagtgc cgaggacctc attgccacaa gtgaggcata tgcggaactt    780
gtcgacgagg ttgccttcac ggagctcgac gtgcgcatta aacttcccgt ggacgagcag    840
aaactgcagt ggcagaagga atgctaccaa aaggtggtga cggcgtgcgt gaaggtgaag    900
gcttgcgtgg gaattactct ctgggacttt tacgatccct tcagctgggt cccgcatgtg    960
ttcccgaaca atgagcgtc cctgttgtgg ttcgaggact tctcgaaaca cccggcttat   1020
gacggtatta ttgagacctt caagagtttg attgccgagg cagaggaaca accgaagagg  1080
```
cggagcctgg gatggagggc ttga                                                    1104

<210> SEQ ID NO 30
<211> LENGTH: 367
<212> TYPE: PRT
<213> ORGANISM: Humicola insolens

<400> SEQUENCE: 30

| | | | | | | | | | | | | | | |
|---|---|---|---|---|---|---|---|---|---|---|---|---|---|---|
| Met | Arg | Ala | Pro | Ser | Val | Ala | Ala | Thr | Ala | Leu | Leu | Leu | | |
| 1 | | | | 5 | | | | | 10 | | | | 15 | |
| Ala | Thr | Pro | Ala | Thr | Ala | Gln | Leu | His | Lys | Leu | Ala | Val | Gln | Ala | Gly |
| | | | 20 | | | | | 25 | | | | | 30 | | |
| Leu | Arg | Tyr | Phe | Gly | Ala | Ala | Thr | Asp | Thr | Pro | His | Gln | Arg | Glu | Arg |
| | | | 35 | | | | | 40 | | | | | 45 | | |
| Ala | Pro | Tyr | Pro | Glu | Ser | Tyr | Pro | Gln | Tyr | Asp | Ala | Ile | Leu | Ala | Asn |
| | 50 | | | | | 55 | | | | | 60 | | | | |
| Asn | Asp | Glu | Phe | Gly | Gln | Thr | Thr | Pro | Thr | Asn | Gly | Gln | Lys | Trp | Leu |
| 65 | | | | | 70 | | | | | 75 | | | | | 80 |
| Phe | Thr | Glu | Pro | Ala | Pro | Arg | Leu | Phe | Asn | Phe | Thr | Glu | Gly | Asp | Tyr |
| | | | | 85 | | | | | 90 | | | | | 95 | |
| Val | Ala | Asp | Leu | Ala | Ala | Ser | Gln | Gly | Lys | Leu | Leu | Arg | Cys | His | Ala |
| | | | 100 | | | | | 105 | | | | | 110 | | |
| Leu | Val | Trp | His | Ser | Gln | Leu | Ala | Pro | Trp | Val | Glu | Glu | Thr | Asn | Trp |
| | | | 115 | | | | | 120 | | | | | 125 | | |
| Thr | Ala | Pro | Ala | Leu | Ala | Asp | Ala | Ile | Glu | Arg | His | Ile | Arg | Ala | Val |
| | 130 | | | | | 135 | | | | | 140 | | | | |
| Ala | Gly | Tyr | Tyr | Arg | Gly | Arg | Cys | His | Ala | Trp | Asp | Val | Val | Asn | Glu |
| 145 | | | | | 150 | | | | | 155 | | | | | 160 |
| Ala | Leu | Asp | Glu | Asp | Gly | Ser | Tyr | Arg | Gln | Ser | Ile | Phe | Tyr | Arg | Val |
| | | | | 165 | | | | | 170 | | | | | 175 | |
| Leu | Gly | Glu | Glu | Tyr | Leu | Arg | Leu | Ala | Phe | Arg | Ala | Ala | Ala | Ala | |
| | | | 180 | | | | | 185 | | | | | 190 | | |
| Asp | Pro | Asp | Ala | Lys | Leu | Tyr | Tyr | Asn | Asp | Tyr | Gly | Ile | Glu | Arg | Pro |
| | | | 195 | | | | | 200 | | | | | 205 | | |
| Thr | Ser | Pro | Lys | Thr | Ala | Gly | Ala | Leu | Arg | Leu | Val | Lys | Met | Leu | Lys |
| | 210 | | | | | 215 | | | | | 220 | | | | |
| Asp | Ala | Gly | Leu | Arg | Val | Asp | Gly | Val | Gly | Met | Gln | Ala | His | Leu | His |
| 225 | | | | | 230 | | | | | 235 | | | | | 240 |
| Ala | Asp | Asn | His | Pro | Ser | Ala | Glu | Asp | Leu | Ile | Ala | Thr | Ser | Glu | Ala |
| | | | | 245 | | | | | 250 | | | | | 255 | |
| Tyr | Ala | Glu | Leu | Val | Asp | Glu | Val | Ala | Phe | Thr | Glu | Leu | Asp | Val | Arg |
| | | | 260 | | | | | 265 | | | | | 270 | | |
| Ile | Lys | Leu | Pro | Val | Asp | Glu | Gln | Lys | Leu | Gln | Trp | Gln | Lys | Glu | Cys |
| | | | 275 | | | | | 280 | | | | | 285 | | |
| Tyr | Gln | Lys | Val | Val | Thr | Ala | Cys | Val | Lys | Val | Lys | Ala | Cys | Val | Gly |
| | 290 | | | | | 295 | | | | | 300 | | | | |
| Ile | Thr | Leu | Trp | Asp | Phe | Tyr | Asp | Pro | Phe | Ser | Trp | Val | Pro | His | Val |
| 305 | | | | | 310 | | | | | 315 | | | | | 320 |
| Phe | Pro | Asn | Asn | Gly | Ala | Ser | Leu | Leu | Trp | Phe | Glu | Asp | Phe | Ser | Lys |
| | | | | 325 | | | | | 330 | | | | | 335 | |
| His | Pro | Ala | Tyr | Asp | Gly | Ile | Ile | Glu | Thr | Phe | Lys | Ser | Leu | Ile | Ala |
| | | | 340 | | | | | 345 | | | | | 350 | | |
| Glu | Ala | Glu | Glu | Gln | Pro | Lys | Arg | Arg | Ser | Leu | Gly | Trp | Arg | Ala | |
| | 355 | | | | | 360 | | | | | 365 | | | | |

<210> SEQ ID NO 31
<211> LENGTH: 1623
<212> TYPE: DNA
<213> ORGANISM: Malbranchea cinnamomea

<400> SEQUENCE: 31

```
atgcgcatat cactcgttct tctctccctg gtcttgagtc aggctaccct cggcctttat      60
ttgaaggata gacaagctga agtcagcctt gatgagttga tcaaggcaaa gggcaaagaa     120
tactgtggtg ttgcaaccga tagaagactt ctcacgtcca acacgaatgc ccaaattatc     180
caagccaatt tcggccaggt aaccoctgag aatagcatga agtgggaatc tatccagcgt     240
atgcaacatc ctcgaaaatc tttaggacaa gttgattaaa cgctgttctt ccactgaca      300
gtctttcttt gtagcctctc agggaaactt caattggggt gacgcggact atttggtatg     360
cggaaatgtt ctcttctcac cacccgtcgc tctgaaacta aatataaacg ttaggtggat     420
tgggccacgg aaaatggcaa agttattcga ggtcatacct gggtgcgta gttgtccctg      480
accccgtcct ttggtttatg aggttgactc gagtcaaact gactgtacca gtgtggcatt     540
ctcaacttgc tggttgggtg aataacatca acgacccagc ccagctcact aaagttattc     600
aagatcatat tgctgctgtg gttggccgtt acaagggaaa aattcaccat tgggtgaggc     660
ataacagttc ttcggtcaat caccctctcc ctgcgctaac cttggacata tcctaggacg     720
tcgtgaacga gatcttcaat gaagatggct cccttcgtga ctctgtgttc tcacgggtcc     780
tgggagaaga cttcgtcggt attgcattca atgctgcacg ccaagctgat ccagacgcga     840
aactctatat caacgactac aagtgagagc ctttcttatc tggtcctaag tgacgaccgt     900
tgctcatcaa acctttctca actagccttg acaatcctaa ttacgccaaa actcaggcca     960
tggccaacaa ggtgagggag tggcttgctg ctggcattcc cattgatgga attggtatgt    1020
cccatataat ttggccgagg gtccgcatag aatgactgct gactgcttga ataggcacgc    1080
aagctcatct tcagtatgga accagagtgt cttggctccg tttttcattg aattatcgag    1140
ctaacaagat ttacctaata gggccggtgg cgcaggcggc cttggaggat aagtctccct    1200
ttatgttctt tgatgacatc taaggggctg accgccaaa acagcaattg acgttttagc     1260
gaactccggt gttgctgaag tagccatcac tgagctcgat atcgctggtg ctagcccaga    1320
cgactatgtt actgtatgca acacgggat ccacgctggt caatactatc gcgcttgttg     1380
gggttgatgc tgacagtttta ccacaggctt ttagcggctg catgggcaat gccaaatgcg    1440
ttggtgttac catctggggt gtcgctgacc cggttcgtca actcattcac tctccctgac    1500
ttgaattttg atgctgacaa ttattttag gattcgtggc gtgcggagac gactccactg    1560
ctctttgact ataactacca gccaaagccc gcctaccacg ctgttgccca gtccttgcag    1620
tag                                                                  1623
```

<210> SEQ ID NO 32
<211> LENGTH: 326
<212> TYPE: PRT
<213> ORGANISM: Malbranchea cinnamomea

<400> SEQUENCE: 32

```
Met Arg Ile Ser Leu Val Leu Leu Ser Leu Val Leu Ser Gln Ala Thr
1               5                   10                  15

Leu Gly Leu Tyr Leu Lys Asp Arg Gln Ala Glu Val Ser Leu Asp Glu
            20                  25                  30
```

```
Leu Ile Lys Ala Lys Gly Lys Glu Tyr Cys Gly Val Ala Thr Asp Arg
         35                  40                  45
Arg Leu Leu Thr Ser Asn Thr Asn Ala Gln Ile Ile Gln Ala Asn Phe
 50                  55                  60
Gly Gln Val Thr Pro Glu Asn Ser Met Lys Trp Glu Ser Ile Gln Pro
 65                  70                  75                  80
Ser Gln Gly Asn Phe Asn Trp Gly Asp Ala Asp Tyr Leu Val Asp Trp
                 85                  90                  95
Ala Thr Glu Asn Gly Lys Val Ile Arg Gly His Thr Leu Val Trp His
                100                 105                 110
Ser Gln Leu Ala Gly Trp Val Asn Asn Ile Asn Asp Pro Ala Gln Leu
            115                 120                 125
Thr Lys Val Ile Gln Asp His Ile Ala Ala Val Val Gly Arg Tyr Lys
130                 135                 140
Gly Lys Ile His His Trp Asp Val Val Asn Glu Ile Phe Asn Glu Asp
145                 150                 155                 160
Gly Ser Leu Arg Asp Ser Val Phe Ser Arg Val Leu Gly Glu Asp Phe
                165                 170                 175
Val Gly Ile Ala Phe Asn Ala Ala Arg Gln Ala Asp Pro Asp Ala Lys
                180                 185                 190
Leu Tyr Ile Asn Asp Tyr Asn Leu Asp Asn Pro Asn Tyr Ala Lys Thr
            195                 200                 205
Gln Ala Met Ala Asn Lys Val Arg Glu Trp Leu Ala Ala Gly Ile Pro
210                 215                 220
Ile Asp Gly Ile Gly Thr Gln Ala His Leu Gln Ala Gly Gly Ala Gly
225                 230                 235                 240
Gly Leu Gly Gly Ala Ile Asp Val Leu Ala Asn Ser Gly Val Ala Glu
                245                 250                 255
Val Ala Ile Thr Glu Leu Asp Ile Ala Gly Ala Ser Pro Asp Asp Tyr
                260                 265                 270
Val Thr Ala Phe Ser Gly Cys Met Gly Asn Ala Lys Cys Val Gly Val
            275                 280                 285
Thr Ile Trp Gly Val Ala Asp Pro Asp Ser Trp Arg Ala Glu Thr Thr
290                 295                 300
Pro Leu Leu Phe Asp Tyr Asn Tyr Gln Pro Lys Pro Ala Tyr His Ala
305                 310                 315                 320
Val Ala Gln Ser Leu Gln
                325

<210> SEQ ID NO 33
<211> LENGTH: 1365
<212> TYPE: DNA
<213> ORGANISM: Malbranchea cinnamomea

<400> SEQUENCE: 33
atggtgaagc tactcccagt catcgctgca gctctgtgcg cagtcgacgc agccattgct      60
gctcccactt gggggttggtg agcgtgtctg cacattcacc gtttgaatac agcgatgtga    120
ttatggctaa cgtttcgtcg atcgaacagg ccaagctgga actggtggaa tcgtaaaggt    180
ctgggcaatg cagctcgagc cagagggaag tactttggca cagccacgga caatatctac    240
ttgcctgaca aggcctatct ccggaagctg ttggacatca atgagtttgg gcagatcact    300
ccgtcaaaca tgctgaaggt gagcaactca aatcgtccgc actacattcc caatcgaaag    360
cactacggga gctgctgatg caaaatcttc ctgttgaacc agtgggagac cacggagcct    420
```

```
gaacagggca ggttcaattt cacaccagga gacgagcttg tcaacctggc tctgagaaac    480
ggaaaattcg tccgctgcca tactttggtc tggcacagcc aactggctcc ctggggttag    540
cacactgcct caaactgcct cctccagatc ctggggcag cgtacagcta acgacgaaca    600
gttgaggctc aggagtggac caatgaaact tgatcgagg caatgacgaa ccacgtcaca    660
accgttgcga agcacttcaa gggcaggtgc tacgcttggg atgtcgtgaa tgaaggtacg    720
atgtgaagta acctatgctt caccccaatg cctgtgggaa agcaaggcat aactgactcg    780
attccttcgc cagctttgaa cgaggacgga acattccgcg agtccatctt cctgaaggtc    840
attgggcccg agtacattcc cattgcattt gccgccgctg ctgctgccga tccccacgcg    900
aagctgtact acaacgacta caacctcgaa tggcgaagcg aaaagagcga gggcgcacgg    960
cgtatcgtca agatgatcca ggactatggc gctcgcatcg acggagtcgg gatgcaggcc   1020
cacttgattc tgggcgagac accaagcaca gaagagcaga tggccgtcat cagatcgtac   1080
accgagctag gcgttgaagt tgcatatacg gagctggata ccgcatgga actcccccg    1140 acaaaggaga agcttcggca gcagaaagaa gagtactaca cacgatccg cgcctgcgtg   1200 aagtcgtgga agtgcgtggg cgtcaccatc tgggactgga cagataagta ctcgtggatt   1260
cccgaggtgt ttgagggaga gggtgcagcg ctgcccctgg acaggagct caagaagaag   1320 cctgcatact atggcattga gaaggcgttc aagaagtggt tctag                   1365
```

<210> SEQ ID NO 34
<211> LENGTH: 354
<212> TYPE: PRT
<213> ORGANISM: Malbranchea cinnamomea

<400> SEQUENCE: 34

```
Met Val Lys Leu Leu Pro Val Ile Ala Ala Leu Cys Ala Val Asp
1               5                   10                  15

Ala Ala Ile Ala Ala Pro Thr Trp Gly Trp Pro Ser Trp Asn Trp Trp
            20                  25                  30

Asn Arg Lys Gly Leu Gly Asn Ala Ala Arg Ala Arg Gly Lys Tyr Phe
        35                  40                  45

Gly Thr Ala Thr Asp Asn Ile Tyr Leu Pro Asp Lys Ala Tyr Leu Arg
    50                  55                  60

Lys Leu Leu Asp Ile Asn Glu Phe Gly Gln Ile Thr Pro Ser Asn Met
65                  70                  75                  80

Leu Lys Trp Glu Thr Thr Glu Pro Gln Gly Arg Phe Asn Phe Thr
                85                  90                  95

Pro Gly Asp Glu Leu Val Asn Leu Ala Leu Arg Asn Gly Lys Phe Val
            100                 105                 110

Arg Cys His Thr Leu Val Trp His Ser Gln Leu Ala Pro Trp Val Glu
        115                 120                 125

Ala Gln Glu Trp Thr Asn Glu Thr Leu Ile Glu Ala Met Thr Asn His
    130                 135                 140

Val Thr Thr Val Ala Lys His Phe Lys Gly Arg Cys Tyr Ala Trp Asp
145                 150                 155                 160

Val Val Asn Glu Ala Leu Asn Glu Asp Gly Thr Phe Arg Glu Ser Ile
                165                 170                 175

Phe Leu Lys Val Ile Gly Pro Glu Tyr Ile Pro Ile Ala Phe Ala Ala
            180                 185                 190

Ala Ala Ala Ala Asp Pro His Ala Lys Leu Tyr Tyr Asn Asp Tyr Asn
        195                 200                 205
```

```
Leu Glu Trp Arg Ser Glu Lys Ser Glu Gly Ala Arg Arg Ile Val Lys
    210                 215                 220
Met Ile Gln Asp Tyr Gly Ala Arg Ile Asp Gly Val Gly Met Gln Ala
225                 230                 235                 240
His Leu Ile Leu Gly Glu Thr Pro Ser Thr Glu Glu Gln Met Ala Val
                245                 250                 255
Ile Arg Ser Tyr Thr Glu Leu Gly Val Glu Val Ala Tyr Thr Glu Leu
            260                 265                 270
Asp Ile Arg Met Glu Leu Pro Pro Thr Lys Glu Lys Leu Arg Gln Gln
        275                 280                 285
Lys Glu Glu Tyr Tyr Asn Thr Ile Arg Ala Cys Val Lys Ser Trp Lys
    290                 295                 300
Cys Val Gly Val Thr Ile Trp Asp Trp Thr Asp Lys Tyr Ser Trp Ile
305                 310                 315                 320
Pro Glu Val Phe Glu Gly Gly Ala Ala Leu Pro Trp Asp Arg Glu
                325                 330                 335
Leu Lys Lys Lys Pro Ala Tyr Tyr Gly Ile Glu Lys Ala Phe Lys Lys
            340                 345                 350
Trp Phe

<210> SEQ ID NO 35
<211> LENGTH: 1513
<212> TYPE: DNA
<213> ORGANISM: Corynascus thermophilus

<400> SEQUENCE: 35
atgcggtttt ctgcgcctct tgccctagcc ctcggcggcc tcgtggccgc gaagcccatc      60
gacatggaca gggccatgaa gtgagtgcgg acatccaagt acctcccgag tgcttagttc     120
tgtgcccatc cggccttgcc cagcagctcc cgatgtatta ttcatcaata atattaacaa     180
tggcaccatc gatggcccag gctctttcaa cggcagacgc agaccctcaa cgaggccatg     240
gtcgcctcgg gccgccagta catcggcacc gccctgaccc tccgcggcga ctacaccgag     300
gaggccatcg tcaggaccga gttcggctcc atcacgcccg agaatgccat gaagtgggac     360
gccacggagc ccaaccgcgg ccagttcacc ttcaacgcgg cggaccagca cgtcaactgg     420
gcccggcaga cgggaagca ggtccgctgc cacaccctcg tgtggtactc gcagctgccc     480
ggctgggtct ccaacagcgg cttgacaac gccacccctga tcgacgtcat gtcgaaccac     540
atccgccagg tcatgggcg gtacaagggc gtctgcaccc actgggacgt ggtcaacgaa     600
ggtaagccag tcatcttggt ttttgagaca ggaaaagtaa aaaaaaaaaa aggaaaagaa     660 aagaaagaa aaaagaagaa agaaaagag aaaaagaag aagaaaaaa agaagaaaga     720 aaaaagaag aaagaaaga gaaaaaaaaa gaaagaatga tgattgacat ggcattgga     780 aagccctcaa cgaggacggc acctaccggg acaacgtctt cctccgcgtc atcggcgagg     840
cctacatccc gatcgccttc cgcatcgcgt ccgaggcgga cccggacgcg aagctgtact     900
acaacgacta caacctcgag tacctcgggc ccaagctgga gggcgcggcg cgcatcgtcc     960
ggctggtgca gcagtacggc gtccgcatcg acggcgtcgg ataccaggcc cacctgacga    1020
ccgagtcgac gccgacgcag cagacgccca cgccgtccga ggaggacctc acggccgccc    1080
tgcgcaccac cgccgacctg ggcgtcgacg tcgcctacac cgaggttgac atccgcatgc    1140 tcaccccgc caacgagcag aagctgcagg ccctcgccgc cgcctacaac cgcctcgccc    1200
gctcctgcct caacgtcgac cgctgcgtcg gcatcaccgt ctgggtacgt ctgctgtttt    1260
```

-continued

```
cccctccctt ccccccctcg ttgttcaact tctctggcga atgagagagc ggagcggagc    1320
gaagcgggtt ggattggata aagtgaccat tgctgacccc cctcccctcc tttctgcgct    1380 catataggt gtctccgacc ggtactcgtg ggttcccaac accttctacg gcgagggcga     1440
ggccctgctc tgggacggca acttccagaa gaaggccgcc tacgacgcct tcctcgacgg    1500
catctcctcc tga                                                       1513
```

<210> SEQ ID NO 36
<211> LENGTH: 355
<212> TYPE: PRT
<213> ORGANISM: Corynascus thermophilus

<400> SEQUENCE: 36

```
Met Arg Phe Ser Ala Pro Leu Ala Leu Ala Leu Gly Gly Leu Val Ala
1               5                   10                  15

Ala Lys Pro Ile Asp Met Asp Arg Ala Met Lys Leu Phe Gln Arg Gln
                20                  25                  30

Thr Gln Thr Leu Asn Glu Ala Met Val Ala Ser Gly Arg Gln Tyr Ile
            35                  40                  45

Gly Thr Ala Leu Thr Leu Arg Gly Asp Tyr Thr Glu Glu Ala Ile Val
        50                  55                  60

Arg Thr Glu Phe Gly Ser Ile Thr Pro Glu Asn Ala Met Lys Trp Asp
65                  70                  75                  80

Ala Thr Glu Pro Asn Arg Gly Gln Phe Thr Phe Asn Ala Ala Asp Gln
                85                  90                  95

His Val Asn Trp Ala Arg Gln Asn Gly Lys Gln Val Arg Cys His Thr
            100                 105                 110

Leu Val Trp Tyr Ser Gln Leu Pro Gly Trp Val Ser Asn Ser Gly Phe
        115                 120                 125

Asp Asn Ala Thr Leu Ile Asp Val Met Ser Asn His Ile Arg Gln Val
130                 135                 140

Met Gly Arg Tyr Lys Gly Val Cys Thr His Trp Asp Val Val Asn Glu
145                 150                 155                 160

Ala Leu Asn Glu Asp Gly Thr Tyr Arg Asp Asn Val Phe Leu Arg Val
                165                 170                 175

Ile Gly Glu Ala Tyr Ile Pro Ile Ala Phe Arg Ile Ala Ser Glu Ala
            180                 185                 190

Asp Pro Asp Ala Lys Leu Tyr Tyr Asn Asp Tyr Asn Leu Glu Tyr Leu
        195                 200                 205

Gly Pro Lys Leu Glu Gly Ala Ala Arg Ile Val Arg Leu Val Gln Gln
    210                 215                 220

Tyr Gly Val Arg Ile Asp Gly Val Gly Tyr Gln Ala His Leu Thr Thr
225                 230                 235                 240

Glu Ser Thr Pro Thr Gln Gln Thr Pro Thr Pro Ser Glu Glu Asp Leu
                245                 250                 255

Thr Ala Ala Leu Arg Thr Thr Ala Asp Leu Gly Val Asp Val Ala Tyr
            260                 265                 270

Thr Glu Val Asp Ile Arg Met Leu Thr Pro Ala Asn Glu Gln Lys Leu
        275                 280                 285

Gln Ala Leu Ala Ala Tyr Asn Arg Leu Ala Arg Ser Cys Leu Asn
    290                 295                 300

Val Asp Arg Cys Val Gly Ile Thr Val Trp Gly Val Ser Asp Arg Tyr
305                 310                 315                 320

Ser Trp Val Pro Asn Thr Phe Tyr Gly Glu Gly Glu Ala Leu Leu Trp
```

```
              325                 330                 335
Asp Gly Asn Phe Gln Lys Lys Ala Ala Tyr Asp Ala Phe Leu Asp Gly
        340                 345                 350

Ile Ser Ser
        355
```

<210> SEQ ID NO 37
<211> LENGTH: 1101
<212> TYPE: DNA
<213> ORGANISM: Corynascus thermophilus

<400> SEQUENCE: 37

```
atgcgactct ccgcgccctt cctcgcgtcc gcgctcctcc tcagcccggc cgcggcgcag      60
ctccacgcgc tcgcccgcaa ggccgggctc ctctacttcg gcgcggccac cgacacgccg     120
ggccagcgcg agcgggcgcc gtacccggag cgtacccgc agtacgacgc catcttccgg     180
gacccggccg agttcgggca gacgacgccg accaacgggc agaagtggct gttcaccgag     240
ccggcgccgc ggctgttcaa cttcaccgag gcgacgtgg tcgccgacct ggcccggtcg      300
accggcaagc tcctgcgctg ccacgccctg gtctggcaca gccagctggc gccctgggtc     360
gagcggaccg agtggacggc cgaggcgctg cgggacgcca tcgagcggca cgtccgcgcc     420
gtggccggct actaccgcgg ccgctgctac gcctgggacg tggtcaacga ggcgctcgac     480
gaggacggct cctaccgcaa gagcgtcttc tacaacgtgc tcggcgagga gtacatccgg     540
ctcgccttcc gcgccgccgc cgaggccgac ccgggcgccc ggctgtacta caacgactac     600
ggcatcgagc ggcccgactc gcccaagacc gccggcgccc tccgcctcgt gagcatgctg     660
cgccgcgccg gcatccgcat cgacggcgtc ggcatgcagg cccacctgca cgccgacaac     720
cacccctccg ccgaggacct gatcctcacc agcgagcgct acgccgcct cgtgcccgag     780
gtcgccttca ccgagctcga cgtccgcatc aagctgcccg tcaacgagac caagctcgag     840
tggcagagcg actgctacga gaaggtcgtg accgcctgcg tcaaggtcaa ggcctgcgtc     900
ggcatcaccc tgtgggactt ttacgacccc ttcagctggg tgcccgacac cttccccggc     960
cagggcgcct ccctgctgtg gttcgacgat ttctccaagc acccggccta tgaccgcatc    1020
gtcaagacct tcaagaagct gatccgcgag aagaagaggc cgtggttcaa tcgcaaggga    1080
aagacggtcc cggcaaacta a                                             1101
```

<210> SEQ ID NO 38
<211> LENGTH: 366
<212> TYPE: PRT
<213> ORGANISM: Corynascus thermophilus

<400> SEQUENCE: 38

```
Met Arg Leu Ser Ala Pro Phe Leu Ala Ser Ala Leu Leu Leu Ser Pro
1               5                   10                  15

Ala Ala Ala Gln Leu His Ala Leu Ala Arg Lys Ala Gly Leu Leu Tyr
            20                  25                  30

Phe Gly Ala Ala Thr Asp Thr Pro Gly Gln Arg Glu Arg Ala Pro Tyr
        35                  40                  45

Pro Glu Ala Tyr Pro Gln Tyr Asp Ala Ile Phe Arg Asp Pro Ala Glu
    50                  55                  60

Phe Gly Gln Thr Thr Pro Thr Asn Gly Gln Lys Trp Leu Phe Thr Glu
65                  70                  75                  80

Pro Ala Pro Arg Leu Phe Asn Phe Thr Glu Gly Asp Val Val Ala Asp
                85                  90                  95
```

```
Leu Ala Arg Ser Thr Gly Lys Leu Leu Arg Cys His Ala Leu Val Trp
        100                 105                 110

His Ser Gln Leu Ala Pro Trp Val Glu Arg Thr Glu Trp Thr Ala Glu
        115                 120                 125

Ala Leu Arg Asp Ala Ile Glu Arg His Val Arg Ala Val Ala Gly Tyr
    130                 135                 140

Tyr Arg Gly Arg Cys Tyr Ala Trp Asp Val Val Asn Glu Ala Leu Asp
145                 150                 155                 160

Glu Asp Gly Ser Tyr Arg Lys Ser Val Phe Tyr Asn Val Leu Gly Glu
                165                 170                 175

Glu Tyr Ile Arg Leu Ala Phe Arg Ala Ala Glu Ala Asp Pro Gly
            180                 185                 190

Ala Arg Leu Tyr Tyr Asn Asp Tyr Gly Ile Glu Arg Pro Asp Ser Pro
        195                 200                 205

Lys Thr Ala Gly Ala Leu Arg Leu Val Ser Met Leu Arg Arg Ala Gly
        210                 215                 220

Ile Arg Ile Asp Gly Val Gly Met Gln Ala His Leu His Ala Asp Asn
225                 230                 235                 240

His Pro Ser Ala Glu Asp Leu Ile Leu Thr Ser Glu Arg Tyr Ala Arg
                245                 250                 255

Leu Val Pro Glu Val Ala Phe Thr Glu Leu Asp Val Arg Ile Lys Leu
            260                 265                 270

Pro Val Asn Glu Thr Lys Leu Glu Trp Gln Ser Asp Cys Tyr Glu Lys
        275                 280                 285

Val Val Thr Ala Cys Val Lys Val Lys Ala Cys Val Gly Ile Thr Leu
        290                 295                 300

Trp Asp Phe Tyr Asp Pro Phe Ser Trp Val Pro Asp Thr Phe Pro Gly
305                 310                 315                 320

Gln Gly Ala Ser Leu Leu Trp Phe Asp Phe Ser Lys His Pro Ala
                325                 330                 335

Tyr Asp Arg Ile Val Lys Thr Phe Lys Lys Leu Ile Arg Glu Lys Lys
            340                 345                 350

Arg Pro Trp Phe Asn Arg Lys Gly Lys Thr Val Pro Ala Asn
        355                 360                 365

<210> SEQ ID NO 39
<211> LENGTH: 1365
<212> TYPE: DNA
<213> ORGANISM: Corynascus thermophilus

<400> SEQUENCE: 39
atgcgtactc tcgccttcgc tctcgcggcc gccccgccg ctgttctcgc ccagtccccc    60
ctctggggcc agtgtatgcg gtttcccttc ctcccgctct gaagggaggg gacttgctct   120
cgctaaccac ctcctgcttc accataggcg gcggcattgg ctggacgggt cccacgacct   180
gcgtttctgg cgcggtgtgc caatatgtca agtcagtctt cacccgcttc ctcgtttgcg   240
cctgacggcc atcccgattg ctgacacaat ctccccagcg actggtactc gcagtgcgtg   300
cccggcaatg gcggcaaccc cacgacctcc agcgctccca cctcgaccgg tgcagcggc    360 ccgactccta ctggtggcct ccatgacagg ttcaaggcca agggcaaggt ctacttcggt   420
gccgagatcg accactacca cctgaacaac aatgccttga ccaacatcgt caagaaggac   480
tttggccagg tcacgcacga gaacagcctg aagtgggatg ctactgagcg taagcgacct   540
ccttcctcgc aacttgtttt gttgtatgtc ttgaagaacc acagctgacg gcgacctcga   600
```

```
tccgtagcga gccgcaacgg cttcagcttc aacaacgccg acgccgtcgt caactttgcc      660
cagtccaacg ggaagtacat ccgcggccac accctcctct ggcactctca gctgccgcag      720
tgggtgtcgc agatcaacga ccgcaacacc ctgacccagg tcatccagaa ccacgtcacc      780
accctcgtca cccgctacaa gggcaagatc ctccactggg acgtcgtcaa cgagatcttc      840
aacgaggacg gctcgctccg caacagcgtc ttcagccgcg tgctcggcga ggacttcgtc      900
ggcatcgcct tccgcgccgc tcgcgccgcc gaccccgatg ccaagctcta cattaacgac      960
tacaacctcg acatcgccaa ctacgccaag gtcaccaccg gcatggtcca gcacgtcaac     1020
aagtgggtca gccagggcat ccccatcgac ggcatcggct cccagtgcca cctggccgct     1080
cccggcggct ggaacccggc ctcgggcgtg cccgccgctc tccagaccct cgcctcggcc     1140
aacgtgaagg agatcgccat caccgagctc gacatcgccg cgccaacgc caacgactac     1200 ctcaccgtca tgaacggctg cctccaggtc tccaagtgcg tcggtatcac cgtctggggt     1260
gtctcggacc gcgacagctg gcgctcgaac gactacccgc tcctcttcga cggcaactac     1320
cagcccaagg ccgcctacaa cgctctcatc aacgccctga gctaa                     1365
```

```
<210> SEQ ID NO 40
<211> LENGTH: 381
<212> TYPE: PRT
<213> ORGANISM: Corynascus thermophilus

<400> SEQUENCE: 40

Met Arg Thr Leu Ala Phe Ala Leu Ala Ala Ala Pro Ala Ala Val Leu
1               5                   10                  15

Ala Gln Ser Pro Leu Trp Gly Gln Cys Gly Gly Ile Gly Trp Thr Gly
            20                  25                  30

Pro Thr Thr Cys Val Ser Gly Ala Val Cys Gln Tyr Val Asn Asp Trp
        35                  40                  45

Tyr Ser Gln Cys Val Pro Gly Asn Gly Gly Asn Pro Thr Thr Ser Ser
    50                  55                  60

Ala Pro Thr Ser Thr Gly Gly Ser Gly Pro Thr Pro Thr Gly Gly Leu
65                  70                  75                  80

His Asp Arg Phe Lys Ala Lys Gly Lys Val Tyr Phe Gly Ala Glu Ile
                85                  90                  95

Asp His Tyr His Leu Asn Asn Asn Ala Leu Thr Asn Ile Val Lys Lys
            100                 105                 110

Asp Phe Gly Gln Val Thr His Glu Asn Ser Leu Lys Trp Asp Ala Thr
        115                 120                 125

Glu Pro Ser Arg Asn Gly Phe Ser Phe Asn Asn Ala Asp Ala Val Val
    130                 135                 140

Asn Phe Ala Gln Ser Asn Gly Lys Tyr Ile Arg Gly His Thr Leu Leu
145                 150                 155                 160

Trp His Ser Gln Leu Pro Gln Trp Val Ser Gln Ile Asn Asp Arg Asn
                165                 170                 175

Thr Leu Thr Gln Val Ile Gln Asn His Val Thr Thr Leu Val Thr Arg
            180                 185                 190

Tyr Lys Gly Lys Ile Leu His Trp Asp Val Val Asn Glu Ile Phe Asn
        195                 200                 205

Glu Asp Gly Ser Leu Arg Asn Ser Val Phe Ser Arg Val Leu Gly Glu
    210                 215                 220

Asp Phe Val Gly Ile Ala Phe Arg Ala Ala Arg Ala Ala Asp Pro Asp
225                 230                 235                 240
```

Ala Lys Leu Tyr Ile Asn Asp Tyr Asn Leu Asp Ile Ala Asn Tyr Ala
            245                 250                 255

Lys Val Thr Thr Gly Met Val Gln His Val Asn Lys Trp Val Ser Gln
        260                 265                 270

Gly Ile Pro Ile Asp Gly Ile Gly Ser Gln Cys His Leu Ala Ala Pro
        275                 280                 285

Gly Gly Trp Asn Pro Ala Ser Gly Val Pro Ala Ala Leu Gln Thr Leu
        290                 295                 300

Ala Ser Ala Asn Val Lys Glu Ile Ala Ile Thr Glu Leu Asp Ile Ala
305                 310                 315                 320

Gly Ala Asn Ala Asn Asp Tyr Leu Thr Val Met Asn Gly Cys Leu Gln
                325                 330                 335

Val Ser Lys Cys Val Gly Ile Thr Val Trp Gly Val Ser Asp Arg Asp
            340                 345                 350

Ser Trp Arg Ser Asn Asp Tyr Pro Leu Leu Phe Asp Gly Asn Tyr Gln
        355                 360                 365

Pro Lys Ala Ala Tyr Asn Ala Leu Ile Asn Ala Leu Ser
    370                 375                 380

<210> SEQ ID NO 41
<211> LENGTH: 1168
<212> TYPE: DNA
<213> ORGANISM: Penicillium oxalicum

<400> SEQUENCE: 41

```
atgcgctcca cgttcatggt tgcggccttg ctggccgggg cttctcaggc tgttccccat      60
tcaccttctg caacggcca caatgtggac ctcaataagc ttgcacagcg tcgaggactg     120
cattggtttg gcacagcagc cgatatccct ggtactgccg agactaccga tgctgcctat     180
ctgaaagttc tacgaaagaa ttttggcgaa gtgactccag cgaatgctat gaaggtatgg     240
acatatgaat ctgcataatt cacacctcgg agaggtacaa tcctacaact gtcctgctaa     300
tttggaccta tagttcatgt ataccgagcc gcaacaagac gtgttcaatt tcaccgcggc     360
tgatgaattt ttagacgtgg ccggacgcca tggggctaag attcgctgtc acaatcttgt     420
ttgggccagc caagtttctg attttgtaac ctcaaagacc tggactgcgg aggctctcac     480
ctccgtcatg aaaaccaca tttacaagac ggtccagcac tttggtaagc gctgctactc     540
atgggatgtg gtcaacgagg ccatcaatgg agatggttcc ttctcacaga gtgtgtggta     600
caacactatc ggcgaggagt atttctatct tgctttcaag ttcgctcagg aagcattagc     660
cgagattggc gcccacgatg tgaagctgta ctacaacgac tacggcatcg agaatcaggg     720
cacaaagtcg gcgacagtac ttaagcttgt caagcaactg cgaagccgag ggctccgcat     780
tgacggcgtc ggtctcgagt cacacttcat cgttggcgaa acaccttcgt tggcggatca     840
agtggccacc aagaaagctt acattccagc tggcctggag gtggccgtca ccgagcttga     900
catacgcttc gcacagactc cttattatac tgccgctgtt cagaagcagc aagctcaaga     960
ctactacacg agtgtgatga gttgcttgaa tgtcggtcca cgctgcatcg tgttgttgt    1020
ctgggacttt gacgatgcct attcctgggt gcccggggca tttgccggtc aaggtggtgc    1080
ttgtttgttt aatgagactc tcgaggcaaa gcctgcattc tacgccgtgg ttgatgctct    1140
cgaggggaaa gcttgcagtg tttgttaa                                      1168
```

<210> SEQ ID NO 42
<211> LENGTH: 362

<212> TYPE: PRT
<213> ORGANISM: Penicillium oxalicum

<400> SEQUENCE: 42

```
Met Arg Ser Thr Phe Met Val Ala Ala Leu Leu Ala Gly Ala Ser Gln
1               5                   10                  15

Ala Val Pro His Ser Pro Ser Gly Asn Gly His Asn Val Asp Leu Asn
            20                  25                  30

Lys Leu Ala Gln Arg Arg Gly Leu His Trp Phe Gly Thr Ala Ala Asp
        35                  40                  45

Ile Pro Gly Thr Ala Glu Thr Thr Asp Ala Ala Tyr Leu Lys Val Leu
50                  55                  60

Arg Lys Asn Phe Gly Glu Val Thr Pro Ala Asn Ala Met Lys Phe Met
65                  70                  75                  80

Tyr Thr Glu Pro Gln Gln Asp Val Phe Asn Phe Thr Ala Ala Asp Glu
                85                  90                  95

Phe Leu Asp Val Ala Gly Arg His Gly Ala Lys Ile Arg Cys His Asn
            100                 105                 110

Leu Val Trp Ala Ser Gln Val Ser Asp Phe Val Thr Ser Lys Thr Trp
        115                 120                 125

Thr Ala Glu Ala Leu Thr Ser Val Met Lys Asn His Ile Tyr Lys Thr
130                 135                 140

Val Gln His Phe Gly Lys Arg Cys Tyr Ser Trp Asp Val Val Asn Glu
145                 150                 155                 160

Ala Ile Asn Gly Asp Gly Ser Phe Ser Gln Ser Val Trp Tyr Asn Thr
                165                 170                 175

Ile Gly Glu Glu Tyr Phe Tyr Leu Ala Phe Lys Phe Ala Gln Glu Ala
            180                 185                 190

Leu Ala Glu Ile Gly Ala His Asp Val Lys Leu Tyr Tyr Asn Asp Tyr
        195                 200                 205

Gly Ile Glu Asn Gln Gly Thr Lys Ser Ala Thr Val Leu Lys Leu Val
210                 215                 220

Lys Gln Leu Arg Ser Arg Gly Leu Arg Ile Asp Gly Val Gly Leu Glu
225                 230                 235                 240

Ser His Phe Ile Val Gly Glu Thr Pro Ser Leu Ala Asp Gln Val Ala
                245                 250                 255

Thr Lys Lys Ala Tyr Ile Gln Ala Gly Leu Glu Val Ala Val Thr Glu
            260                 265                 270

Leu Asp Ile Arg Phe Ala Gln Thr Pro Tyr Tyr Thr Ala Ala Val Gln
        275                 280                 285

Lys Gln Gln Ala Gln Asp Tyr Tyr Thr Ser Val Met Ser Cys Leu Asn
290                 295                 300

Val Gly Pro Arg Cys Ile Gly Val Val Val Trp Asp Phe Asp Asp Ala
305                 310                 315                 320

Tyr Ser Trp Val Pro Gly Ala Phe Ala Gly Gln Gly Ala Cys Leu
                325                 330                 335

Phe Asn Glu Thr Leu Glu Ala Lys Pro Ala Phe Tyr Ala Val Val Asp
            340                 345                 350

Ala Leu Glu Gly Lys Ala Cys Ser Val Cys
        355                 360
```

<210> SEQ ID NO 43
<211> LENGTH: 1242
<212> TYPE: DNA
<213> ORGANISM: Myceliophthora thermophila

<400> SEQUENCE: 43

```
atgcactcca aagctttctt ggcagcgctt cttgcgcctg ccgtctcagg gcaactgaac        60
gacctcgccg tcagggctgg actcaagtac tttggtactg ctcttagcga gagcgtcatc       120
aacagtgata ctcggtatgc tgccatcctc agcgacaaga gcatgttcgg ccagctcgtc       180
cccgagaatg gcatgaagtg ggatgctact gagccgtccc gtggccagtt caactacgcc       240
tcgggcgaca tcacggccaa cacggccaag aagaatggcc agggcatgcg ttgccacacc       300
atggtctggt acagccagct cccgagctgg gtctcctcgg gctcgtggac cagggactcg       360
ctcacctcgg tcatcgagac gcacatgaac aacgtcatgg gccactacaa gggccaatgc       420
tacgcctggg atgtcatcaa cgaggccatc aatgacgacg gcaactcctg gcgcgacaac       480
gtctttctcc ggacctttgg gaccgactac ttcgccctgt ccttcaacct agccaagaag       540
gccgatcccg ataccaagct gtactacaac gactacaacc tcgagtacaa ccaggccaag       600
acggaccgcg ctgttgagct cgtcaagatg gtccaggccg ccggcgcgcc catcgacggt       660
gtcggcttcc agggccacct cattgtcggc tcgaccccga cgcgctcgca gctggccacc       720
gccctccagc gcttcaccgc gctcggcctc gaggtcgcct acaccgagct cgacatccgc       780
cactcgagcc tgccggcctc ttcgtcggcg ctcgcgaccc agggcaacga cttcgccaac       840
gtggtcggct cttgcctcga caccgccggc tgcgtcggcg tcaccgtctg gggcttcacc       900
gatgcgcact cgtggatccc gaacacgttc cccggccagg cgacgcccct gatctacgac       960
agcaactaca acaagaagcc cgcgtggacc tcgatctcgt ccgtcctggc cgccaaggcc      1020
accggcgccc cgcccgcctc gtcctccacc accctcgtca ccatcaccac ccctccgccg      1080
gcatccacca ccgcctcctc ctcctccagt gccacgccca cgagcgtccc gacgcagacg      1140
aggtggggac agtgcggcgg catcggatgg acggggccga cccagtgcga gagcccatgg      1200
acctgccaga agctgaacga ctggtactgg cagtgcctgt aa                        1242
```

<210> SEQ ID NO 44
<211> LENGTH: 413
<212> TYPE: PRT
<213> ORGANISM: Myceliophthora thermophila

<400> SEQUENCE: 44

```
Met His Ser Lys Ala Phe Leu Ala Ala Leu Leu Ala Pro Ala Val Ser
1               5                   10                  15

Gly Gln Leu Asn Asp Leu Ala Val Arg Ala Gly Leu Lys Tyr Phe Gly
            20                  25                  30

Thr Ala Leu Ser Glu Ser Val Ile Asn Ser Asp Thr Arg Tyr Ala Ala
        35                  40                  45

Ile Leu Ser Asp Lys Ser Met Phe Gly Gln Leu Val Pro Glu Asn Gly
    50                  55                  60

Met Lys Trp Asp Ala Thr Glu Pro Ser Arg Gly Gln Phe Asn Tyr Ala
65                  70                  75                  80

Ser Gly Asp Ile Thr Ala Asn Thr Ala Lys Lys Asn Gly Gln Gly Met
                85                  90                  95

Arg Cys His Thr Met Val Trp Tyr Ser Gln Leu Pro Ser Trp Val Ser
            100                 105                 110

Ser Gly Ser Trp Thr Arg Asp Ser Leu Thr Ser Val Ile Glu Thr His
        115                 120                 125

Met Asn Asn Val Met Gly His Tyr Lys Gly Gln Cys Tyr Ala Trp Asp
    130                 135                 140
```

Val Ile Asn Glu Ala Ile Asn Asp Asp Gly Asn Ser Trp Arg Asp Asn
145                 150                 155                 160

Val Phe Leu Arg Thr Phe Gly Thr Asp Tyr Phe Ala Leu Ser Phe Asn
            165                 170                 175

Leu Ala Lys Lys Ala Asp Pro Asp Thr Lys Leu Tyr Tyr Asn Asp Tyr
        180                 185                 190

Asn Leu Glu Tyr Asn Gln Ala Lys Thr Asp Arg Ala Val Glu Leu Val
    195                 200                 205

Lys Met Val Gln Ala Ala Gly Ala Pro Ile Asp Gly Val Gly Phe Gln
210                 215                 220

Gly His Leu Ile Val Gly Ser Thr Pro Thr Arg Ser Gln Leu Ala Thr
225                 230                 235                 240

Ala Leu Gln Arg Phe Thr Ala Leu Gly Leu Glu Val Ala Tyr Thr Glu
            245                 250                 255

Leu Asp Ile Arg His Ser Ser Leu Pro Ala Ser Ser Ala Leu Ala
        260                 265                 270

Thr Gln Gly Asn Asp Phe Ala Asn Val Val Gly Ser Cys Leu Asp Thr
    275                 280                 285

Ala Gly Cys Val Gly Val Thr Val Trp Gly Phe Thr Asp Ala His Ser
290                 295                 300

Trp Ile Pro Asn Thr Phe Pro Gly Gln Gly Asp Ala Leu Ile Tyr Asp
305                 310                 315                 320

Ser Asn Tyr Asn Lys Lys Pro Ala Trp Thr Ser Ile Ser Ser Val Leu
            325                 330                 335

Ala Ala Lys Ala Thr Gly Ala Pro Pro Ala Ser Ser Ser Thr Thr Leu
        340                 345                 350

Val Thr Ile Thr Thr Pro Pro Ala Ser Thr Ala Ser Ser Ser
355                 360                 365

Ser Ser Ala Thr Pro Thr Ser Val Pro Thr Gln Thr Arg Trp Gly Gln
    370                 375                 380

Cys Gly Gly Ile Gly Trp Thr Gly Pro Thr Gln Cys Glu Ser Pro Trp
385                 390                 395                 400

Thr Cys Gln Lys Leu Asn Asp Trp Tyr Trp Gln Cys Leu
            405                 410

<210> SEQ ID NO 45
<211> LENGTH: 1427
<212> TYPE: DNA
<213> ORGANISM: Penicillium chrysogenum

<400> SEQUENCE: 45

```
atggttcatt tctctaccat tgccctggcg ttggccagtg cccttcctca gttgtatggt    60
ttatctttca atctcgagca tgaacagtca ttgatgccct ttttcttca ataggaccca    120 aggagccggc ttgcacacct ctgctgttgc aaaggggaag ctatacttcg atcagccac    180 tgataacccc gagttgactg atgttccgta ccttacccaa ctgagcaaca cagatgactt    240
cggccaaatt acaccgggca attcgcagaa ggttagataa cccttaccgt gtaattcatg    300
ccctcactaa ttgtcgctag tgggatgcac ttgagccgtc ccaaaacacc ttctcctata    360
ccaatggaga tgtcattgcc aaccttgctg ctaagaatgg ccaaaagctg cggtgccata    420
ctctggtttg gcatagccaa ttgcccagct ggggtaagct ctgttatagc atgtctttca    480
atccatgagt agctatctaa ttggtaaata gtctcaagtg gctcctggac caacgcaact    540
ctgattgctg ccatgaaaaa ccacatcacc aacgtggtca ctcactacaa aggcaaatgt    600
```

-continued

```
tacgcttggg atgttgtcaa tgagggtcag tactgaaccc aagaacgaat tatatcatca    660
tcatcatcaa atagctaata tatgcattgc tagctcttaa cgaggacggt acctatcgtg    720
acagtgtctt ctacaaatac atcggcgagg cattccttcc catcgcgttt gcaacagcag    780
ccgccgcaga tccagacgcc aagctctact acaacgacta caacatcgaa tcacccggtt    840
ccaagtcatc aggtgcccag agaatcgtca agctggtgca gcagtacggt gccaagatcg    900
acggtgtcgg actgcaggca cactttattg tcggaagtac ccctagtcag agcgcgcaga    960
ctaccaacct agccgcattc acagccctgg agttgacgt tgcctacact gaactcgaca    1020
tccgtatgac tctgccatca actactgcct tgcttaccca gcagtccacc gactataaaa    1080
ataccgttgc ggcgtgcatg gcaaatacca agtgcgttgg cattactatt tgggactaca    1140
cggataaata ctcgtgggtt ccgagcacat tccctggtca gggtgatgcg tgtccttggg    1200 ataagaaacct cgtgaagaag cctgcttatg ctggtatctt ggctgctctg gcggtacgt    1260 cctccactac tactactctg gttactagca cgactaccgc cggttctggc ggtgctacta    1320
gagtcccgct ctatggtcag tgtggtggct cgggctggac tggaggcaca acttgcgcca    1380
gtggaacctg caaacacatc aatgactggt actcgcagtg tctatag                 1427
```

<210> SEQ ID NO 46
<211> LENGTH: 396
<212> TYPE: PRT
<213> ORGANISM: Penicillium chrysogenum

<400> SEQUENCE: 46

```
Met Val His Phe Ser Thr Ile Ala Leu Ala Leu Ala Ser Ala Leu Pro
1               5                   10                  15

Gln Leu Thr Gln Gly Ala Gly Leu His Thr Ser Ala Val Ala Lys Gly
            20                  25                  30

Lys Leu Tyr Phe Gly Ser Ala Thr Asp Asn Pro Glu Leu Thr Asp Val
        35                  40                  45

Pro Tyr Leu Thr Gln Leu Ser Asn Thr Asp Asp Phe Gly Gln Ile Thr
    50                  55                  60

Pro Gly Asn Ser Gln Lys Trp Asp Ala Leu Glu Pro Ser Gln Asn Thr
65                  70                  75                  80

Phe Ser Tyr Thr Asn Gly Asp Val Ile Ala Asn Leu Ala Ala Lys Asn
                85                  90                  95

Gly Gln Lys Leu Arg Cys His Thr Leu Val Trp His Ser Gln Leu Pro
            100                 105                 110

Ser Trp Val Ser Ser Gly Ser Trp Thr Asn Ala Thr Leu Ile Ala Ala
        115                 120                 125

Met Lys Asn His Ile Thr Asn Val Val Thr His Tyr Lys Gly Lys Cys
    130                 135                 140

Tyr Ala Trp Asp Val Val Asn Glu Ala Leu Asn Glu Asp Gly Thr Tyr
145                 150                 155                 160

Arg Asp Ser Val Phe Tyr Lys Tyr Ile Gly Glu Ala Phe Leu Pro Ile
                165                 170                 175

Ala Phe Ala Thr Ala Ala Ala Asp Pro Asp Ala Lys Leu Tyr Tyr
            180                 185                 190

Asn Asp Tyr Asn Ile Glu Ser Pro Gly Ser Lys Ser Ser Gly Ala Gln
        195                 200                 205

Arg Ile Val Lys Leu Val Gln Gln Tyr Gly Ala Lys Ile Asp Gly Val
    210                 215                 220
```

```
Gly Leu Gln Ala His Phe Ile Val Gly Ser Thr Pro Ser Gln Ser Ala
225                 230                 235                 240

Gln Thr Thr Asn Leu Ala Ala Phe Thr Ala Leu Gly Val Asp Val Ala
            245                 250                 255

Tyr Thr Glu Leu Asp Ile Arg Met Thr Leu Pro Ser Thr Thr Ala Leu
        260                 265                 270

Leu Thr Gln Gln Ser Thr Asp Tyr Lys Asn Thr Val Ala Ala Cys Met
    275                 280                 285

Ala Asn Thr Lys Cys Val Gly Ile Thr Ile Trp Asp Tyr Thr Asp Lys
290                 295                 300

Tyr Ser Trp Val Pro Ser Thr Phe Pro Gly Gln Gly Asp Ala Cys Pro
305                 310                 315                 320

Trp Asp Lys Asn Leu Val Lys Lys Pro Ala Tyr Ala Gly Ile Leu Ala
            325                 330                 335

Ala Leu Gly Gly Thr Ser Ser Thr Thr Thr Leu Val Thr Ser Thr
        340                 345                 350

Thr Thr Ala Gly Ser Gly Gly Ala Thr Arg Val Pro Leu Tyr Gly Gln
    355                 360                 365

Cys Gly Gly Ser Gly Trp Thr Gly Thr Thr Cys Ala Ser Gly Thr
370                 375                 380

Cys Lys His Ile Asn Asp Trp Tyr Ser Gln Cys Leu
385                 390                 395

<210> SEQ ID NO 47
<211> LENGTH: 1438
<212> TYPE: DNA
<213> ORGANISM: Rasamsonia emersonii

<400> SEQUENCE: 47
atggttcgcc tcagtccagt cttgctcgcc tccatcgcag gctctggcct gcctctgtac      60
gtactcacgt ctacatctga cgagcccatac tgatgaatgc agagcccaag cagcaggcct     120
caacacagcc gccaaagcca tcggcctgaa atactttggc acagcgaccg acaaccccga     180
gctgagcgac accgcgtacg agacgcagct caacaacacg caggatttcg gcagttgac      240 gccggcgaat tcgatgaagg tgtgtctgaa ctatttacct cctgggggg gtttcctgct      300 gatggttctt gcagtgggat gccaccgagc ccgagcagaa tgtcttcacg tttagcgccg     360
gcgatcagat tgccaacttg gccaaggcga atggccagat gttgcggtgt cataatcttg     420
tttggtacaa tcagttgccg tcgtggggta tgatatttgc attcctgttg tgatgattgt     480
tcgtgctgat ctgtgttttt atgacagtca ccagtggctc ctggaccaac gagacgctgc     540
ttgctgccat gaagaatcac atcaccaacg tcgttaccca ttacaagggc cagtgctacg     600
catgggatgt cgttaatgag ggtacgtctg cattgtcagt attcacagcg aatgtgaact     660
aattgcgaca gccctcaacg acgacggcac ctaccgcagc aacgtcttct accagtacat     720
cggtgaggcg tacatccca tcgccttcgc gacggccgcc gccgccgacc caacgccaa      780 gctgtactac aacgactaca acatcgagta cccgggggcc aaggcgacgg cggcgcagaa     840
cctggtcaag ctggtgcagt cgtacggcgc gcgcatcgac ggcgtcggcc tgcagtcgca     900
cttcatcgtg ggcgagacgc ccagcaccag ctcccagcag cagaacatgg ccgccttcac     960
ggcgctgggc gtcgaggtcg ccatcaccga gctcgacatc cgcatgcagc tgcccgagac    1020
ggaagccctg ctgacgcagc aggccaccga ctaccagagc accgtgcagg cctgcgccaa    1080
caccaagggc tgcgtcggca tcaccgtctg ggactggacc gacaagtact cgtgggtgcc    1140
```

```
cagcaccttc tcgggctatg cgacgcctg tccctgggac gccaactacc agaagaagcc    1200
cgcgtacgaa ggcatcctca ctgggcttgg acagacggtc accagcacca cctacatcat    1260
ctcgccgacg acgtctgtcg aacgggcac gacgacctcg agcggcggaa cggcggcac     1320 gactggcgtg cccagcatt gggagcagtg cggtggactg ggctggactg gtccgacggt    1380
ttgcgcaagt ggctacactt gcactgtcat caatgagtat tactcgcagt gtctgtaa     1438
```

<210> SEQ ID NO 48
<211> LENGTH: 408
<212> TYPE: PRT
<213> ORGANISM: Rasamsonia emersonii

<400> SEQUENCE: 48

```
Met Val Arg Leu Ser Pro Val Leu Leu Ala Ser Ile Ala Gly Ser Gly
1               5                   10                  15

Leu Pro Leu Ala Gln Ala Ala Gly Leu Asn Thr Ala Ala Lys Ala Ile
                20                  25                  30

Gly Leu Lys Tyr Phe Gly Thr Ala Thr Asp Asn Pro Glu Leu Ser Asp
            35                  40                  45

Thr Ala Tyr Glu Thr Gln Leu Asn Asn Thr Gln Asp Phe Gly Gln Leu
    50                  55                  60

Thr Pro Ala Asn Ser Met Lys Trp Asp Ala Thr Glu Pro Glu Gln Asn
65                  70                  75                  80

Val Phe Thr Phe Ser Ala Gly Asp Gln Ile Ala Asn Leu Ala Lys Ala
                85                  90                  95

Asn Gly Gln Met Leu Arg Cys His Asn Leu Val Trp Tyr Asn Gln Leu
            100                 105                 110

Pro Ser Trp Val Thr Ser Gly Ser Trp Thr Asn Glu Thr Leu Leu Ala
        115                 120                 125

Ala Met Lys Asn His Ile Thr Asn Val Val Thr His Tyr Lys Gly Gln
    130                 135                 140

Cys Tyr Ala Trp Asp Val Val Asn Glu Ala Leu Asn Asp Asp Gly Thr
145                 150                 155                 160

Tyr Arg Ser Asn Val Phe Tyr Gln Tyr Ile Gly Glu Ala Tyr Ile Pro
                165                 170                 175

Ile Ala Phe Ala Thr Ala Ala Ala Asp Pro Asn Ala Lys Leu Tyr
            180                 185                 190

Tyr Asn Asp Tyr Asn Ile Glu Tyr Pro Gly Ala Lys Ala Thr Ala Ala
        195                 200                 205

Gln Asn Leu Val Lys Leu Val Gln Ser Tyr Gly Ala Arg Ile Asp Gly
    210                 215                 220

Val Gly Leu Gln Ser His Phe Ile Val Gly Glu Thr Pro Ser Thr Ser
225                 230                 235                 240

Ser Gln Gln Gln Asn Met Ala Ala Phe Thr Ala Leu Gly Val Glu Val
                245                 250                 255

Ala Ile Thr Glu Leu Asp Ile Arg Met Gln Leu Pro Glu Thr Glu Ala
            260                 265                 270

Leu Leu Thr Gln Gln Ala Thr Asp Tyr Gln Ser Thr Val Gln Ala Cys
        275                 280                 285

Ala Asn Thr Lys Gly Cys Val Gly Ile Thr Val Trp Asp Trp Thr Asp
    290                 295                 300

Lys Tyr Ser Trp Val Pro Ser Thr Phe Ser Gly Tyr Gly Asp Ala Cys
305                 310                 315                 320

Pro Trp Asp Ala Asn Tyr Gln Lys Lys Pro Ala Tyr Glu Gly Ile Leu
```

```
                325                 330                 335
Thr Gly Leu Gly Gln Thr Val Thr Ser Thr Thr Tyr Ile Ile Ser Pro
            340                 345                 350

Thr Thr Ser Val Gly Thr Gly Thr Thr Thr Ser Ser Gly Gly Ser Gly
        355                 360                 365

Gly Thr Thr Gly Val Ala Gln His Trp Glu Gln Cys Gly Gly Leu Gly
    370                 375                 380

Trp Thr Gly Pro Thr Val Cys Ala Ser Gly Tyr Thr Cys Thr Val Ile
385                 390                 395                 400

Asn Glu Tyr Tyr Ser Gln Cys Leu
                405

<210> SEQ ID NO 49
<211> LENGTH: 1221
<212> TYPE: DNA
<213> ORGANISM: Aspergillus aculeatus

<400> SEQUENCE: 49
atggtcggac tgctttcaat caccgcggcg cttgccgcga ctgtgttgcc aaacattgtc      60
tctgccgttg gtctggatca ggctgcagtt gccaaaggac ttcaatactt tggcacagct     120
acggataatc ccgagctcac ggatattcca tacgttactc agctgaacaa caccgcggac     180
tttggtcaaa ttacccctgg aaactcgatg aagtgggatg ccacagaacc atctcagggc     240
accttcacgt tcacgaaagg cgatgtcatt gcagatctgg ctgagggtaa tggccaatat     300
ctccgatgtc atactctggt ttggtataat cagctaccta gctgggtgac tagcggaact     360
tggactaatg ctactctcac cgccgcattg aagaaccaca tcacgaatgt ggtgtcgcac     420
tacaaaggga atgtcttca ttgggacgtg gtcaatgagg cgttgaatga cgacggaacc      480
taccgcacca acatcttcta caccaccatc ggcgaagcct acatccccat gccttttgcc     540
gcagcggctg cagccgaccc ggacgcgaag ctgttctaca atgactacaa cctcgaatac     600
ggcggcgcca agccgccag cgcccgcgcc attgtccagc tggtcaagaa tgcaggtgcc      660
aagatcgacg gggtagggtt gcaggcccat ttcagcgtcg gcaccgtgcc gagtacgagc     720
tcgctcgtct cggtgctgca atctttcact gcgctcgggg tcgaggtcgc ctacacggag     780
gccgacgtgc gcattctcct gcccaccacc gccactaccc tggcccaaca gtcgagcgat     840
ttccaggccc tggtgcaatc ctgtgtgcag acaacgggct gcgtcggctt cactatctgg     900
gattggacag ataagtacag ctgggttccc agcacgttct cgggctatgg ggcggcgcta     960
ccctgggatg agaacctggt taagaagccc gcgtacaatg gcttgttggc cggcatgggg    1020
gttacagtta ccactacgac taccaccacc actgctactg ccactggtaa gactacgact    1080
accacaacgg gtgccacgag cacggggact acggctgcgc attgggggca gtgtggaggg    1140
ctcaactgga gtggaccgac ggcgtgtgcc actgggtaca cctgcactta tgtcaatgac    1200
tattactcgc agtgtctgtg a                                              1221

<210> SEQ ID NO 50
<211> LENGTH: 406
<212> TYPE: PRT
<213> ORGANISM: Aspergillus aculeatus

<400> SEQUENCE: 50

Met Val Gly Leu Leu Ser Ile Thr Ala Ala Leu Ala Ala Thr Val Leu
1               5                   10                  15

Pro Asn Ile Val Ser Ala Val Gly Leu Asp Gln Ala Ala Val Ala Lys
```

```
            20                  25                  30
Gly Leu Gln Tyr Phe Gly Thr Ala Thr Asp Asn Pro Glu Leu Thr Asp
             35                  40                  45

Ile Pro Tyr Val Thr Gln Leu Asn Asn Thr Ala Asp Phe Gly Gln Ile
 50                  55                  60

Thr Pro Gly Asn Ser Met Lys Trp Asp Ala Thr Glu Pro Ser Gln Gly
 65                  70                  75                  80

Thr Phe Thr Phe Thr Lys Gly Asp Val Ile Ala Asp Leu Ala Glu Gly
                 85                  90                  95

Asn Gly Gln Tyr Leu Arg Cys His Thr Leu Val Trp Tyr Asn Gln Leu
                100                 105                 110

Pro Ser Trp Val Thr Ser Gly Thr Trp Thr Asn Ala Thr Leu Thr Ala
                115                 120                 125

Ala Leu Lys Asn His Ile Thr Asn Val Val Ser His Tyr Lys Gly Lys
            130                 135                 140

Cys Leu His Trp Asp Val Val Asn Glu Ala Leu Asn Asp Asp Gly Thr
145                 150                 155                 160

Tyr Arg Thr Asn Ile Phe Tyr Thr Thr Ile Gly Glu Ala Tyr Ile Pro
                165                 170                 175

Ile Ala Phe Ala Ala Ala Ala Ala Asp Pro Asp Ala Lys Leu Phe
                180                 185                 190

Tyr Asn Asp Tyr Asn Leu Glu Tyr Gly Ala Lys Ala Ser Ala
                195                 200                 205

Arg Ala Ile Val Gln Leu Val Lys Asn Ala Gly Ala Lys Ile Asp Gly
            210                 215                 220

Val Gly Leu Gln Ala His Phe Ser Val Gly Thr Val Pro Ser Thr Ser
225                 230                 235                 240

Ser Leu Val Ser Val Leu Gln Ser Phe Thr Ala Leu Gly Val Glu Val
                245                 250                 255

Ala Tyr Thr Glu Ala Asp Val Arg Ile Leu Leu Pro Thr Thr Ala Thr
                260                 265                 270

Thr Leu Ala Gln Gln Ser Ser Asp Phe Gln Ala Leu Val Gln Ser Cys
            275                 280                 285

Val Gln Thr Gly Cys Val Gly Phe Thr Ile Trp Asp Trp Thr Asp
            290                 295                 300

Lys Tyr Ser Trp Val Pro Ser Thr Phe Ser Gly Tyr Gly Ala Ala Leu
305                 310                 315                 320

Pro Trp Asp Glu Asn Leu Val Lys Lys Pro Ala Tyr Asn Gly Leu Leu
                325                 330                 335

Ala Gly Met Gly Val Thr Val Thr Thr Thr Thr Thr Thr Thr Ala
                340                 345                 350

Thr Ala Thr Gly Lys Thr Thr Thr Thr Gly Ala Thr Ser Thr
            355                 360                 365

Gly Thr Thr Ala Ala His Trp Gly Gln Cys Gly Gly Leu Asn Trp Ser
            370                 375                 380

Gly Pro Thr Ala Cys Ala Thr Gly Tyr Thr Cys Thr Tyr Val Asn Asp
385                 390                 395                 400

Tyr Tyr Ser Gln Cys Leu
                405

<210> SEQ ID NO 51
<211> LENGTH: 1352
<212> TYPE: DNA
<213> ORGANISM: Trichoderma reesei
```

<400> SEQUENCE: 51

```
atgaaagcaa acgtcatctt gtgcctcctg gccccctgg tcgccgctct ccccaccgaa      60
accatccacc tcgaccccga gctcgccgct ctccgcgcca acctcaccga gcgaacagcc    120
gacctctggg accgccaagc ctctcaaagc atcgaccagc tcatcaagag aaaaggcaag    180
ctctactttg gcaccgccac cgaccgcggc ctcctccaac gggaaaagaa cgcggccatc    240
atccaggcag acctcggcca ggtgacgccg agaacagca tgaagtggca gtcgctcgag     300
aacaaccaag gccagctgaa ctggggagac gccgactatc tcgtcaactt gcccagcaa     360
aacggcaagt cgatacgcgg ccacactctg atctggcact cgcagctgcc tcgtgggtg     420
aacaatatca caacgcgga tactctgcgg caagtcatcc gcacccatgt ctctactgtg     480
gttgggcggt acaagggcaa gattcgtgct gggtgagtt ttgaacacca catgccctt      540
ttcttagtcc gctcctcctc ctcttggaac ttctcacagt tatagccgta caacattc      600
gacaggaaat ttaggatgac aactactgac tgacttgtgt gtgtgatggc gataggacgt   660
ggtcaatgaa atcttcaacg aggatggaac gctgcgctct tcagtcttt ccaggctcct    720
cggcgaggag tttgtctcga ttgccttcg tgctgctcga gatgctgacc cttctgcccg     780
tctttacatc aacgactaca atctcgaccg cgccaactat ggcaaggtca acgggttgaa   840
gacttacgtc tccaagtgga tctctcaagg agttcccatt gacggtattg gtgagccacg    900
acccctaaat gtcccccatt agagtctctt tctagagcca aggcttgaag ccattcaggg    960
actgacacga gagccttctc tacaggaagc cagtcccatc tcagcggcgg cggaggctct   1020
ggtacgctgg gtgcgctcca gcagctggca acggtacccg tcaccgagct ggccattacc   1080
gagctggaca ttcaggggc accgacgacg gattacaccc aagttgttca agcatgcctg    1140
agcgtctcca gtgcgtcgg catcaccgtg tgggcatca gtgacaaggt aagttgcttc    1200
ccctgtctgt gcttatcaac tgtaagcagc aacaactgat gctgtctgtc tttacctagg   1260
actcgtggcg tgccagcacc aaccctcttc tgtttgacgc aaacttcaac cccaagccgg   1320
catataacag cattgttggc atcttacaat ag                                 1352
```

<210> SEQ ID NO 52
<211> LENGTH: 347
<212> TYPE: PRT
<213> ORGANISM: Trichoderma reesei

<400> SEQUENCE: 52

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
        35                  40                  45

Gln Ser Ile Asp Gln Leu Ile Lys Arg Lys Gly Lys Leu Tyr Phe Gly
    50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His

```
                115                 120                 125
Thr Leu Ile Trp His Ser Gln Leu Pro Ala Trp Val Asn Asn Ile Asn
        130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 53
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 53
gtccgtacct cctgtcgtag tagtagtagt agtagtggtc gttgtgg                  47

<210> SEQ ID NO 54
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 54
ccacaacgac cactactact actactacta cgacaggagg tacggac                  47

<210> SEQ ID NO 55
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 55
gtagtagtag tggtcgttgt ggtagtggag ccgcttgctc caagac                   46
```

<210> SEQ ID NO 56
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 56
gtcttggagc aagcggctcc actaccacaa cgaccactac tactac         46

<210> SEQ ID NO 57
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 57
gcttgctcca agacccgcca tgatgccatc gtacgctggc ttctt           45

<210> SEQ ID NO 58
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 58
aagaagccag cgtacgatgg catcatggcg ggtcttggag caagc           45

<210> SEQ ID NO 59
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 59
gtcggtccag tcccagatag tgatacccac gcagccagtg gtgc            44

<210> SEQ ID NO 60
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 60
gcaccactgg ctgcgtgggt atcactatct gggactggac cgac            44

<210> SEQ ID NO 61
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 61
catgctgcgg ccacgccttg gtagtcagtg gactgctggg cca             43

<210> SEQ ID NO 62
<211> LENGTH: 43
<212> TYPE: DNA
<213> ORGANISM: Artificial Sequence
<220> FEATURE:

<223> OTHER INFORMATION: Artificial DNA Primer

<400> SEQUENCE: 62
tggcccagca gtccactgac taccaaggcg tggccgcagc atg             43

<210> SEQ ID NO 63
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 63
cacctcaacg ccgagagcag tgaagccctt caagacggtc gtcag           45

<210> SEQ ID NO 64
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 64
ctgacgaccg tcttgaaggg cttcactgct ctcggcgttg aggtg           45

<210> SEQ ID NO 65
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 65
gcccttcaag acggtcgtca gattcgattg actcggagtg ctgcc           45

<210> SEQ ID NO 66
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 66
ggcagcactc cgagtcaatc gaatctgacg accgtcttga agggc           45

<210> SEQ ID NO 67
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 67
ggaggccgac gccgtcgatt cgcgcgccgt aggccttgat ca              42

<210> SEQ ID NO 68
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 68
tgatcaaggc ctacggcgcg cgaatcgacg gcgtcggcct cc              42

<210> SEQ ID NO 69
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 69
tcgatcttcg cgccgtaggc ctggatcatc ttgacgatat tctgcg    46

<210> SEQ ID NO 70
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 70
cgcagaatat cgtcaagatg atccaggcct acggcgcgaa gatcga    46

<210> SEQ ID NO 71
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 71
cttcgcgccg taggccttga tcagcttgac gatattctgc gcagca    46

<210> SEQ ID NO 72
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 72
tgctgcgcag aatatcgtca agctgatcaa ggcctacggc gcgaag    46

<210> SEQ ID NO 73
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 73
cagagttacg gaaagtaccg tcgtcgttca gggctagatt gacaggc    47

<210> SEQ ID NO 74
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 74
gcctgtcaat ctagccctga acgacgacgg tactttccgt aactctg    47

<210> SEQ ID NO 75
<211> LENGTH: 47
<212> TYPE: DNA
<213> ORGANISM: Artificial Sequence
<220> FEATURE:
<223> OTHER INFORMATION: Artificial DNA Primer -continued

<400> SEQUENCE: 75
agacaagacg tttacatacc ccagctcggt agctgactgt gccagac    47

<210> SEQ ID NO 76
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 76
gtctggcaca gtcagctacc gagctggggt atgtaaacgt cttgtct    47

<210> SEQ ID NO 77
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 77
ccattcttgt tcgccagatt gacgatggcg tctccatttg cgaacga    47

<210> SEQ ID NO 78
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 78
tcgttcgcaa atggagacgc catcgtcaat ctggcgaaca agaatgg    47

<210> SEQ ID NO 79
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 79
gattgaccac ggcgtctcca ttagtgaacg aaaaagaatt ctgagaagg    49

<210> SEQ ID NO 80
<211> LENGTH: 49
<212> TYPE: DNA
<213> ORGANISM: Artificial Sequence
<220> FEATURE:
<223> OTHER INFORMATION: Artificial DNA Primer

<400> SEQUENCE: 80
ccttctcaga attcttttc gttcactaat ggagacgccg tggtcaatc    49

<210> SEQ ID NO 81
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 81
gcctgtcaat ctagccctga acgacgacgg tactttccgt aactctg    47

<210> SEQ ID NO 82
<211> LENGTH: 45

```
<212> TYPE: DNA
<213> ORGANISM: Artificial Sequence
<220> FEATURE:
<223> OTHER INFORMATION: Artificial DNA Primer

<400> SEQUENCE: 82
ctgacgaccg tcttgaaggg cttcactgct ctcggcgttg aggtg               45

<210> SEQ ID NO 83
<211> LENGTH: 44
<212> TYPE: DNA
<213> ORGANISM: Artificial Sequence
<220> FEATURE:
<223> OTHER INFORMATION: Artificial DNA Primer

<400> SEQUENCE: 83
gcaccactgg ctgcgtgggt atcactatct gggactggac cgac                44

<210> SEQ ID NO 84
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 84
tgctgcgcag aatatcgtca agctgatcaa ggcctacggc gcgaag              46

<210> SEQ ID NO 85
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 85
tgatcaaggc ctacggcgcg cgaatcgacg gcgtcggcct cc                  42

<210> SEQ ID NO 86
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 86
ccacaacgac cactactact actactacta cgacaggagg tacggac             47

<210> SEQ ID NO 87
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 87
ggcagcactc cgagtcaatc gaatctgacg accgtcttga agggc               45

<210> SEQ ID NO 88
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 88
```
tgatcaaggc ctacggcgcg cgaatcgacg gcgtcggcct cc                               42

<210> SEQ ID NO 89
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 89
ccacaacgac cactactact actactacta cgacaggagg tacggac                         47

<210> SEQ ID NO 90
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 90
ggcagcactc cgagtcaatc gaatctgacg accgtcttga agggc                           45

<210> SEQ ID NO 91
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 91
tgatcaaggc ctacggcgcg cgaatcgacg gcgtcggcct cc                               42

<210> SEQ ID NO 92
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 92
ccacaacgac cactactact actactacta cgacaggagg tacggac                         47

<210> SEQ ID NO 93
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 93
ggcagcactc cgagtcaatc gaatctgacg accgtcttga agggc                           45

<210> SEQ ID NO 94
<211> LENGTH: 42
<212> TYPE: DNA
<213> ORGANISM: Artificial Sequence
<220> FEATURE:
<223> OTHER INFORMATION: Artificial DNA Primer

<400> SEQUENCE: 94
tgatcaaggc ctacggcgcg cgaatcgacg gcgtcggcct cc                               42

<210> SEQ ID NO 95
<211> LENGTH: 47
<212> TYPE: DNA
<213> ORGANISM: Artificial Sequence

```
<220> FEATURE:
<223> OTHER INFORMATION: Artificial DNA Primer

<400> SEQUENCE: 95
ccacaacgac cactactact actactacta cgacaggagg tacggac          47

<210> SEQ ID NO 96
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 96
ggcagcactc cgagtcaatc gaatctgacg accgtcttga agggc             45

<210> SEQ ID NO 97
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 97
tcgttcgcaa atggagacgc catcgtcaat ctggcgaaca agaatgg           47

<210> SEQ ID NO 98
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 98
gtctggcaca gtcagctacc gagctggggt atgtaaacgt cttgtct           47

<210> SEQ ID NO 99
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 99
ggcagcactc cgagtcaatc gaatctgacg accgtcttga agggc             45

<210> SEQ ID NO 100
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 100
tcgttcgcaa atggagacgc catcgtcaat ctggcgaaca agaatgg           47

<210> SEQ ID NO 101
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 101
gtctggcaca gtcagctacc gagctggggt atgtaaacgt cttgtct           47
```

```
<210> SEQ ID NO 102
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 102
ggcagcactc cgagtcaatc gaatctgacg accgtcttga agggc                45

<210> SEQ ID NO 103
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 103
tcgttcgcaa atggagacgc catcgtcaat ctggcgaaca agaatgg              47

<210> SEQ ID NO 104
<211> LENGTH: 47
<212> TYPE: DNA
<213> ORGANISM: Artificial Sequence
<220> FEATURE:
<223> OTHER INFORMATION: Artificial DNA Primer

<400> SEQUENCE: 104
gtctggcaca gtcagctacc gagctggggt atgtaaacgt cttgtct              47

<210> SEQ ID NO 105
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 105
ggcagcactc cgagtcaatc gaatctgacg accgtcttga agggc                45

<210> SEQ ID NO 106
<211> LENGTH: 43
<212> TYPE: DNA
<213> ORGANISM: Artificial Sequence
<220> FEATURE:
<223> OTHER INFORMATION: Artificial DNA Primer

<400> SEQUENCE: 106
tggcccagca gtccactgac taccaaggcg tggccgcagc atg                  43

<210> SEQ ID NO 107
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 107
aagaagccag cgtacgatgg catcatggcg ggtcttggag caagc                45

<210> SEQ ID NO 108
<211> LENGTH: 44
<212> TYPE: DNA
<213> ORGANISM: Artificial Sequence
<220> FEATURE:
<223> OTHER INFORMATION: Artificial DNA Primer
```

```
<400> SEQUENCE: 108
gcaccactgg ctgcgtgggt atcactatct gggactggac cgac          44

<210> SEQ ID NO 109
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 109
tccactgact tccaaggcgt ggtcgcagca tgcgttagca ccact         45

<210> SEQ ID NO 110
<211> LENGTH: 45
<212> TYPE: DNA
<213> ORGANISM: Artificial Sequence
<220> FEATURE:
<223> OTHER INFORMATION: Artificial DNA Primer

<400> SEQUENCE: 110
gcgaacaaga atggccagct gctgcgatgc catactctgg tctgg         45

<210> SEQ ID NO 111
<211> LENGTH: 46
<212> TYPE: DNA
<213> ORGANISM: Artificial Sequence
<220> FEATURE:
<223> OTHER INFORMATION: Artificial DNA Primer

<400> SEQUENCE: 111
ttcgcaaatg gagacgccgt ggccaatctg gcgaacaaga atggcc        46
```